(12) United States Patent
Perkins et al.

(10) Patent No.: US 7,091,000 B2
(45) Date of Patent: Aug. 15, 2006

(54) BACTERIAL STRAINS WHICH OVERPRODUCE RIBOFLAVIN AND METHODS OF USE THEREOF

(75) Inventors: John B. Perkins, Reading, MA (US); Alan Sloma, Watertown, MA (US); Janice G. Pero, Lexington, MA (US); Randolph T. Hatch, Wellesley, MA (US); Theron Hermann, Framingham, MA (US); Thomas Erdenberger, Arlington, MA (US)

(73) Assignee: DSM Nutritional Products, Inc., Parsippany, NJ (US)

( * ) Notice: Subject to any disclaimer, the term of this patent is extended or adjusted under 35 U.S.C. 154(b) by 34 days.

(21) Appl. No.: 10/361,522

(22) Filed: Feb. 10, 2003

(65) Prior Publication Data

US 2003/0232406 A1    Dec. 18, 2003

Related U.S. Application Data

(60) Continuation of application No. 09/306,615, filed on May 6, 1999, now Pat. No. 6,551,813, which is a division of application No. 09/138,775, filed on Aug. 24, 1998, now Pat. No. 5,925,538, which is a division of application No. 08/384,626, filed on Feb. 6, 1995, now Pat. No. 5,837,528, which is a continuation of application No. 07/873,572, filed on Apr. 21, 1992, now abandoned, which is a continuation of application No. 07/581,048, filed on Sep. 11, 1990, now abandoned, which is a continuation-in-part of application No. 07/370,378, filed on Jun. 22, 1989, now abandoned.

(51) Int. Cl.
C12P 21/00 (2006.01)
C07H 21/04 (2006.01)
A61K 38/16 (2006.01)
A61K 38/43 (2006.01)

(52) U.S. Cl. .................. 435/68.1; 435/69.1; 435/71.1; 514/12; 536/23.2; 536/23.7

(58) Field of Classification Search ............. 435/253.6, 435/69.1, 69.3, 183
See application file for complete search history.

(56) References Cited

U.S. PATENT DOCUMENTS

| | | | |
|---|---|---|---|
| 3,900,368 A | 8/1975 | Enei et al. | |
| 4,086,135 A | 4/1978 | Balana et al. | |
| 4,783,405 A | 11/1988 | Kovacevic et al. | |
| 4,794,081 A | 12/1988 | Kawai et al. | |

FOREIGN PATENT DOCUMENTS

| | | | |
|---|---|---|---|
| EP | 0 137 226 A2 | 4/1985 | |
| EP | 0 146 981 A1 | 7/1985 | |
| EP | 0 190 921 A2 | 8/1986 | |
| EP | 0 229 712 A2 | 7/1987 | |
| FR | 2 546 907 | 12/1984 | |
| WO | WO 87/05932 | 11/1987 | |

OTHER PUBLICATIONS

Zubay G, 1973. In Vitro Synthesis of Protein in Microbial Systems. Annual Review of Genetics☐☐vol. 7: 267-287.*
Laemmli UK, 1970. Cleavage of structural proteins during the assembly of the head of bacteriophage T4. Nature 227:680-685.*
Accelrys website, www.accelrys.com/about/gcg.html. Viewed Nov. 10, 2004.*
Pridgeon JW et al. 2003. Biol Proced Online 5(1): 228-237.*
Grunstein M et al. 1975. Colony hybridization: a method for the isolation of cloned DNAs that contain a specific gene. Proc Natl Acad Sci USA 72: 3961-3965.*
Windholz et al., eds. Merck & Co., p. 8099 (1983).
Matsui et al., Agric. Biol. Chem., 46:2203 (1982).
Rabinovich et al., Genetika, 14:1696 (1978) (with accompanying English translation).
Chikindas et al., Mol. Genet. Mik. Virusol., No. 2:20 (1987).
Morozov et al., Mol. Genet. Mik. Virusol., 7:42 (1984) (with accompanying English translation).
Morozov et al., Mol. Genet. Mik. Virusol., No. 11:11 (1984) (with accompanying English translation).
Morozov et al., Mol. Genet. Mik. Virusol., No. 12:14 (1985) (with accompanying English translation).
Chikindas et al., Mol. Genet. Mik. Virusol., No. 4:22 (1987) (with accompanying English translation).
Chikindas et al., 5 SSSR, 298:997 (1988) (with accompanying English translation).
Okunev et al., Genetika, 7:1061 (1984) (with accompanying English translation).
Gryczan et al., J. Bact., 134:318-329 (1978).
Janniere et al., Gene, 40:47-55 (1985).
Osina et al. Febs Letters, 196:75 (1980).
Sloma et al., J. Bact., 170:5557 (1988).
Ludwig et al., Jr. Biol. Chem., 262:1016 (1987).
Mironov et al., Dokl. Akad. Nauk. SSSR, 30:482 (1989).
Chikindas et al., Dokl. Akad. Nauk. SSSR, 298-997 (1988).
Haley et al., J. Biol. Chem., 258:8290-8297 (1983).
Bacher et al., J. Biol. Chem. 255:632-637 (1980).

(Continued)

Primary Examiner—Irene Marx
Assistant Examiner—Lora E Barnhart
(74) Attorney, Agent, or Firm—Bryan Cave LLP

(57) ABSTRACT

Vectors and recombinant bacteria for overproducing riboflavin, in which nucleic acid overproducing riboflavin biosynthetic proteins is introduced in the chromosome of the host organism, e.g. at multiple sites and in multiple copies per site. A rib operon having at least five genes is used to make such recombinant bacteria.

8 Claims, 38 Drawing Sheets

OTHER PUBLICATIONS

Figure 1:
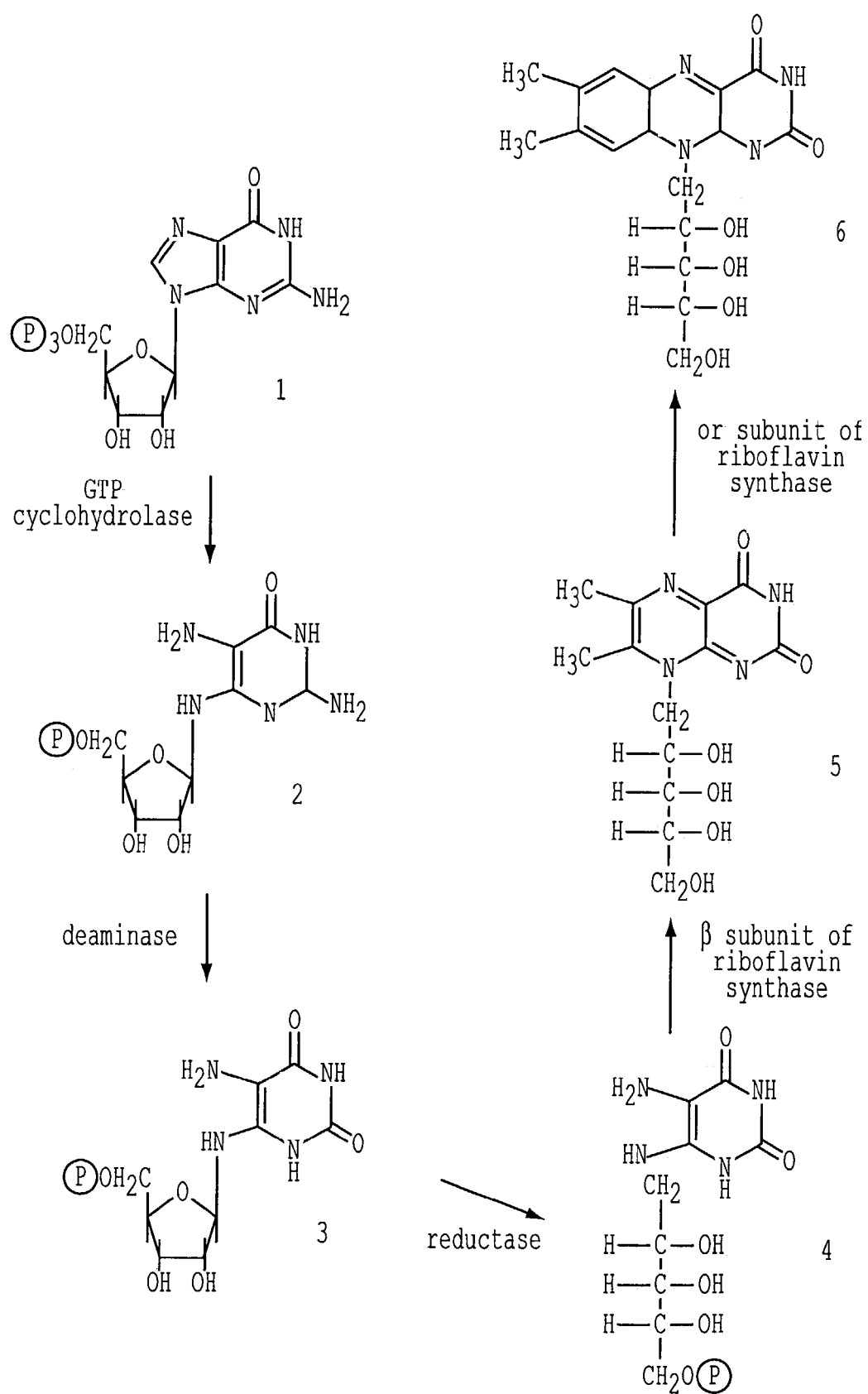

Henner et al., *Gene*, 1235:169-177 (1984).
Zalkin et al., *J. Biol. Chem.* 263:1595-1598 (1988).
Ebbole et al., *J. Biol. Chem.*, 262:8274-8287 (1987).
Shimotsu et al., *J. Bact.*, 166:461-471 (1986).
Rabinovich et al., *Chem. Abstracts*, 88:293 (1978).
Jomantis et al., *Chem. Abstracts*. 97:214 (1982).
Panina et al., *Chem. Abstracts*, 97:214 (1983).
Rabinovich et al., *Chem. Abstracts*, 100:138 (1984).
Okunev et al., *Chem. Abstracts*, 101:157 (1984).
Rabinovich et al., *Chem. Abstracts*, 102:160 (1985).
Matsui et al., *Agric. Biol. Chem.*, 43(8):1739 (1979).
Matsui et al., *Agric. Biol. Chem.*, 43(2):393 (1979).
Matsui et al., *Agric. Biol. Chem.*, 46(8):2003 (1982).
Dubnau "The Molecular Biology of the *Bacilli*," vol. 1, *Bacillus subtilis*, ed. Academic Press (1982).
Chemical Abstracts, 97:214 (1982).
Kallio et al., *Appl. Microbiol. Biotechnol.*, 27:67-71 (1987).
Lee et al., *Mol. Gen. Genet.*, 180:57-65 (1980).
Osburne et al., *J. Gen. Microbiol.*, 132:565-568 (1986).
Yanisch-Perron et al., *Gene*, 33:103-119 (1985).
Gloeckler et al., *Gene*, 87:63-70 (1990).
Panina et al., Chem. Abstract No. 120613X, vol. 98, No. 15, p. 177.
Rodriguez et al., "Vectors: A Survey of Molecular Cloning Vectors and Their Uses," Butterworths, Stoneham, MA (1987).
Maniatis et al., *Molecular Cloning*, Cold Spring Harbor Laboratory, Cold Spring Harbor, New York, pp. 324-325 (1982).
Wahl et al., *Methods in Enzymology*, vol. 152, pp. 399-407 (1987).
Sikyta et al., *Methods in Industrial Microbiology*, Chapter 5, p. 65, John Wiley & Sons, New York (1983).
*ATCC Catalogue of Bacteria*, pp. 290 and 310 (1989).
Difco Manual, p. 225 (1953).

* cited by examiner

| Upstream from ribP1 | Within 5' leader mRNA | At 3' end of rib operon |
|---|---|---|
| ```
      A
   G     T
   G•C
   C•G
   T•A
   T•A
   T•G
   C•G
   C•G
   A•T
   C•G
   T•A
   A•T
   C•G
   A•T
   A•T
   A•T
AA•TG(T₅)~
  #708    #742
ΔG = -20 kcal/mol
``` | ```
            T
         T  A
         T  T
         T•A
         T•A
         T•A
         T•A
         A•T
         A•T
         G•C
         C•G
         C•G
         C•G
         C•G
         G•C
      AAA•T(T₅)~
    #1034    #1062
    ΔG = -26 kcal/mol
``` | ```
         G  A
      T     T
         G•C
         T•A
         C•G
         G•T
         G•C
         A•T
         G•C
         A•T
         C•G
         G•C
         A•T
      ~ TA•T(T₆)~
    #5037    #5064
    ΔG = -16.5 kcal/mol
``` |

FIG. 9

RB-5　　　AATTCATGCATGGATCCGACGGTAAATAAC
　　　　　AAAAGAGGGGAGGGAAACAAATGGAAGAGT
　　　　　ATTATATGAAGCTGGCCTTA

RB-6　　　GATCTAAGGCCAGCTTCATATAATACTCTT
　　　　　CCATTTGTTTCCCTCCCCTCTTTTGTTATT
　　　　　TACCGTCGGATCCATGCATG

P2-A　　　TCGACGGATCCTTTTAGAGAGGAAGATTTG
　　　　　CATGTTTCATCCGATAGAAGAAGCACTGGA
　　　　　CGCTTT

P2-B　　　AAAGCGTCCAGTGCTTCTTCTATCGGATGA
　　　　　AACATGCAAATCTTCCTCTCTAAAAGGATC
　　　　　CG

P2-CII　　CGATTTTTGCATAAAGCCAATGAAAATAAG
　　　　　ACCCAACAAACCATTACAAAAGCCTTCTTA
　　　　　AGCGAAAACGGCTTTTAG

P2-DII　　AATTCTAAAAGCCGTTTTCGCTTAAGAAGG
　　　　　CTTTTGTAATGGTTTGTTGGGTCTTATTTT
　　　　　CATTGGCTTTATGCAAAAAT

FIG. 18

BACTERIAL STRAINS WHICH OVERPRODUCE RIBOFLAVIN AND METHODS OF USE THEREOF

This application is a continuation of prior U.S. application Ser. No. 09/306,615, filed May 6, 1999 now U.S. Pat. No. 6,551,813, which is a divisional of U.S. application Ser. No. 09/138,775, filed Aug. 24, 1998, now U.S. Pat. No. 5,925,538; which is a divisional of U.S. application Ser. No. 08/384,626, filed Feb. 6, 1995, now U.S. Pat. No. 5,837,528; which is a continuation of U.S. application Ser. No. 07/873,572, filed Apr. 21, 1992, now abandoned; which is a continuation of U.S. application Ser. No. 07/581,048, filed Sep. 11, 1990, now abandoned; which is a continuation-in-part of U.S. application Ser. No. 07/370,378, filed Jun. 22, 1989, now abandoned.

BACKGROUND OF THE INVENTION

Riboflavin (vitamin $B_2$) is synthesized by all plants and many microorganisms but is not produced by higher animals. Because it is a precursor to coenzymes such as flavin adenine dinucleotide and flavin mononucleotide, that are required in the enzymatic oxidation of carbohydrates, riboflavin is essential to basic metabolism. In higher animals, insufficient riboflavin can cause loss of hair, inflammation of the skin, vision deterioration, and growth failure.

Riboflavin can be commercially produced either by a complete chemical synthesis, starting with ribose, or by fermentation with the fungi *Eremothecium ashbyii* or *Ashbya gossypii* (*The Merck Index*, Windholz et al., eds., Merck & Co., p. 1183, 1983). Mutants of *Bacillus subtilis*, selected by exposure to the purine analogs azaguanine and azaxanthine, have been reported to produce riboflavin in recoverable amounts (U.S. Pat. No. 3,900,368, Enei et al., 1975). In general, exposure to purine or riboflavin analogs selects for deregulated mutants that exhibit increased riboflavin biosynthesis, because the mutations allow the microorganism to "compete out" the analog by increased production (Matsui et al., *Agric. Biol. Chem.* 46:2003, 1982). A purine-requiring mutant of *Saccharomyces cerevisiae* that produces riboflavin has also been reported (U.S. Pat. No. 4,794,081, Kawai et al., 1988). Rabinovich et al. (*Genetika* 14:1696 (1978)) report that the riboflavin operon (rib operon) of *B. subtilis* is contained within a 7 megadalton (Md) EcoRI fragment (later referred to as a 6.3 Md fragment in Chikindas et al., *Mol. Genet. Mik. Virusol.* no. 2:20 (1987)). It is reported that amplification of the rib operon may have been achieved in *E. coli* by cloning the operon into a plasmid that conferred resistance to ampicillin and exposing bacteria containing that plasmid to increasing amounts of the antibiotic. The only evidence for rib amplification is a coincident increase in the presence of a green-fluorescing substance in the medium; the authors present a number of alternative possibilities besides an actual amplification of the operon to explain the phenomenon observed.

French Patent Application No. 2,546,907, by Stepanov et al. (published Dec. 7, 1984), discloses a method for producing riboflavin that utilizes a mutant strain of *B. subtilis* which has been exposed to azaguanine and roseoflavin and that is transformed with a plasmid containing a copy of the rib operon.

Morozov et al. (*Mol. Genet. Mik. Virusol.* no. 7:42 (1984)) describe the mapping of the *B. subtilis* rib operon by assaying the ability of cloned *B. subtilis* rib fragments to complement *E. coli* riboflavin auxotrophs or to marker-rescue *B. subtilis* riboflavin auxotrophs. Based on the known functions of the *E. coli* rib genes, the following model was proposed for the *B. subtilis* operon: ribG (encoding a deaminase)—ribO (the control element)—ribB (a synthetase)—ribF—ribA (a GTP-cyclohydrolase)—ribT/D (a reductase and an isomerase, respectively)—ribH (a synthetase).

Morozov et al. (*Mol. Genet. Mik. Virusol.* no. 11:11 (1984)) describe the use of plasmids containing the *B. subtilis* rib operon with either wild-type (ribO$^+$) or constitutive (ribO 335) operator regions to assay their ability to complement *B. subtilis* riboflavin auxotrophs. From the results, a revised model of the rib operon was proposed, with ribO now located upstream of all of the structural genes, including ribG, and with the existence of an additional operator hypothesized, possibly located just upstream of ribA.

Morozov et al. (*Mol. Genet. Mik. Virusol.* no. 12:14 (1985)) report that the *B. subtilis* rib operon contains a total of three different promoters (in addition to a fourth "promoter" that is only active in *E. coli*). The primary promoter of the operon was reported to be located within the ribO region, with the two secondary promoters reported between the ribB and ribF genes and within the region of the ribTD and ribH genes, respectively.

Chikindas et al. (*Mol. Genet. Mik. Virusol.* no. 2:20 (1987)) propose a restriction enzyme map for a 6.3 Md DNA fragment that contains the rib operon of *B. subtilis*. Sites are indicated for the enzymes EcoRI, PstI, SalI, EcoRV, PvuII and HindIII.

Chikindas et al. (*Mol. Genet. Mik. Virusol.* no. 4:22 (1987) report that all of the structural genes of the *B. subtilis* rib operon are located on a 2.8 Md BglII-HindIII fragment and that the BglII site is located between the primary promoter of the operon and the ribosomal-binding site of its first structural gene. As described infra, Applicants show that this BglII site is actually located within the most-5' open reading frame of the rib operon, so that the 2.8 Md fragment described does not contain all of the rib structural genes. Thus, in contrast to the report of Chikindas et al., the 1.3 Md BglII fragment does not contain the ribosomal-binding site of the first structural gene; insertions at this site lead to a riboflavin-negative phenotype. Consequently, any attempt to use this BglII site to engineer the rib operon in order to increase expression, for example by replacing the 5' regulatory region with a stronger promoter, would actually destroy the integrity of the first structural gene and thus the operon as well.

Chikindas et al. (*Dokl. Akad. Nauk.* 5 SSSR 298:997 (1988)) disclose another model of the *B. subtilis* rib operon, containing the primary promoter, $p_1$, and two minor promoters, $P_2$ and $p_3$: ribO($p_1$)-ribG-ribB-$p_2$-ribF-ribA-ribT-ribD-$p_3$-ribH. As before, it is incorrectly reported that the 1.3 Md BglII fragment contains the entire first structural gene of the operon and that this proximal BglII site maps within the primary regulatory region.

SUMMARY OF THE INVENTION

The present invention relates (inter alia) to recombinant bacteria useful in riboflavin production. The invention also involves the nucleotide sequence of the rib operon and its open reading frames, and recombinant bacteria that contain the rib operon. Additionally, the invention involves bacteria that have been mutated so that their production of riboflavin and/or purines is deregulated, and to bacteria which have copies of the rib operon inserted and amplified within their chromosomal DNA. In one embodiment, the rib operon itself can be deregulated by replacing its control regions with sequences that allow constitutive or unregulated expression. The bacteria, operons and sequences of this invention can be used to produce large amounts of riboflavin by fermentation. Finally, this invention involves the production of large quantities (over 10 g/l) of riboflavin by construction of various bacterial strains and growth of those bacterial strains within a medium and under conditions suitable for production of the riboflavin.

The present invention is illustrated by way of specific examples detailed below, one of which includes a mutant of B. subtilis 1A382, RB50::[pRF8]$_{60}$(Ade$^+$), that is deregulated for riboflavin and purine production and has the rib operon amplified within its chromosome. This mutant is able to produce greater than 5 g/l of riboflavin after 48 hours of fermentation in a 14-liter vessel. Other bacteria are described in which riboflavin production is increased to over 10 g/l under similar conditions.

The invention specifically includes the following aspects.

A first aspect of the invention features a recombinant bacterium which includes at least one copy of an exogenously introduced nucleic acid within its chromosome. This nucleic acid encodes one or more riboflavin biosynthetic proteins, is heritable, and is capable of expression by the bacterium such that riboflavin biosynthesis by the bacterium is increased relative to a bacterium lacking such a sequence.

By "recombinant bacterium" is meant a bacterium which contains one or more nucleic acid sequences, from the same or another organism, at a site at which those sequences do not naturally occur, or in a copy number in which they do not naturally occur. Thus, not only does the term include bacteria containing heterologous DNA sequences, it also includes those bacteria in which two copies of a nucleic acid sequence, e.g., a gene or an operon, are provided at a site which normally includes only one copy of the sequence; and it includes bacteria in which one or more copies of a nucleic acid sequence are introduced at a site which does not normally include that sequence. Such recombinant bacteria are constructed by standard recombinant DNA technology.

By "exogenously introduced" is meant that the nucleic acid is introduced into the chromosome from a source outside of that chromosome by any standard technique, including recombinant DNA technology, transformation, and transfection. It also includes the progeny of such bacteria, for example, those bacteria produced by cellular division of an originally constructed, transformed, or transfected bacterium.

By "riboflavin biosynthetic proteins" is meant to include those peptides, polypeptides or proteins which are directly involved in the synthesis of riboflavin from guanosine triphosphate. These proteins may be identical to those which naturally occur within a bacterium and are involved in the synthesis of riboflavin within that bacterium. Alternatively, they may be modifications of such proteins, for example, they may contain modifications which do not significantly affect the biological activity of the protein. For example, the natural protein may be modified by introducing or substituting one or more amino acids, preferably by conservative amino acid substitution, or by removing nonessential regions of the protein. Such modifications are readily performed by standard techniques.

In some embodiments, the bacterium contains two or more copies of the nucleic acid sequence; and the nucleic acid encoding one or more of the riboflavin biosynthetic proteins is present at at least two sites within the chromosome of the bacterium.

By "site" is meant a distinct chromosomal location relative to a wild-type bacterium at which the nucleic acid encoding the biosynthetic proteins is located. For example, such nucleic acid may be located at the naturally occurring site for genes encoding such proteins (i.e., at a rib locus), or it may be located at a site distant from this location. Preferably such distant sites are chosen from regions of chromosomal nucleic acid which are not essential to the recombinant bacterium, such as regions which encode proteins which are not essential to production of riboflavin. Examples of such regions include those which encode certain extracellular enzymes such as proteases. Insertion at such sites does not interfere with a desirable quality or trait. Any site is suitable as long as the functioning of the bacterium, with regard to riboflavin production, is not substantially affected.

In other embodiments, the nucleic acid is present in a plurality of copies at one or more of the sites; and the nucleic acid is present at at least three sites within the chromosome. By introducing the nucleic acid at different sites, the total number of copies of the nucleic acid within the chromosome can be increased. Increasing the copy number, increases the amount of riboflavin production.

Generally the riboflavin biosynthetic proteins are encoded by one or more rib genes (e.g., an inactivation of which creates a riboflavin auxotroph), preferably at least five distinct rib genes identifiable from the nucleotide sequence provided in FIG. 3. Preferably, at least five copies of such genes are provided. By "rib genes" is meant those genes or portions of genes which encode proteins which occur naturally within an organism, or perform a similar function to such proteins, which are involved in the biosynthetic conversion of guanosine triphosphate to riboflavin within a bacterium.

Figure 4:
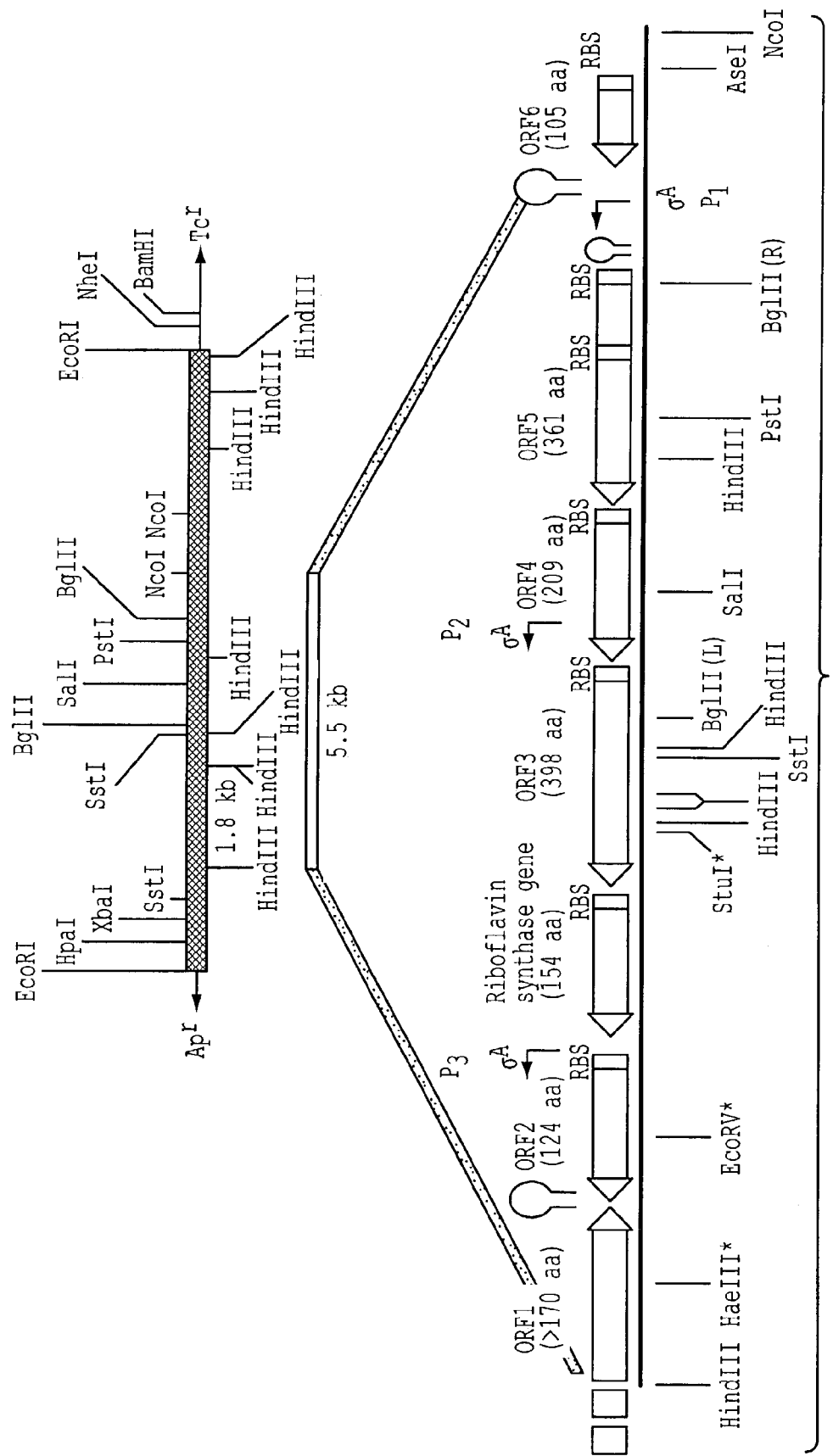

In a related aspect, the invention features a recombinant bacterium which includes nucleic acid encoding one or more riboflavin biosynthetic proteins, e.g., the gene products identified in FIG. 4, β subunit riboflavin synthetase gene, ORF's 2, 3, 4 and 5, the expression of at least one of which is controlled by a transcription element not naturally associated with the nucleic acid. Alternatively, the recombinant bacterium includes one or more rib genes or transcription units the expression of which is controlled by a transcription element not naturally associated with that rib gene.

By "transcription element" is meant to include any nucleic acid which effects (i.e., turns on) the transcription of nucleic acid downstream from that transcription element. Examples of such elements include promoters and operators. Such transcription elements are not naturally associated with the nucleic acid, for example, they may be heterologous transcription elements. That is, they may be isolated from other species or genera of bacteria or other organisms. Alternatively, the transcription element may be one naturally present in the bacterium but not normally associated with a rib gene to which it is now transcriptionally linked. Such elements do not include those which are naturally associated with a rib gene.

In other embodiments, the recombinant bacterium includes at least three (or at least five) rib genes and the expression of all three rib genes is controlled by a transcription element not naturally associated with those rib genes; at least two transcription elements are provided; the rib genes are provided within the chromosome of the recombinant bacterium; the recombinant bacterium is deregulated for riboflavin gene expression; and the transcription element is a promoter. For example, the promoter is a constitutive, growth-regulated, or inducible promoter, such as one associated with the SPO1 phage, and/or veg, amy, and sacQ-sensitive promoters, e.g., apr.

By "deregulated" is meant that the level of riboflavin production is greater than that observed in a bacterium with natural riboflavin regulatory systems (i.e., a wild type bacterium). Examples of such deregulated bacteria include those which are resistant to various purine analogs or antagonists, or riboflavin analogs.

In other specific embodiments, at least one of the rib genes includes a ribosome binding site not naturally associated with the rib gene; the rib genes are present at two sites within the chromosome; and the rib genes are, present in a plurality of copies within the chromosome. In more preferred embodiments, the rib genes are *Bacillus* rib genes, for example ORF3 and ORF5 shown in FIG. 4, and the transcription element is located in a region 5'-upstream of ORF3 or ORF5; and the rib genes are chosen from a β-riboflavin synthase-encoding gene, ORF2, ORF3, ORF4, and ORF5; and the bacterium belongs to a species of Esherichia, e.g., *E. coli*, Bacillus, e.g., *B. subtilis*, *Klebsiella*, or *Cornyebacterium*.

In another related aspect, the invention features nucleic acid, which includes five or more rib genes, the expression of which is controlled by a transcription element not naturally associated with that rib gene.

In another aspect, the invention features a method for production of riboflavin. The method includes growing cells which are able to produce riboflavin under aerobic conditions with the level of dissolved oxygen maintained at a concentration between 5 and 30%. The method further includes limiting the growth of the cells by limiting the availability of a component in the growth medium such that the dissolved oxygen concentration is maintained at that level.

In this method the growth of cells is maintained at a level which prevents the growth conditions becoming anaerobic. Under anaerobic conditions the synthesis of riboflavin is reduced. In some embodiments, the limiting component is chosen from a carbon source, nitrogen source, or a component required by the cells (e.g., in the feed medium). For example, if the cells are auxotrophic, for example, for methionine, a limiting level of methionine may be provided in the growth medium. In another example, the limiting component is a carbon source such as glucose or a citric acid cycle acid. Exemplary citric acid cycle acids are citric acid or succinic acid.

In a related aspect, the invention features another method for increasing production of riboflavin by a bacterium. In this method, the strain of bacterium used is deregulated for riboflavin production. More than one copy of a nucleic sequence encoding one or more riboflavin biosynthetic proteins is introduced into the chromosomal DNA of this bacterium. Preferably the bacterium used in this method is selected from one of those described above.

In other aspects of the invention, purified nucleic acid and the recombinant polypeptide product of such nucleic acid is provided. Generally, the purified nucleic acid consists essentially of all or a portion of the rib operon, for example, the specific open reading frames shown in FIG. 3. Such purified nucleic acid may be provided within a vector such as a plasmid, phage, or cosmid, or may be integrated within the chromosome of a bacterium. This nucleic acid is separated from nucleic acid with which it is naturally linked. For example, 6.5 kb of the nucleic acid encoding the whole rib operon may be inserted within a *Bacillus subtilis* chromosome at a site distant from that site in which the 6.5 kb DNA is normally present. By recombinant polypeptide is meant biologically active protein free of extraneous polypeptide (i.e., not fused to a heterologous polypeptide) having an enzymatic activity equivalent to such a naturally produced polypeptide.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1. The riboflavin biosynthetic pathway, modified from Keller et al., *Biochem.* 27:1117 (1988). The corresponding intermediates shown are those produced by *E. coli* (which are presumably the same as those produced by *B. subtilis*): structure 1, guanosine triphosphate (GTP); structure 2,2,5-diamino-6-(ribosylamino)-4(3H)-pyrimidinone-5'-phosphate; structure 3,5-amino-6-(ribosylamino)-2,4(1H,3H)-pyrimidinedione-5'-phosphate; structure 4,5-amino-6-(ribitylamino)-2,4(1H,3H)-pyrimidinedione-5'-phosphate; structure 5,6,7-dimethyl-8-ribityllumazine; structure 6, riboflavin. The biosynthetic enzymes indicated are those encoded by *B. subtilis* (GTP cyclohydrolase, α and β subunits of riboflavin synthase) or those proposed to be encoded by *B. subtilis* (a rib-specific deaminase, and a rib-specific reductase).

Figure 2:
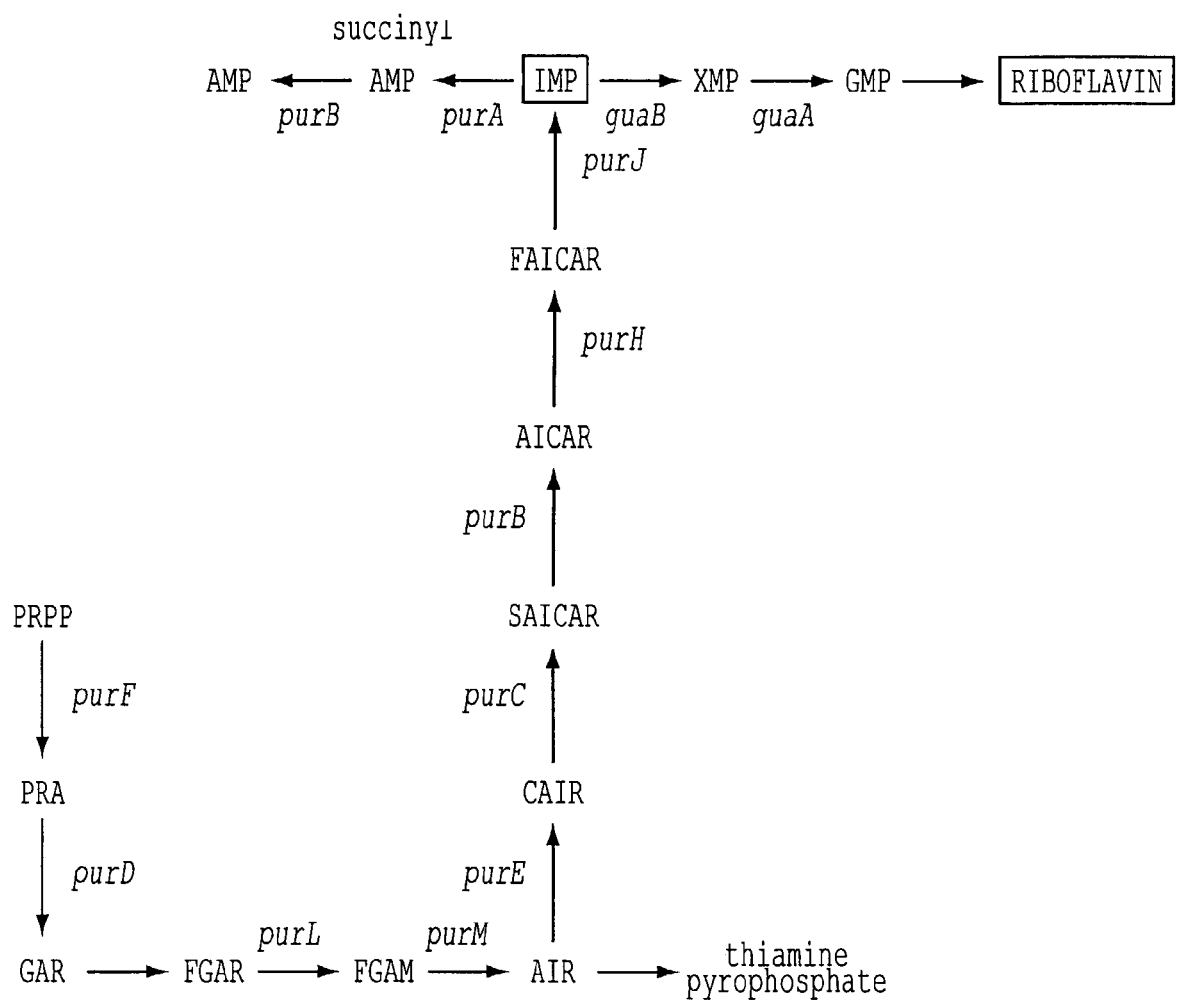

FIG. 2. Schematic representation of purine biosynthesis. The purine biosynthetic pathway, including the portion responsible for riboflavin biosynthesis, is depicted. The individual enzymes of the pathway are identified by their gene symbols (*E. coli* nomenclature). Abbreviations are as follows: PRPP, phosphoribosylpyrophosphate; GAR, glycinamide ribonucleotide; pur, GAR formyltransferase; PRA, phosphoribosylamine; purA, adenylosuccinate synthetase; purB, adenylosuccinate synthetase; FGAR, formyiglycinamide ribonucleotide; SAICAR, aminoimidazolesuccinocarboxamide ribonucleotide; purC, SAICAR synthetase; FGAM, formylglycinamidine ribonucleotide; purD, GAR synthetase; AIR, aminoimidazole ribonucleotide; purE, AIR carboxylase; CAIR, carboxyaminoimidazole ribonucleotide; purF, PRPP amidotransferase; AICAR, aminoimidazolecarboxamide ribonucleotide; purH, AICAR formyltransferase; purJ, inosine monophosphate (IMP) cyclohydrolase; FAICAR, formamidoimidazolecarboxamide ribonucleotide; purL, FGAR amidotransferase: guaA, guanosine monophosphate (GMP) synthetase; purM, AIR synthetase; guaB, IMP dehydrogenase.

Figure 3A:
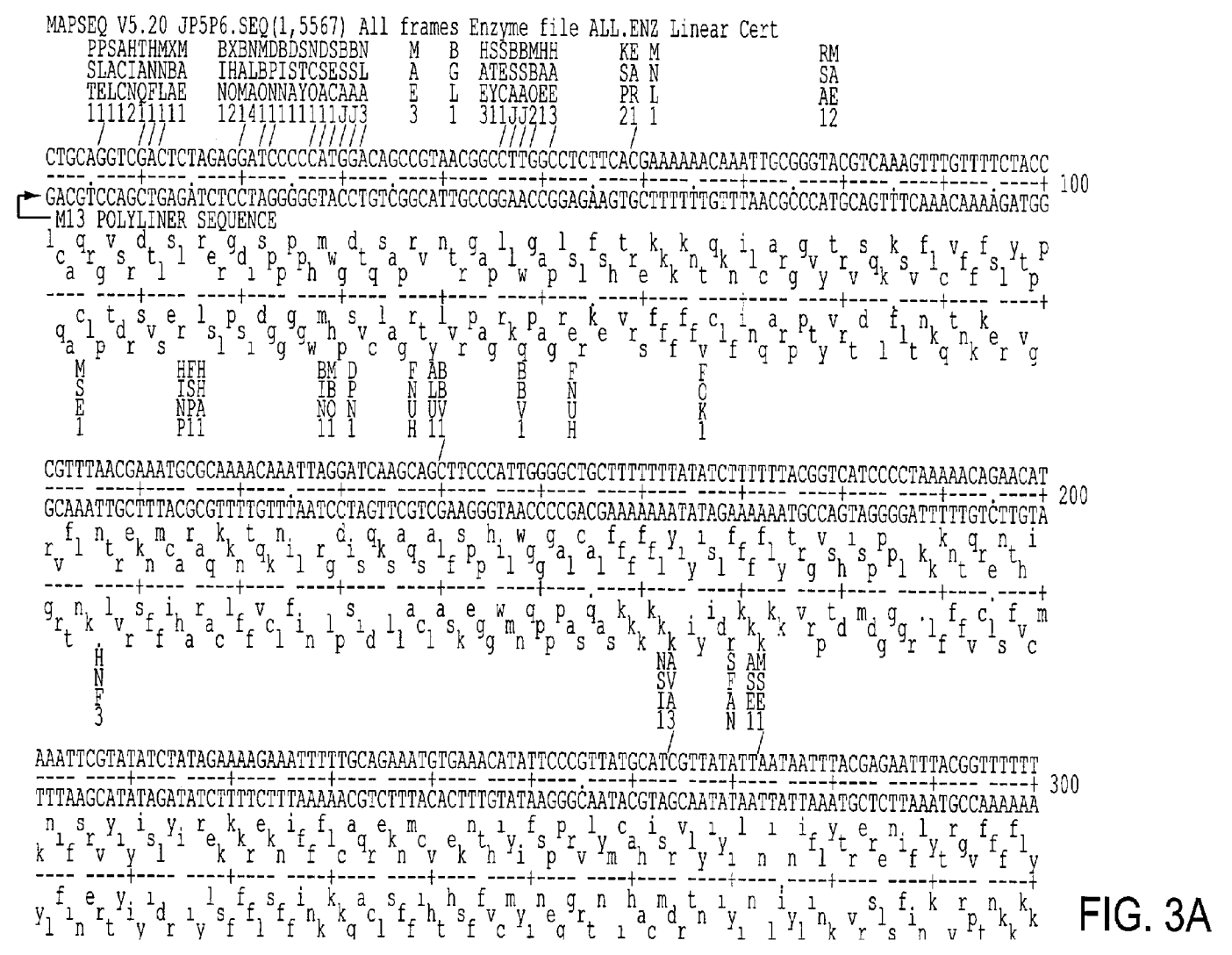
Figure 3B:
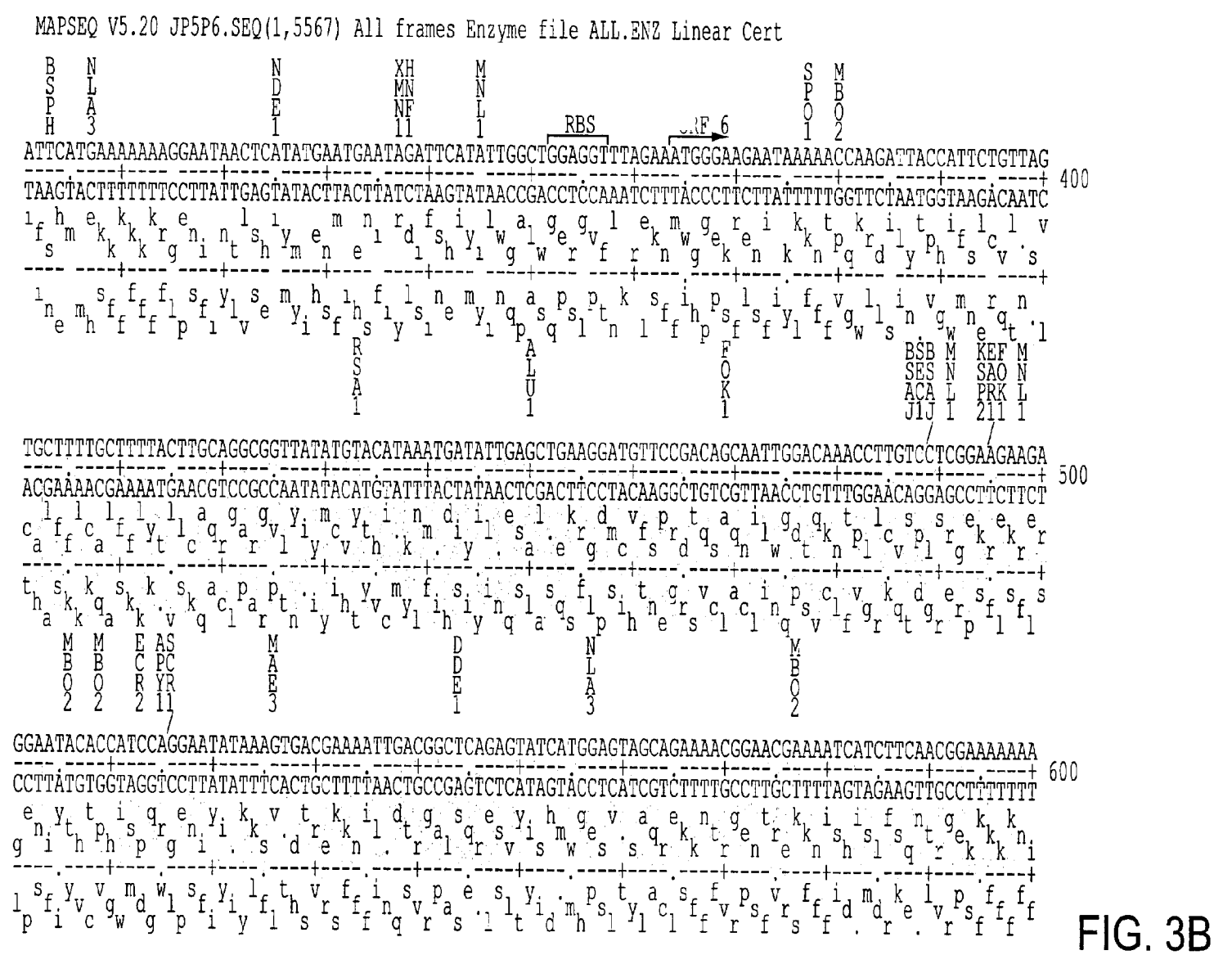
Figure 3C:
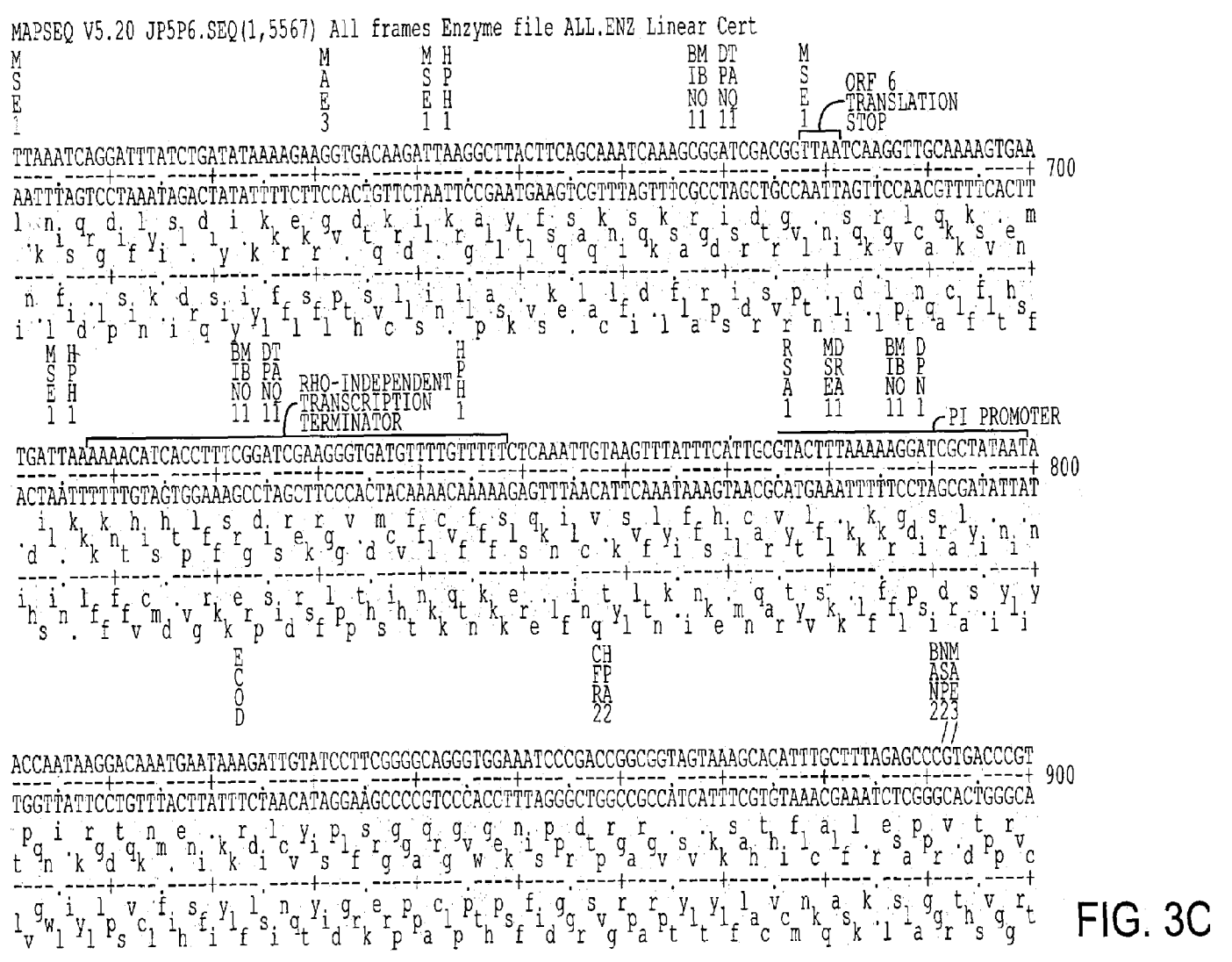
Figure 3D:
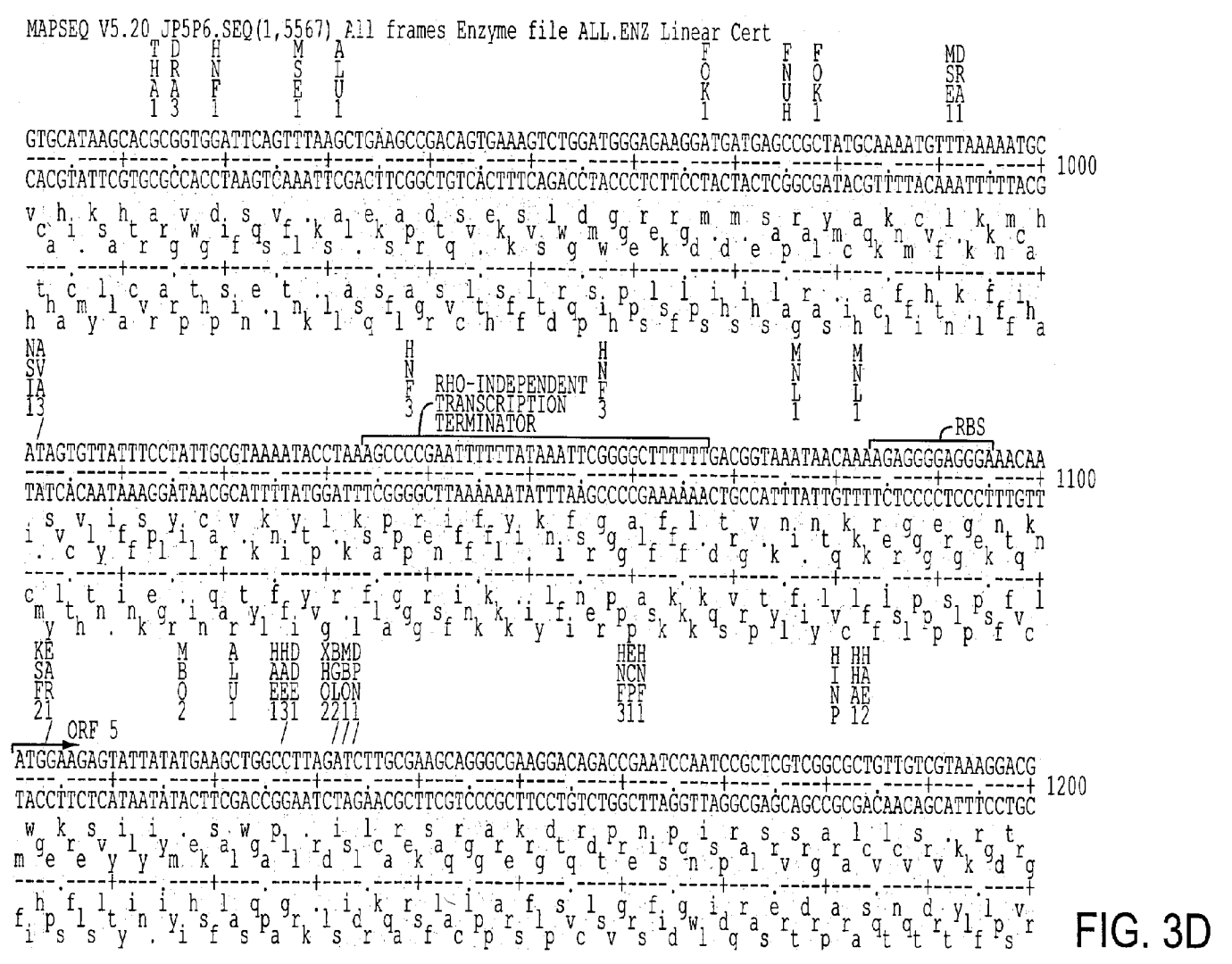
Figure 3E:
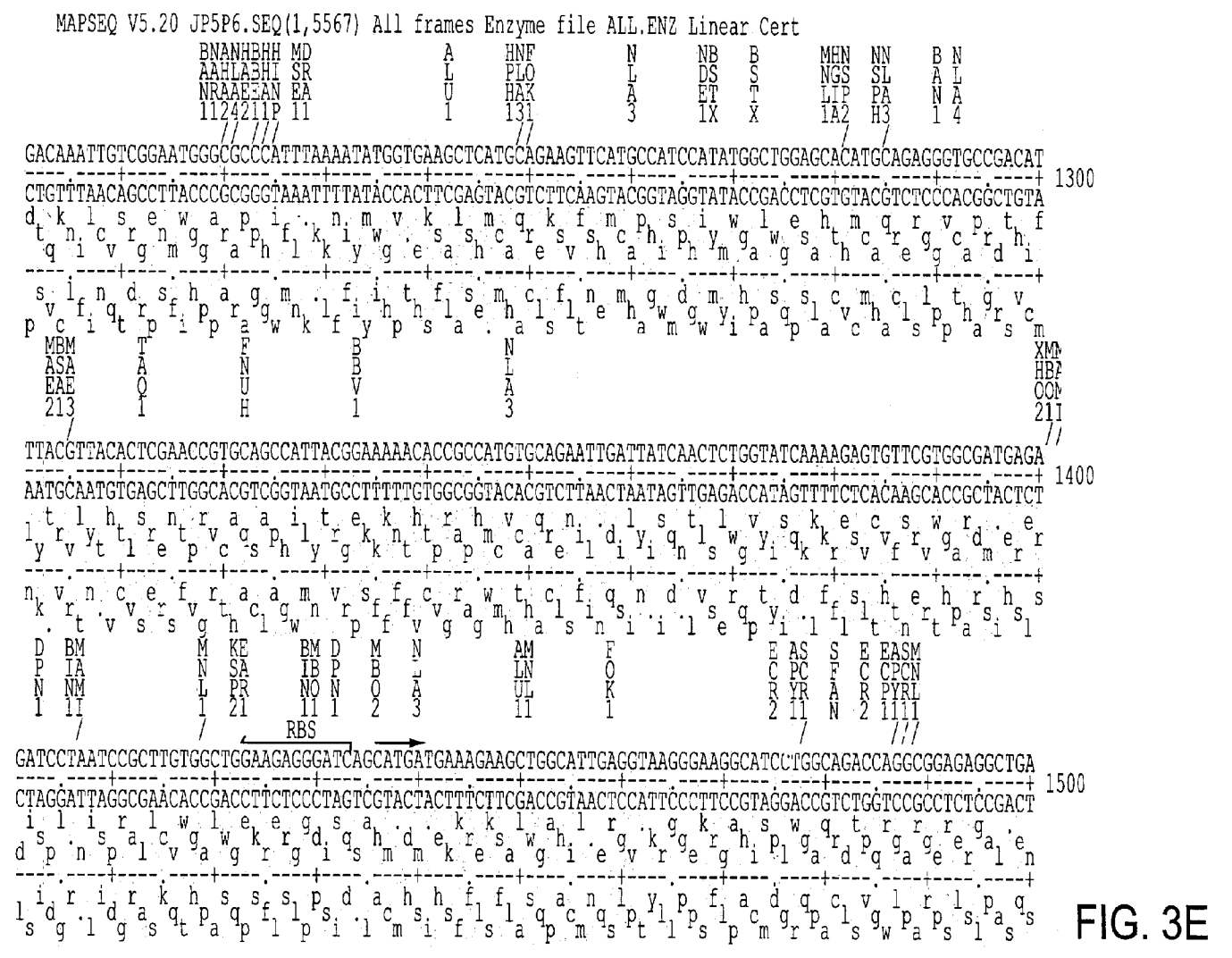
Figure 3F:
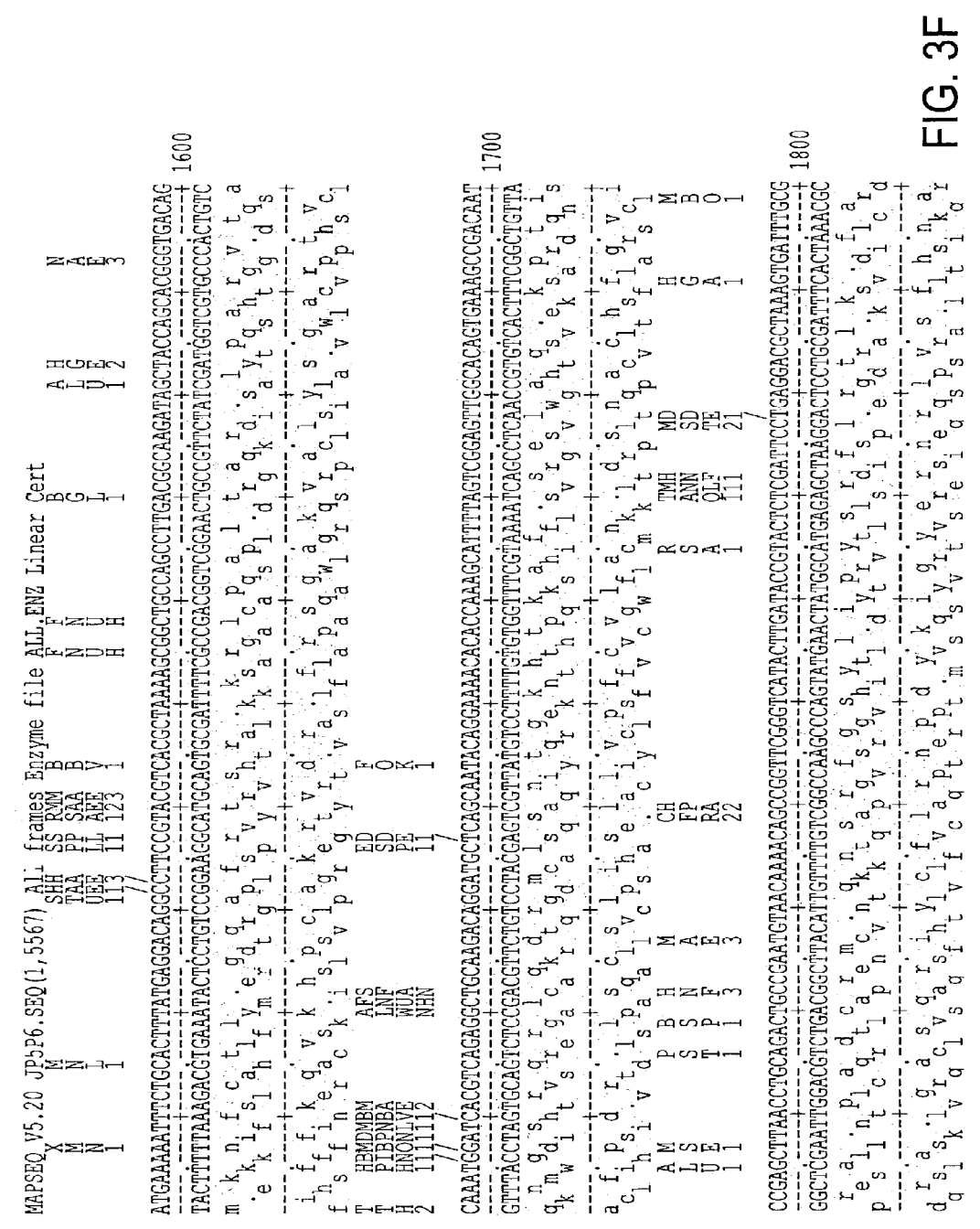
Figure 3G:
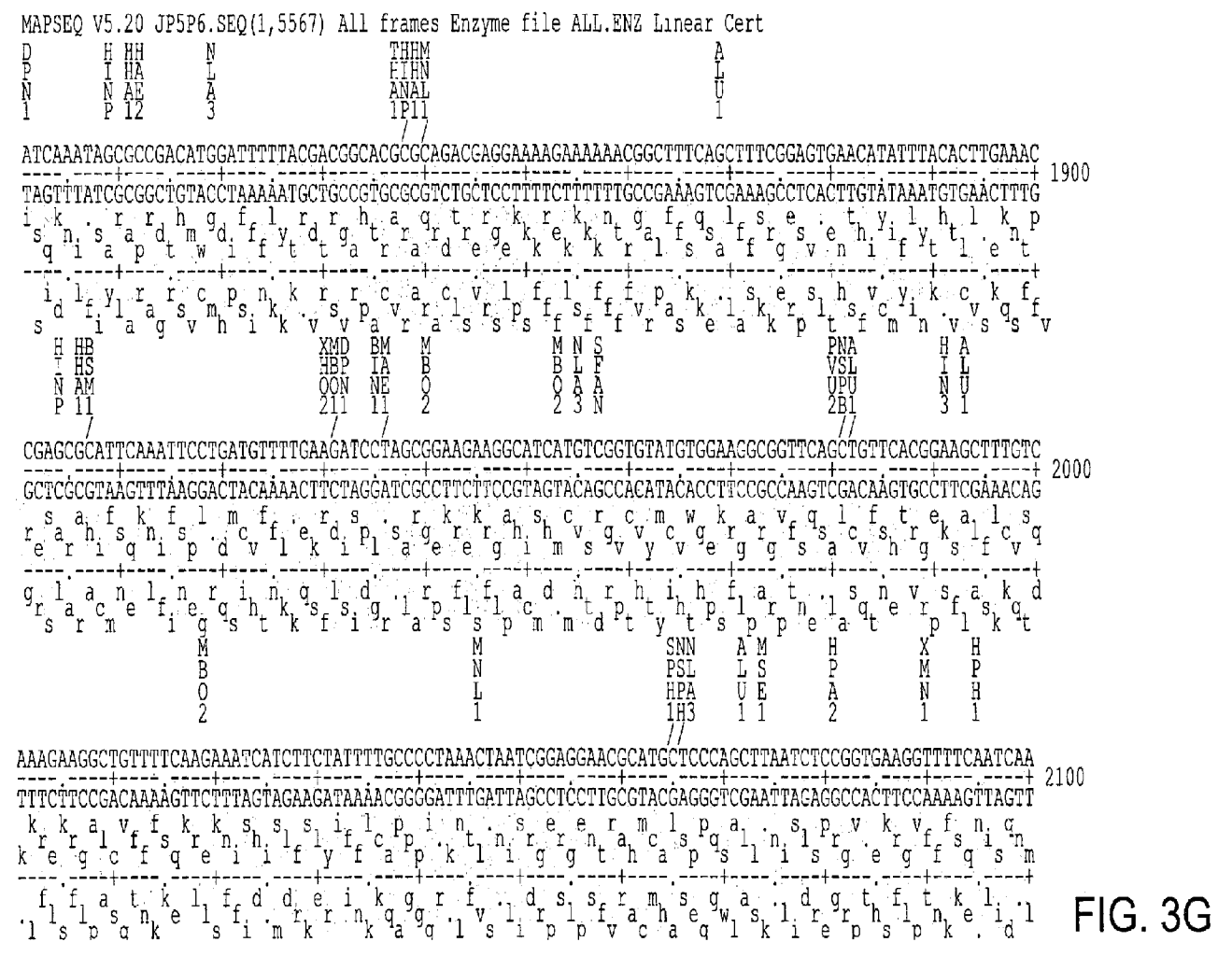
Figure 3H:
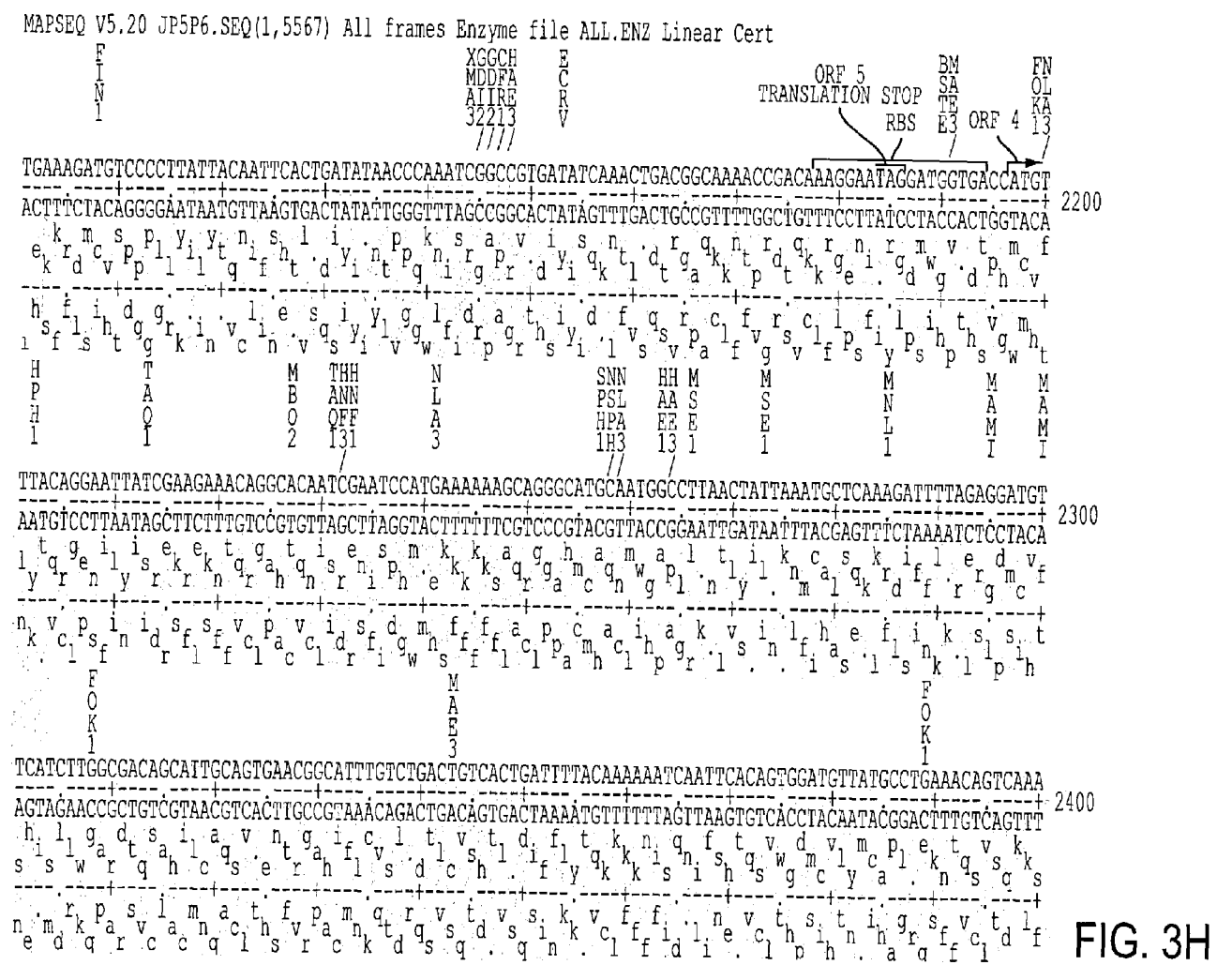
Figure 3J:
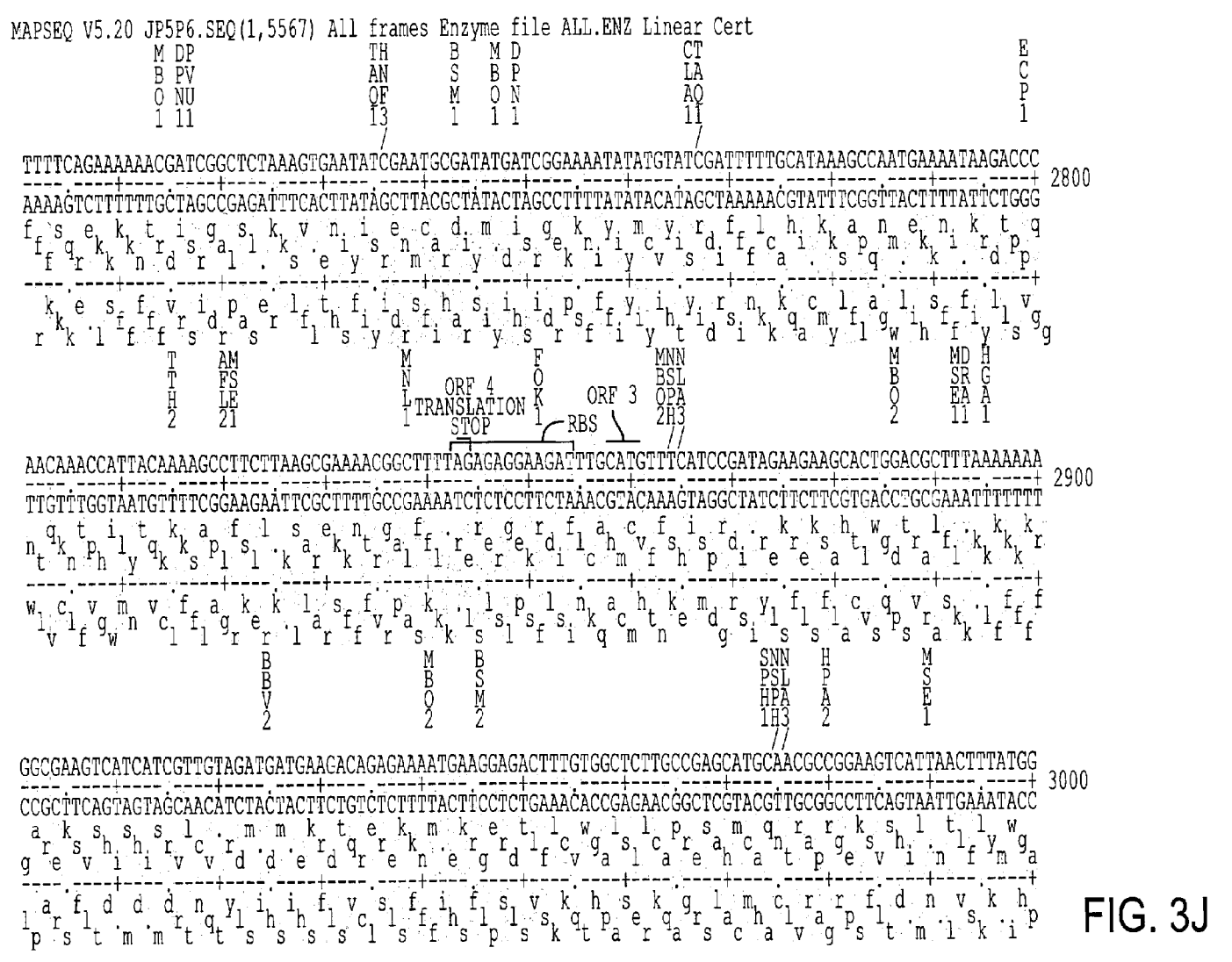
Figure 3K:
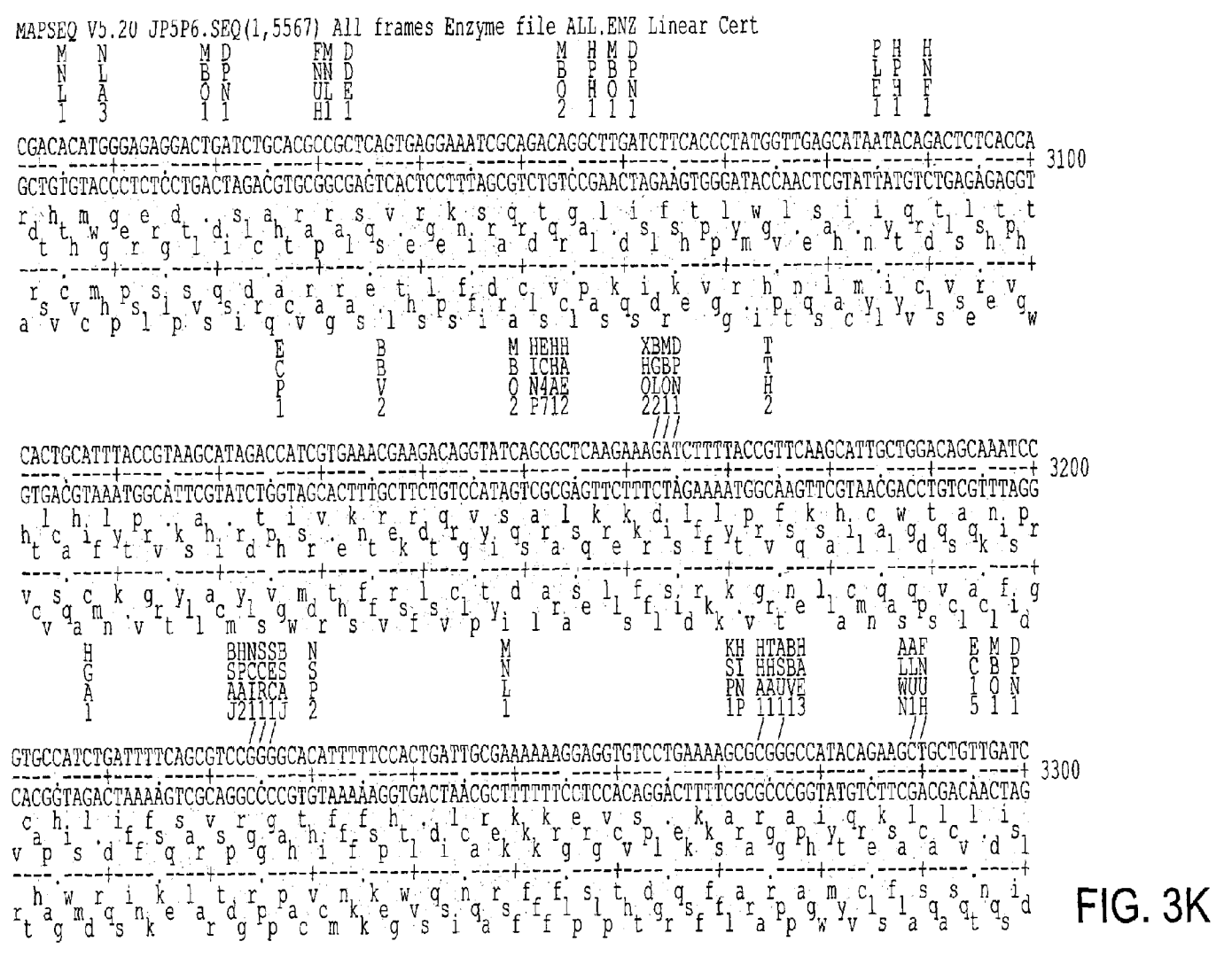
Figure 3L:
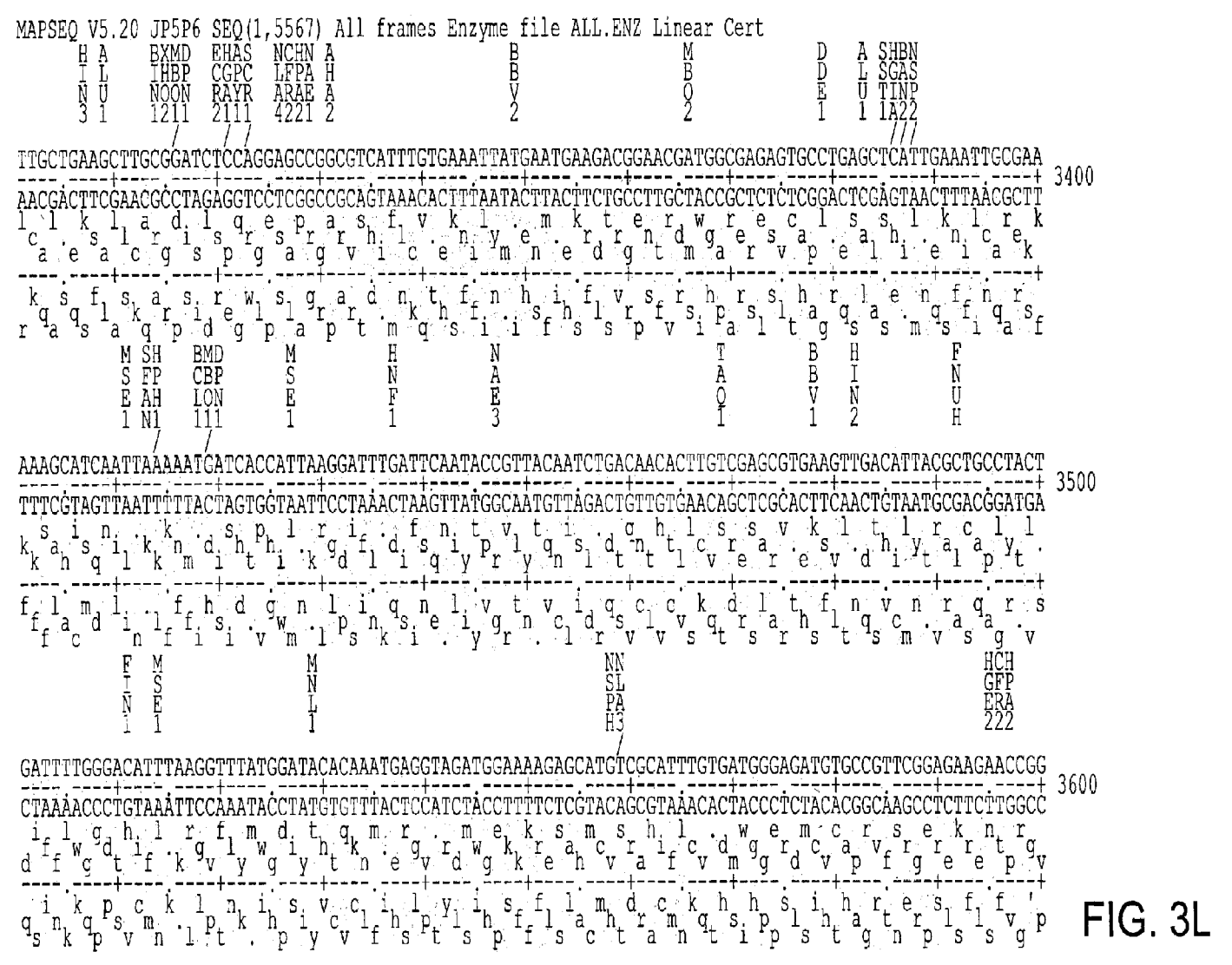
Figure 3M:
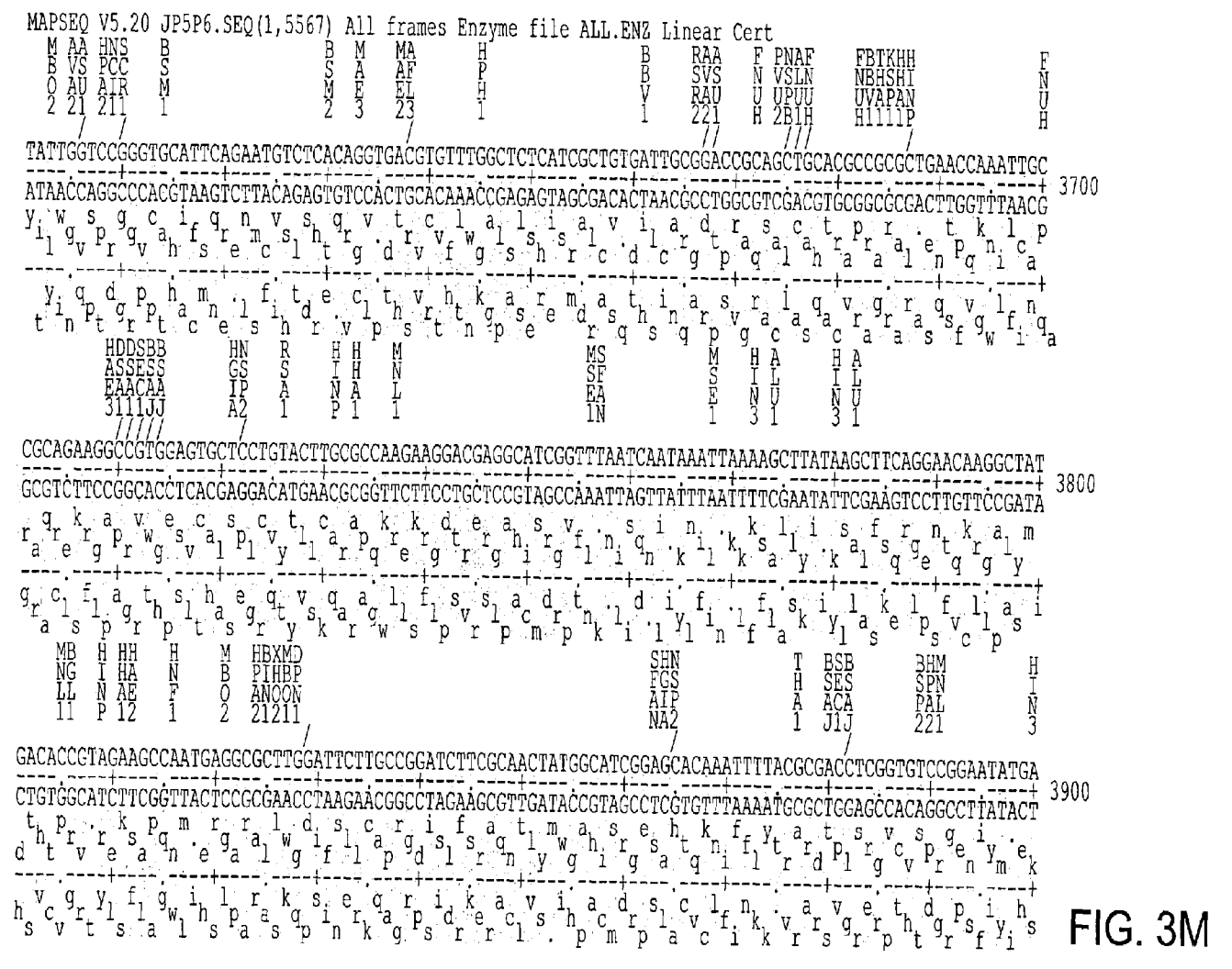
Figure 3N:
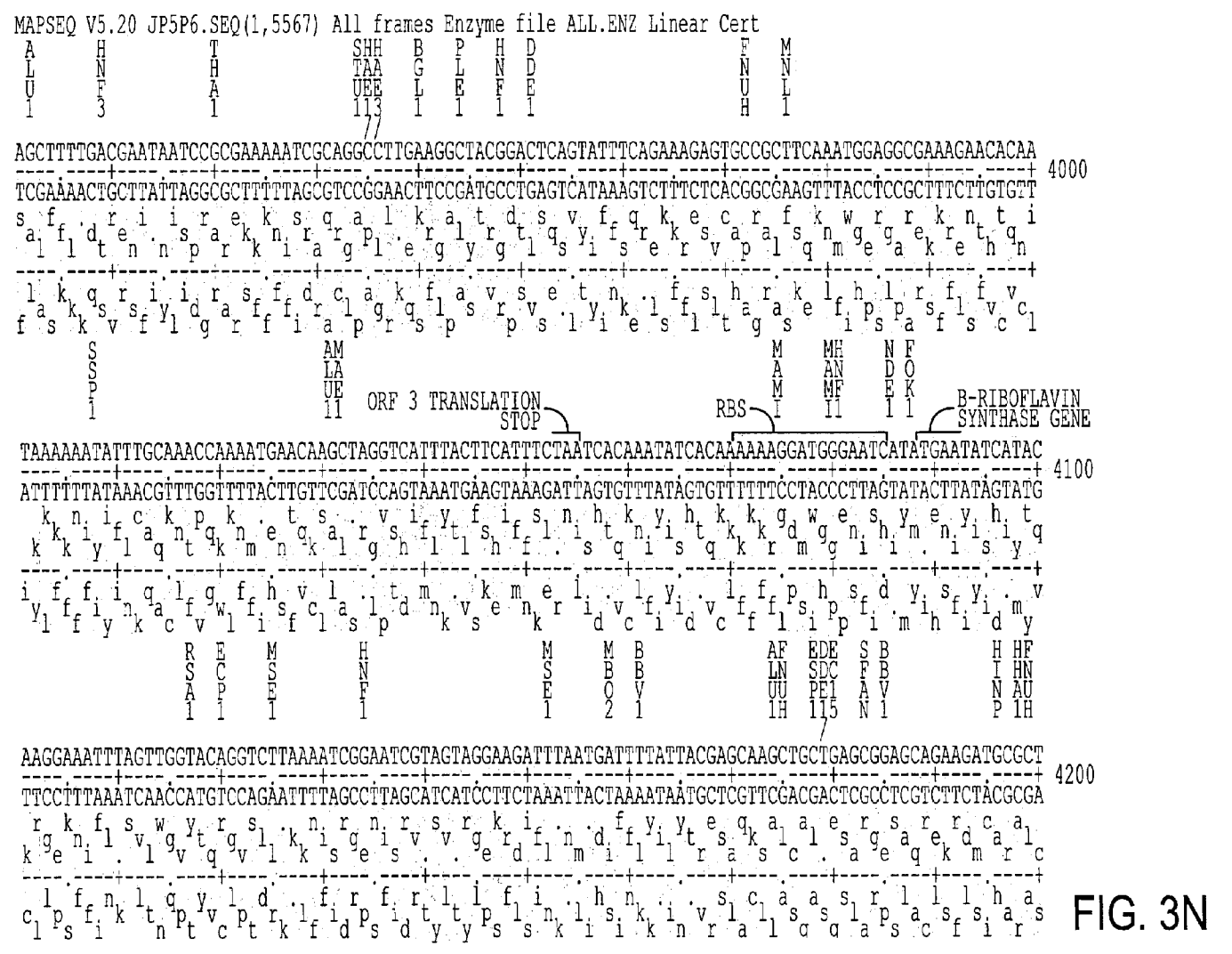
Figure 3P:
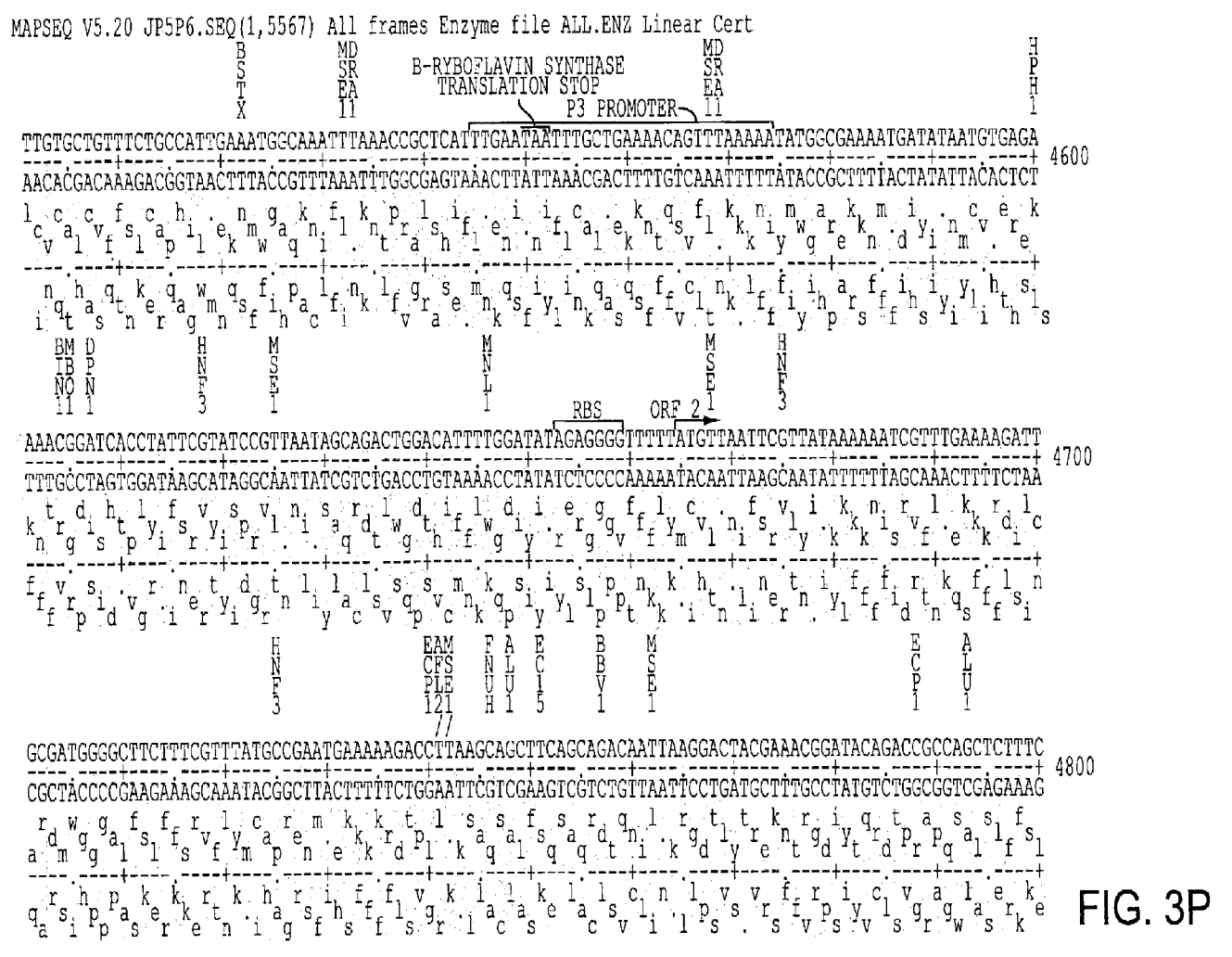
Figure 3Q:
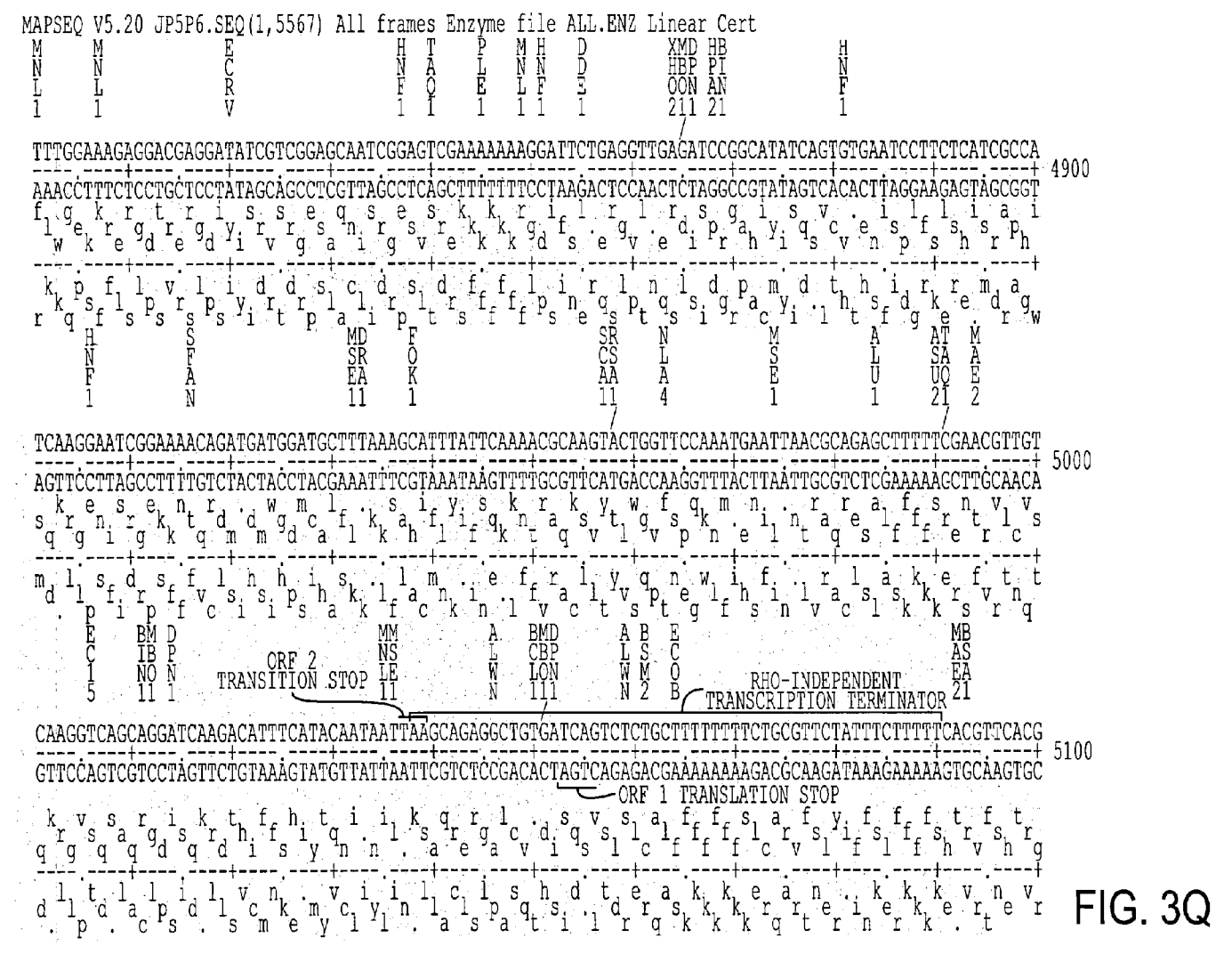
Figure 3R:
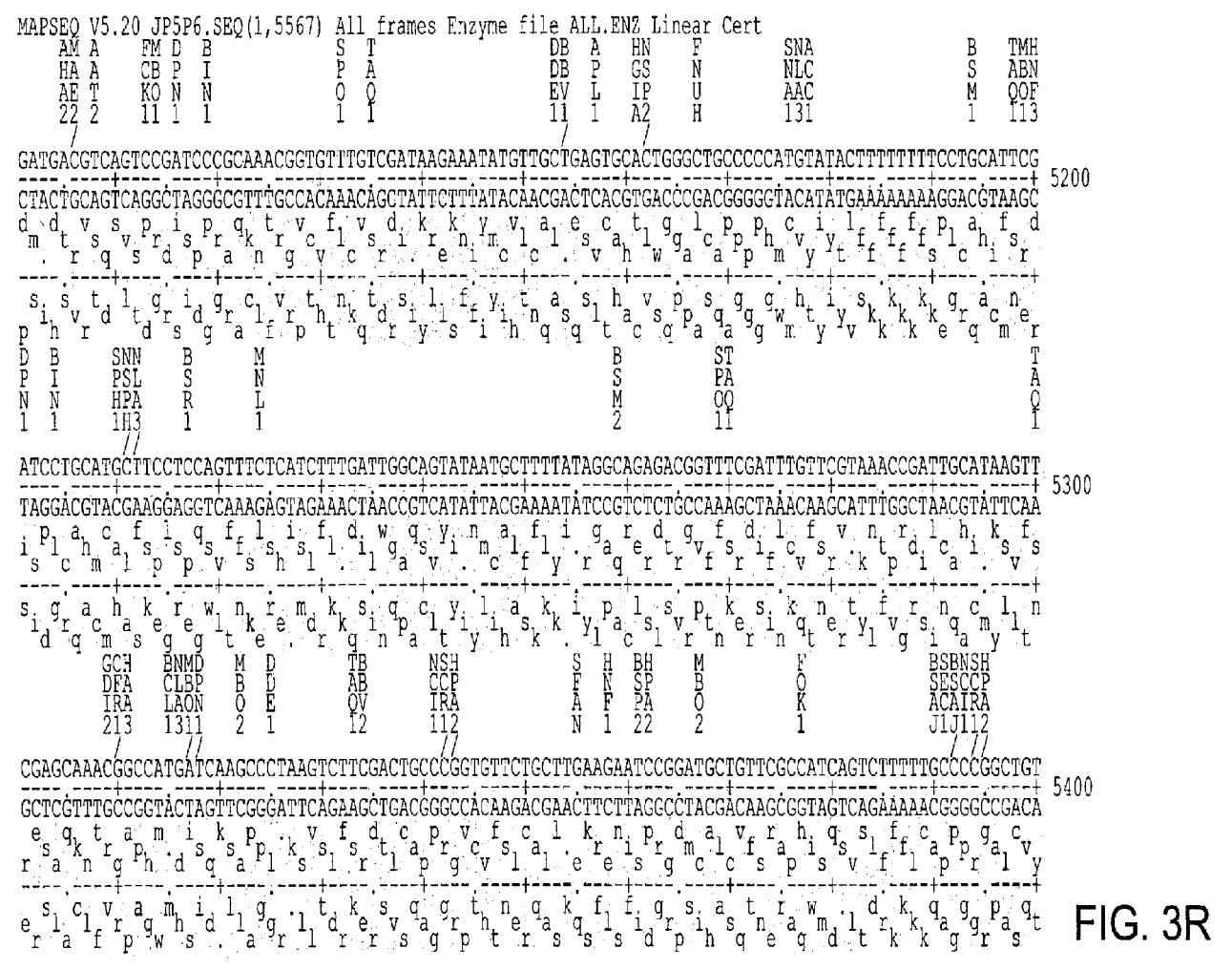
Figure 3S:
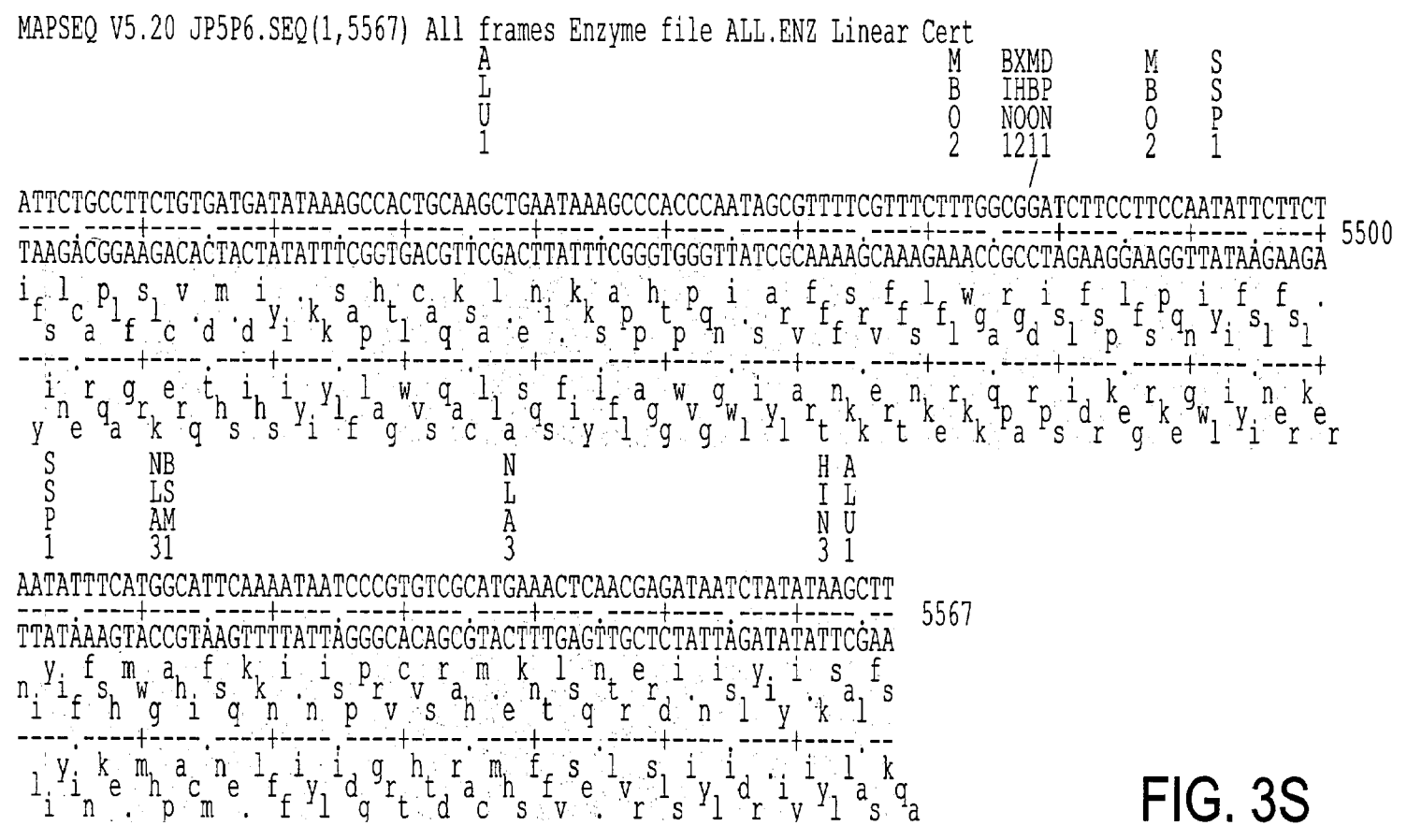

FIG. 3. The complete nucleotide and deduced amino acid sequences of the *B. subtilis* rib operon. The nucleotide sequence was determined by dideoxy sequencing of M13 clones (top strand: SEQ ID NO: 1, bottom strand: SEQ ID NO: 2). The deduced amino acid sequences are indicated by the one letter code (SEQ ID NOs: 3–8) (Lehninger, *Biochemistry,* 2d Ed., Worth Publishers, Inc., New York, p. 72).

FIG. 4. A schematic representation of the rib gene cluster. The top diagram is the restriction endonuclease map of the cloned 10 kb EcoRI DNA fragment in plasmid pRF2, containing the *B. subtilis* rib operon. The hatched box depicts Rib+ cloned DNA, while the thin black line represents pBR322 DNA. The bottom diagram is based on the complete nucleotide sequence of the 6.0 kb fragment to which the rib operon was localized. Open reading frames are depicted by open boxes, with arrows indicating the direction of transcription, and closed boxes indicating the putative ribosome binding sites. Probable $\sigma^A$ promoter regions are shown. Tentatively; identified rho-independent transcription termination sites are indicated by a "hairpin" symbol. Not all restriction sites are indicated.

Figure 5:
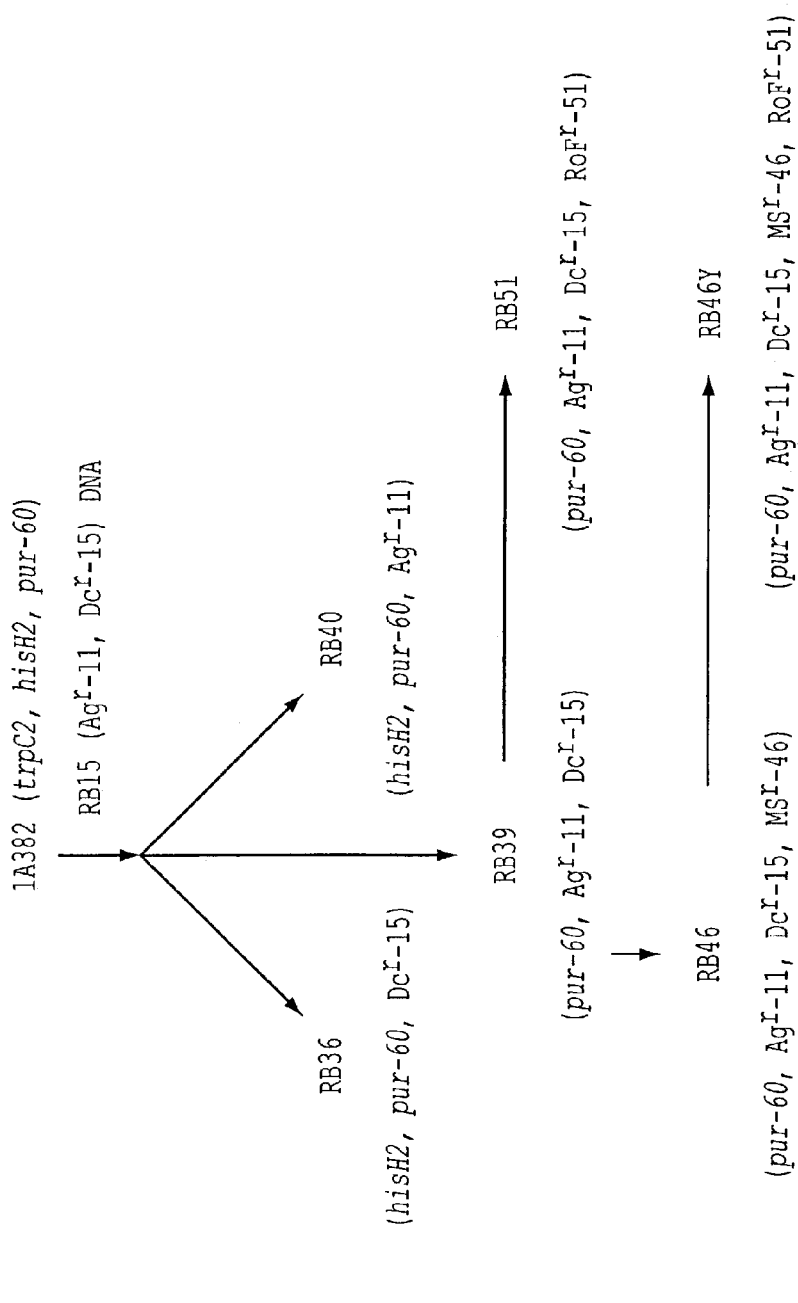

FIG. 5. Strain lineage of RB50. The lineage of the riboflavin overproducing strain of *B. subtilis*, RB50, is depicted. The various parent strains were exposed to riboflavin and purine analogs to select appropriate mutations.

Figure 6:
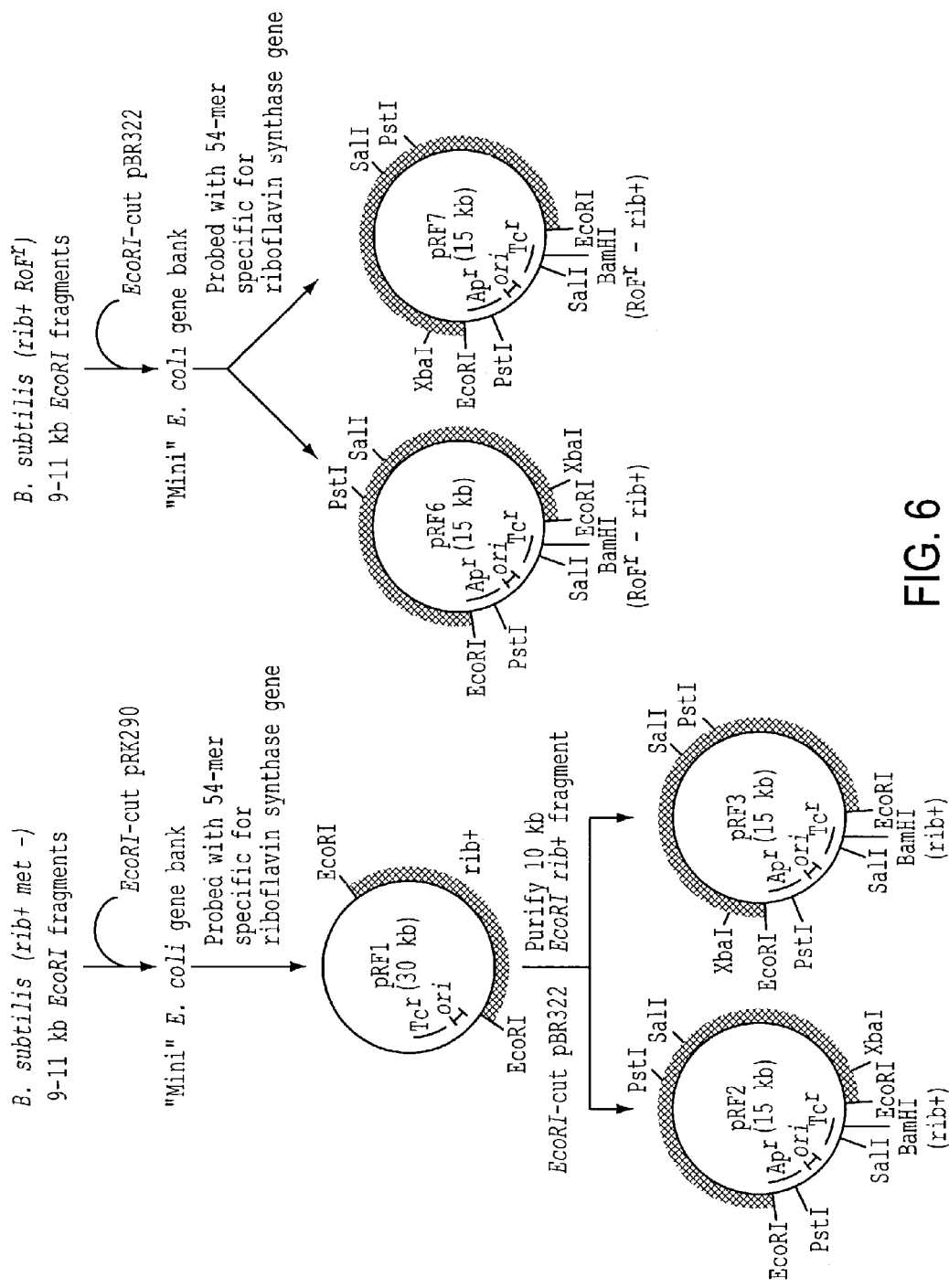

FIG. 6. Origins of rib$^+$ recombinant plasmids. A schematic diagram of the production of the rib operon-containing recombinant plasmids pRF1, pRF2, pRF3, pRF6 and pRF7 is presented. A library of size-selected, 9–11 kb fragments of *B. subtilis* DNA was used to produce a gene library in *E. coli* plasmid vectors. Clones were selected by hybridization to the 54-mer probe specific for the β subunit of the riboflavin synthase gene.

Figure 7:
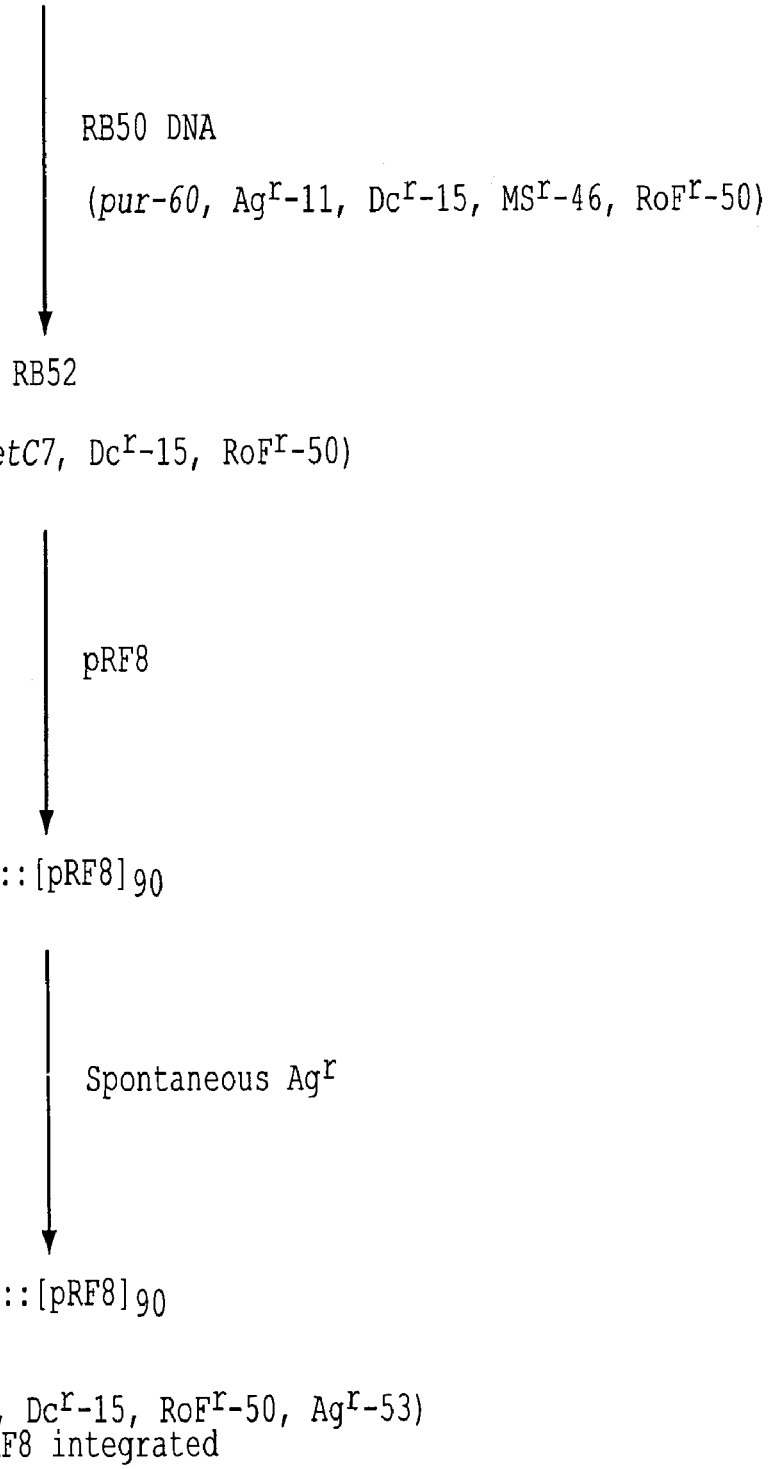

FIG. 7. The strain lineage of *B. subtilis* RB53::[pRF8]$_{90}$. Plasmid pRF8 was integrated into the chromosome of the intermediate strain RB52 and amplified; the resulting strain was exposed to the purine analog azaguanine.

Figure 8:
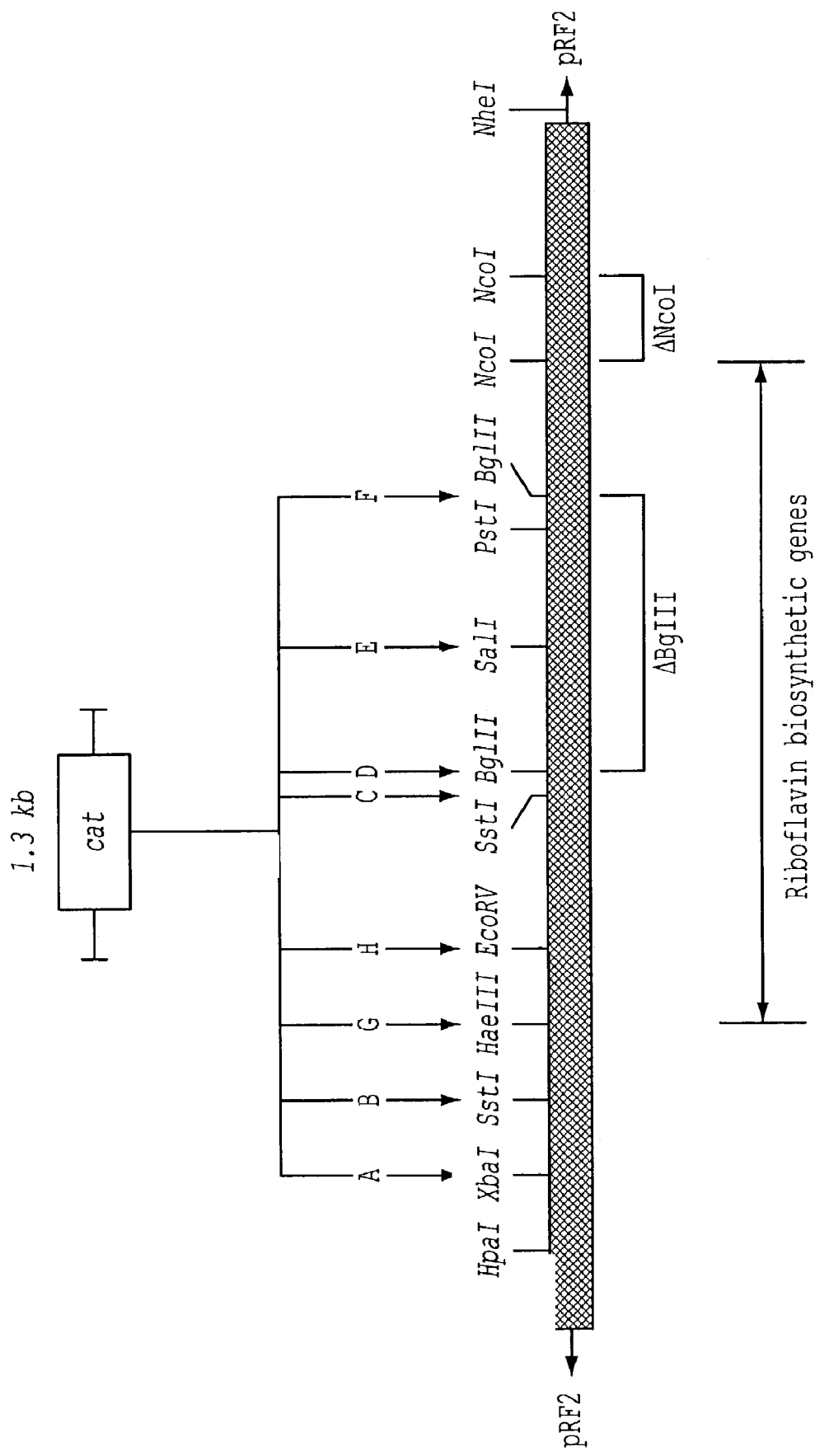

FIG. 8. Identification of regions essential for riboflavin biosynthesis using insertions and deletions. A diagram is presented of the 10 kb cloned EcoRI DNA fragment with the regions essential for riboflavin biosynthesis indicated. Insertions and deletions at the indicated restriction sites enabled the localization of the rib operon. Not all restriction sites are indicated.

FIG. 9. Hairpin-loop structures of the possible rho-independent transcription termination sites. The nucleotide sequences shown are nucleotides 707–749 of SEQ ID NO: 1 for the site upstream from ribP1, nucleotides 1032–1067 of SEQ ID NO: 1 for the site within the 5' leader mRNA and nucleotides 5037–5071 for the site at the 3' end of the rib operon. Their locations in the nucleotide sequence of FIG. 3 are shown below each structure. Also presented are their free energies of formation, determined according to Tinoco et al. (*Nature (London) New Biology* 246:40 (1973)).

Figure 10:
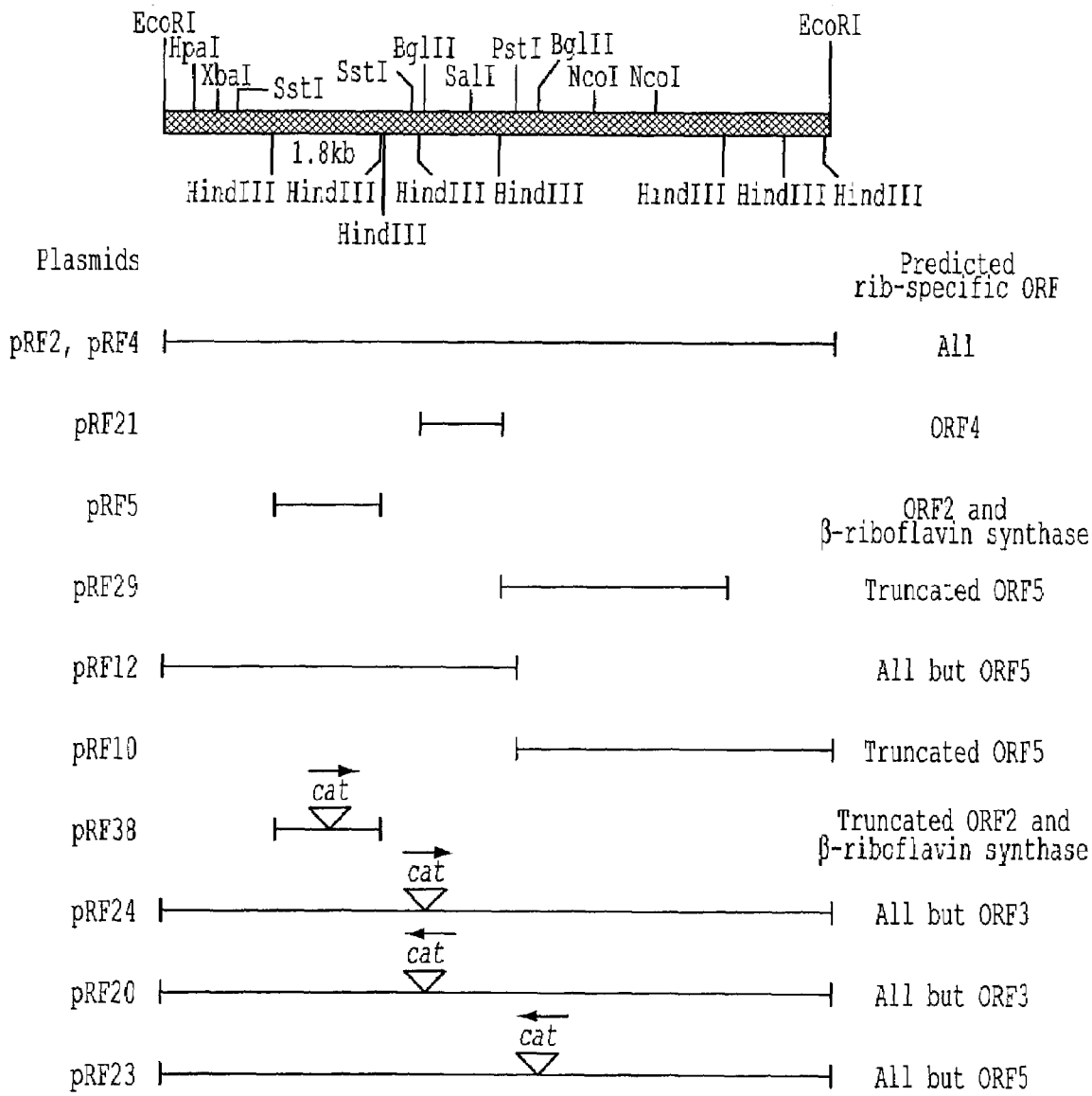

FIG. 10. Structure of various plasmid derivatives used in S-30 in vitro coupled transcription/translation reactions. A schematic diagram is shown of the rib operon regions contained in the plasmid derivatives used in the S-30 reactions, as well as the open reading frames predicted to be expressed.

Figure 11:
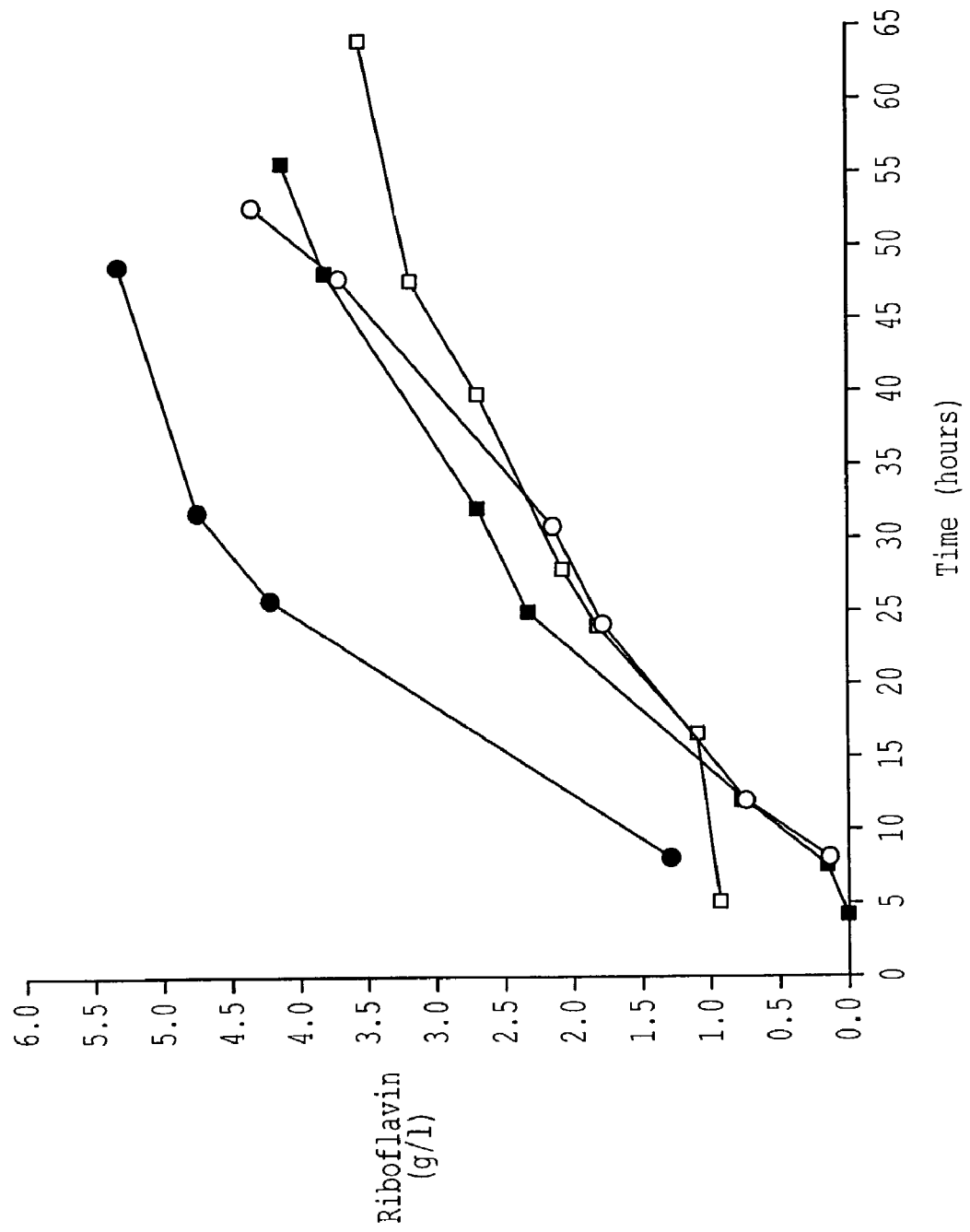

FIG. 11. Comparison of riboflavin production curves. Riboflavin production curves for various fermentation protocols are shown. Open squares: RBF-14 using RB50::[pRF8]$_{60}$ (Ade$^-$). Closed squares: RBF-22 using RB50::pRF8)$_{60}$(Ade$^-$). Open circles: RBF-23 using RB50::[pRF8]$_{60}$(Ade$^-$). Closed circles: RBF-29 using RB50::[PRF8B$_{60}$(Ade$^+$).

Figure 12:
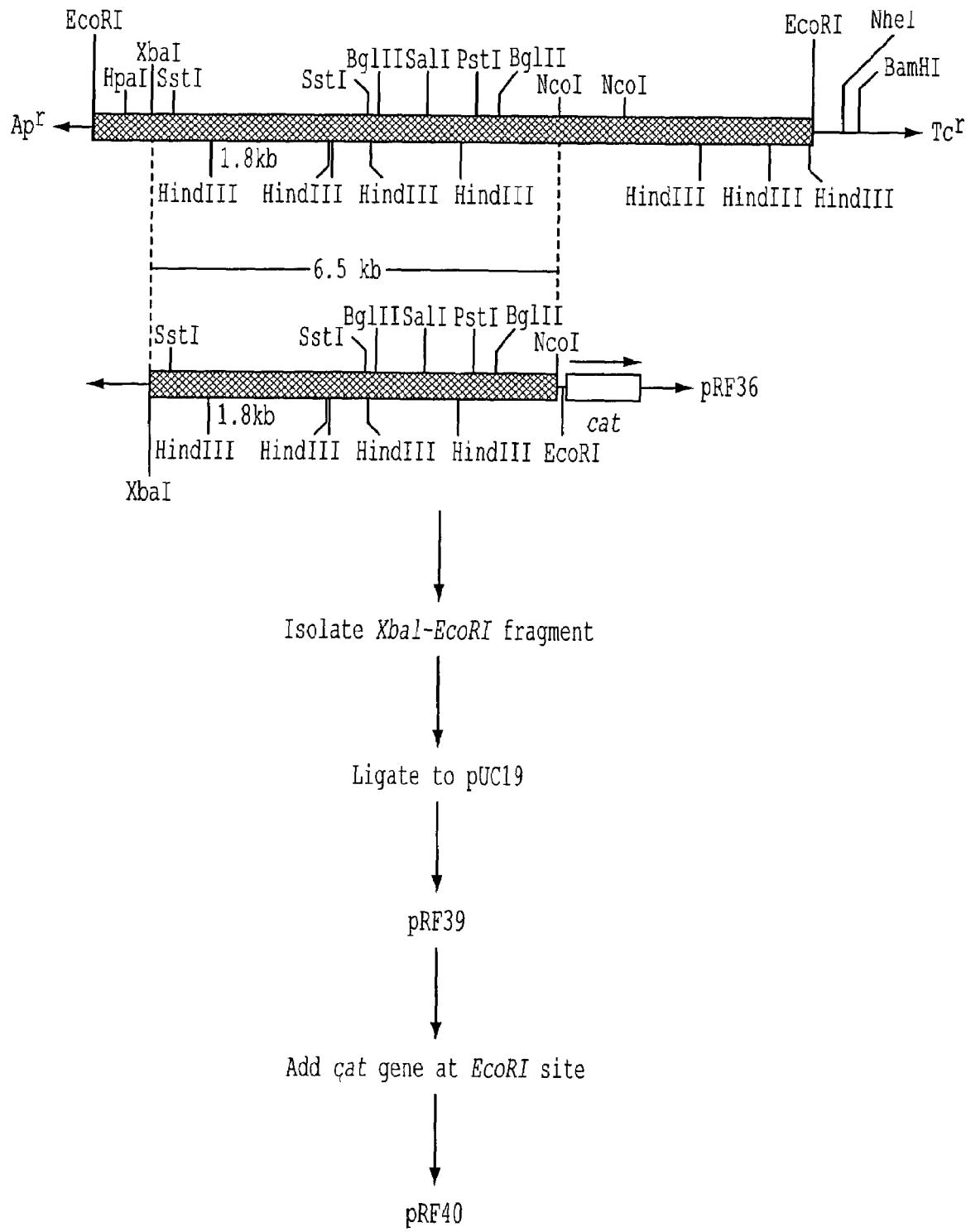

FIG. 12. Construction of pRF40.

Figure 13:
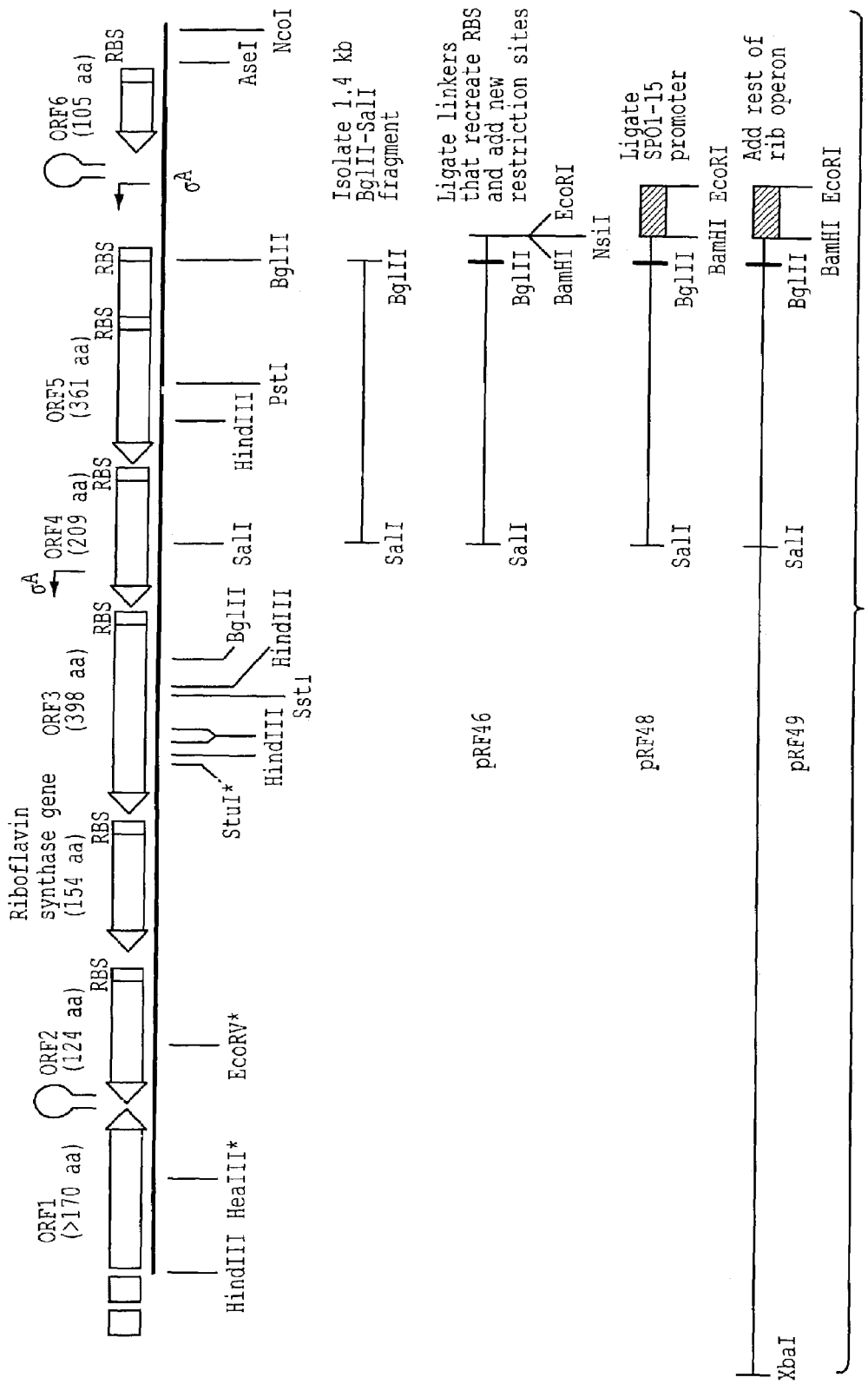

FIG. 13. Construction of pRF50.

Figure 14A:
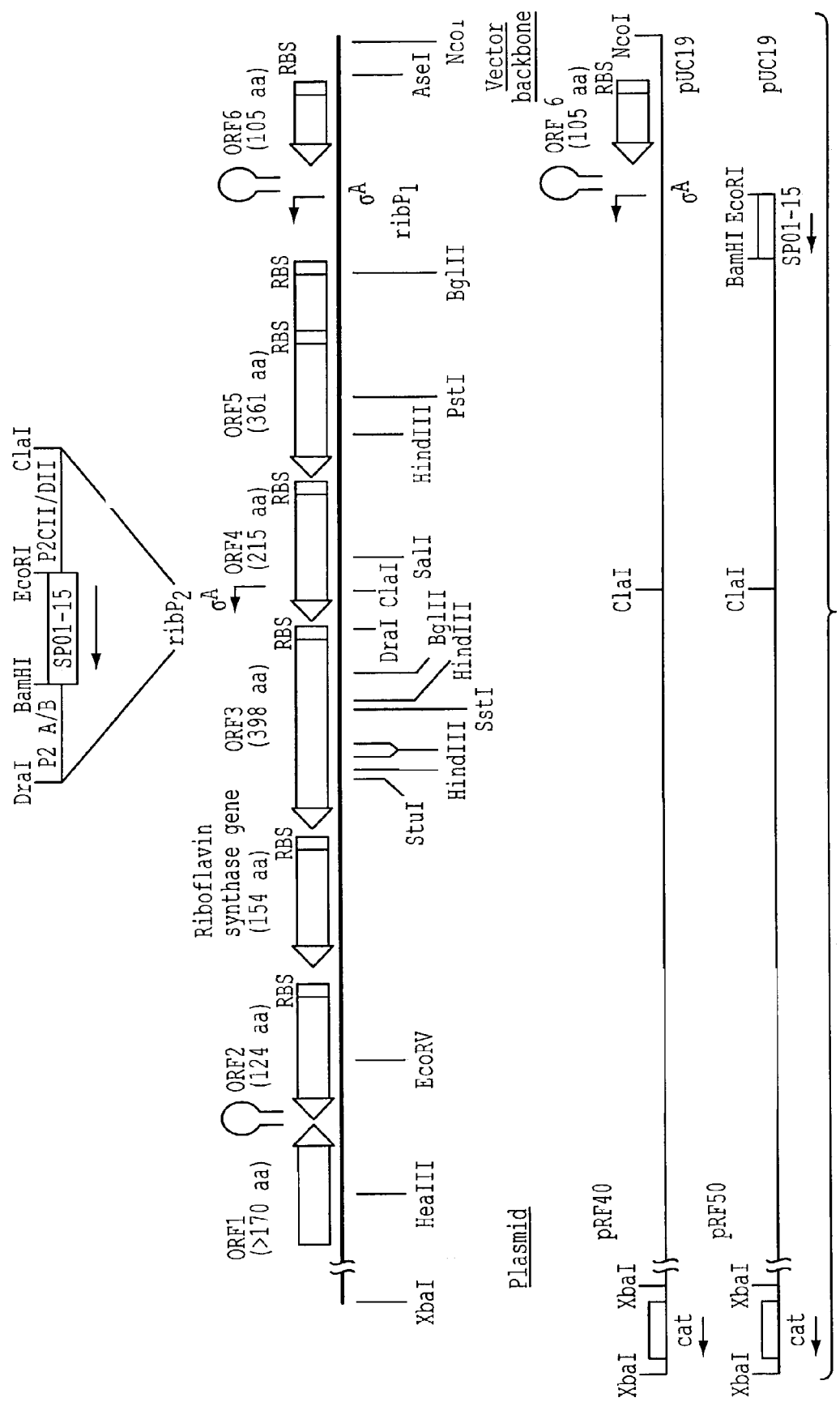
Figure 14B:
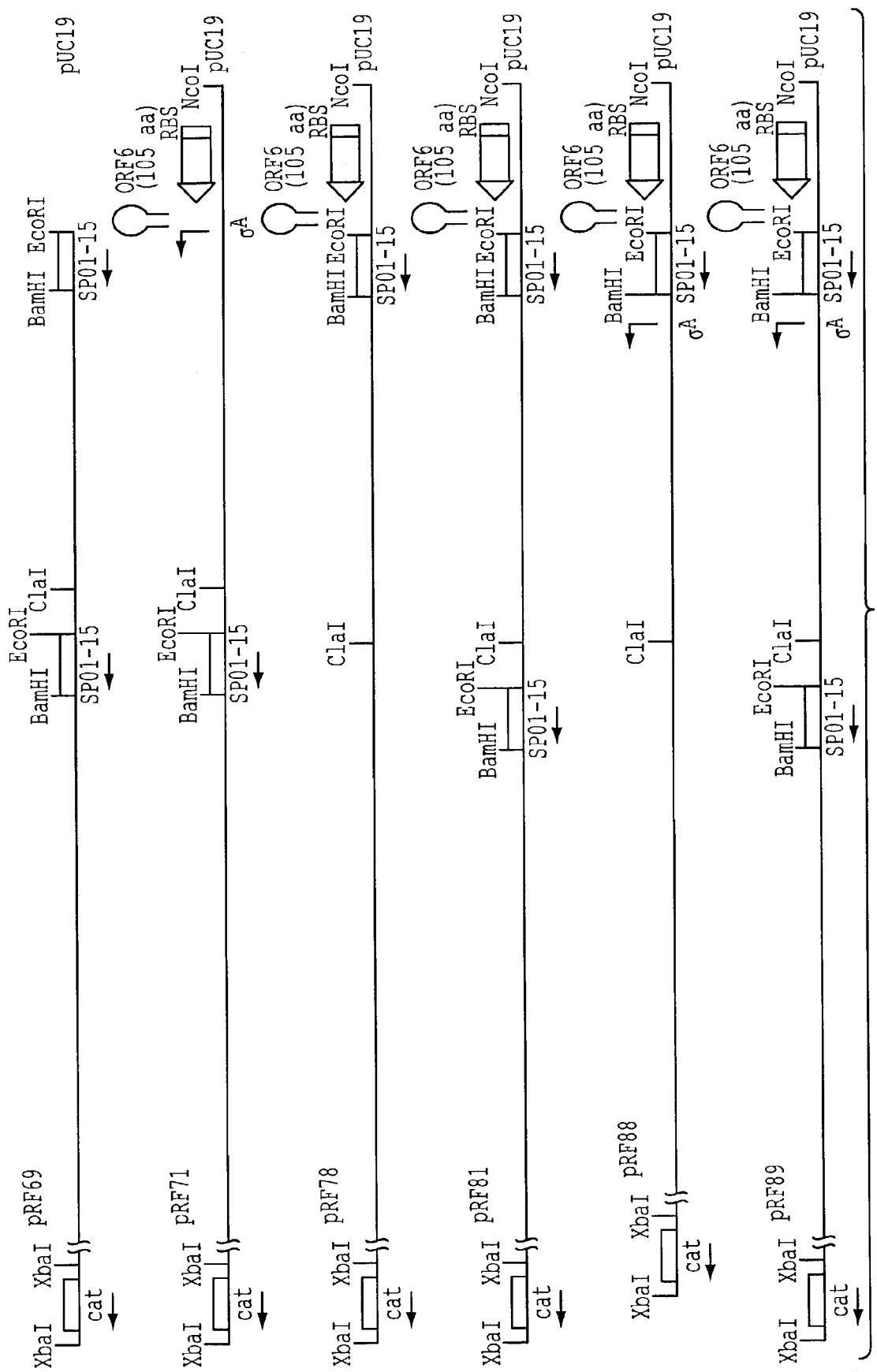
Figure 15:
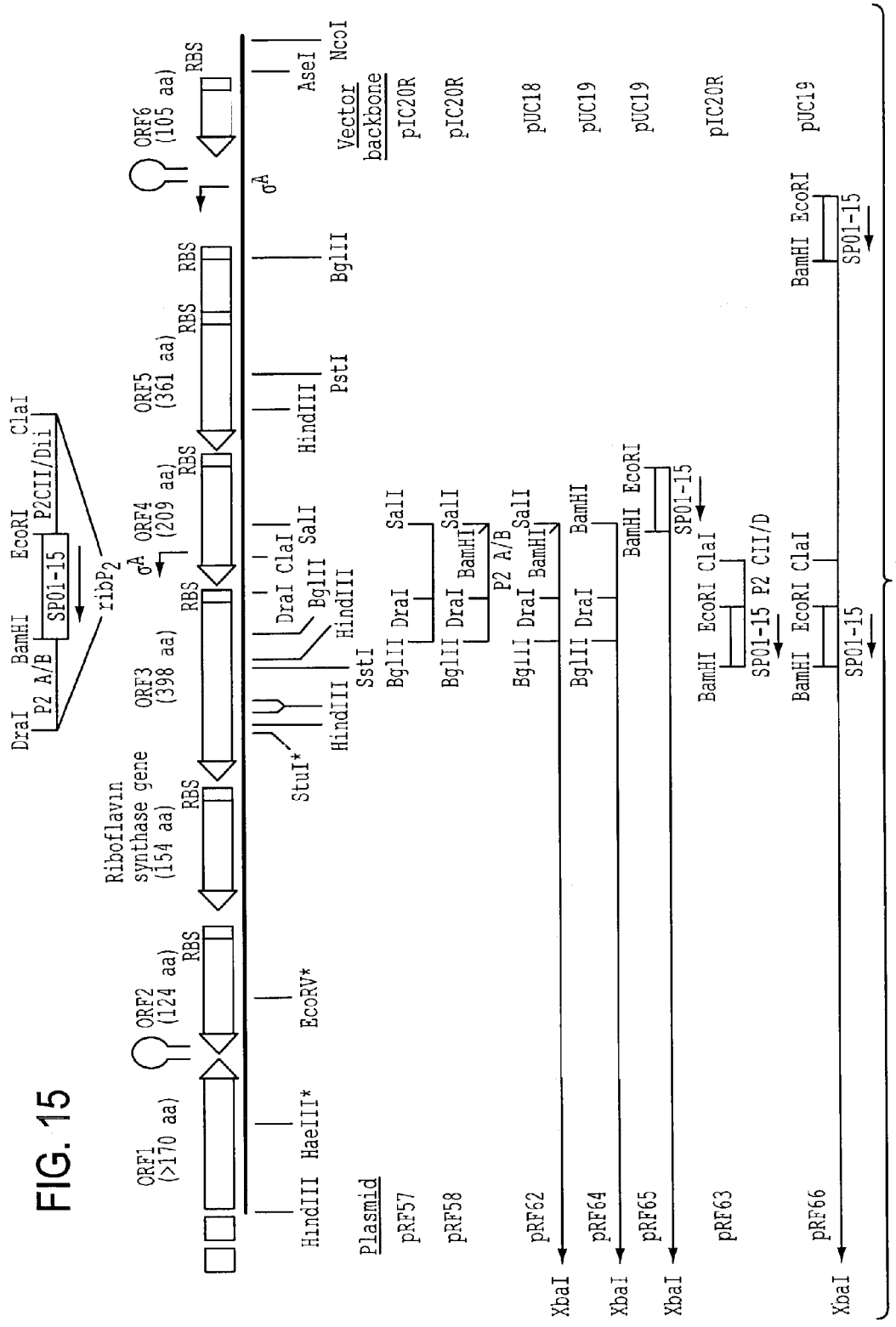
Figure 16A:
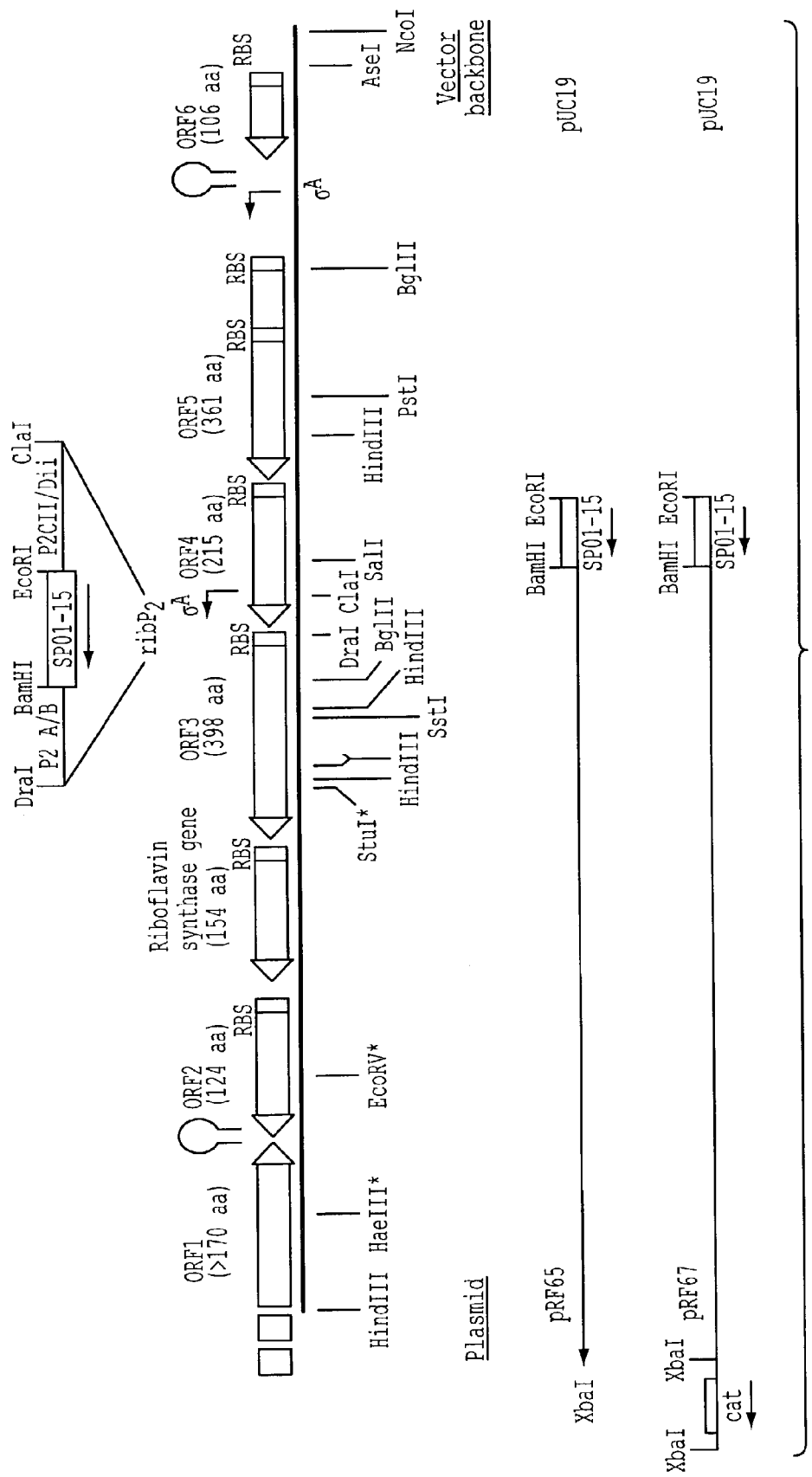
Figure 16B:
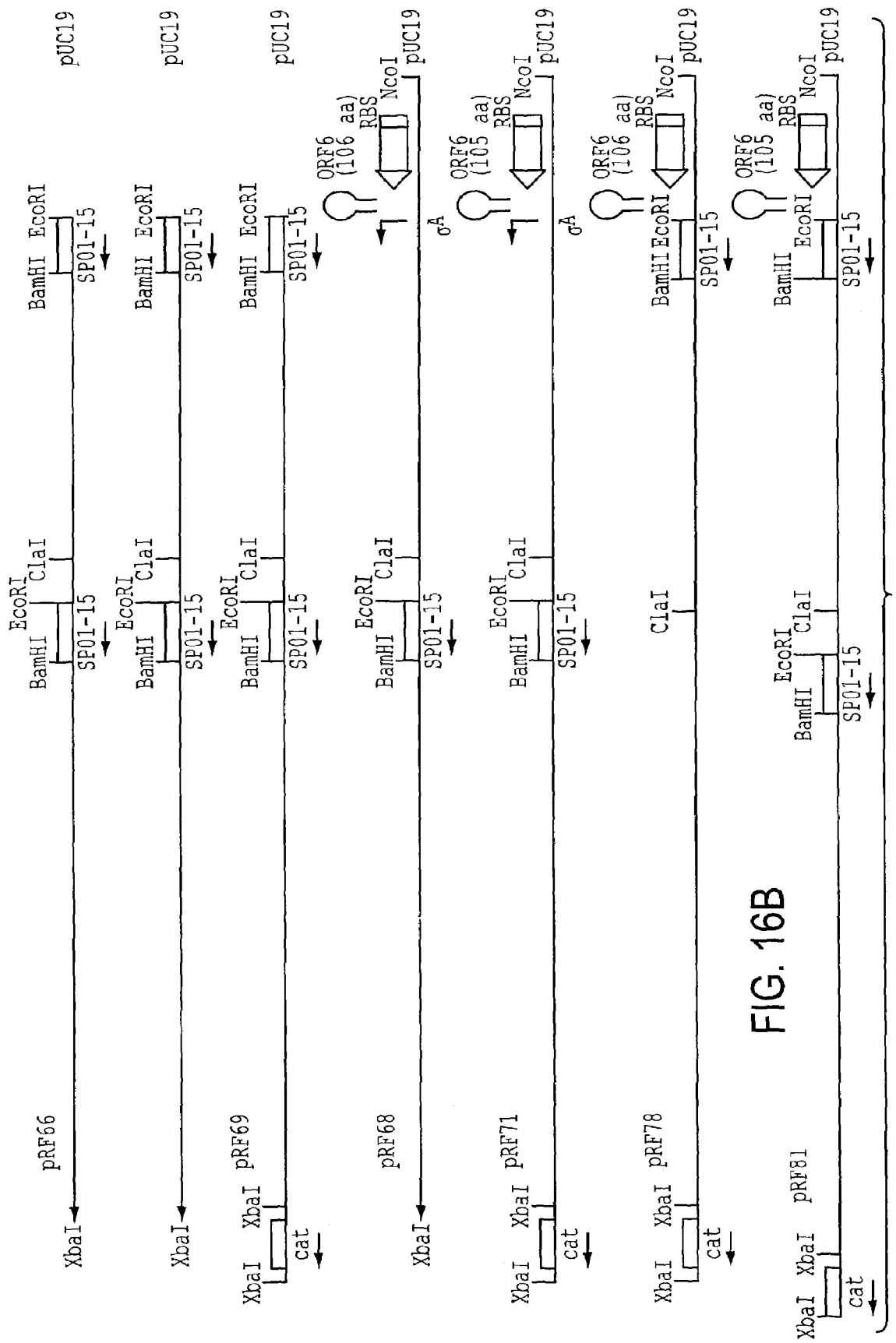

FIGS. 14, 15, and 16. Structure of various vectors.

Figure 17:
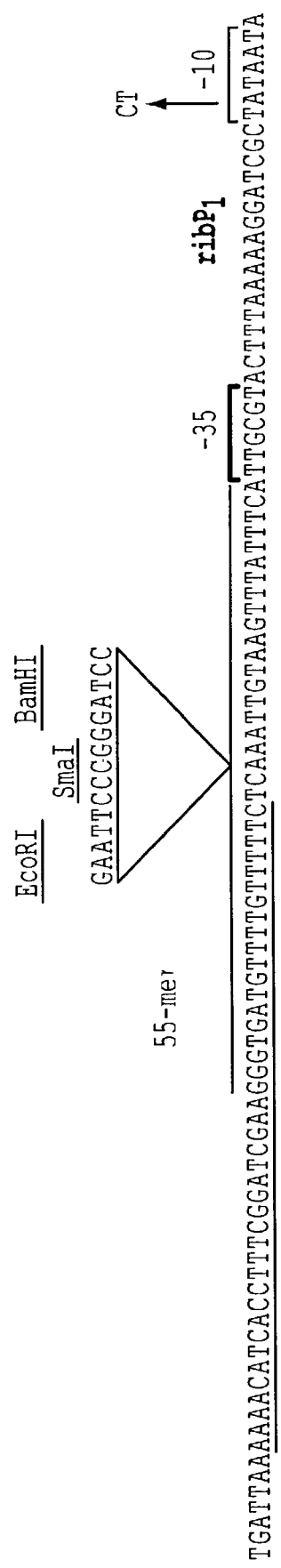

FIG. 17. 55-mer used in plasmid construction flanked on either side by additional sequences homologous to the DNA region ubstream from ribP$_1$ (SEQ ID NO: 9), containing a combination of restriction enzyme sites. 5'-EcoRI-SmaI-BamHI-3' (SEQ ID NO: 10).

FIG. 18. Various oligonucleotides used in vector construction: RB-5 (SEQ ID NO: 11), RB-6 (SEQ ID NO: 12), P2-A (SEQ ID NO: 13), P2-B (SEQ ID NO: 14), P2-CII (SEQ ID NO: 15) and P2-DII (SEQ ID NO: 16).

HOST BACTERIA

In the practice of the present invention, host bacterial strains are derived that contain one or more mutations in genes of the riboflavin biosynthetic pathway or in the biosynthetic pathway of various purines, which mutations lead to riboflavin overproduction. In one embodiment, such mutations lead to riboflavin overproduction by deregulating steps in the riboflavin biosynthetic pathway. In another embodiment, the mutations increase riboflavin production by causing an inhibition in the use in an alternative metabolic pathway of a precursor for riboflavin biosynthesis.

In a specific embodiment, desired mutations in the genetic background of the host bacteria can be induced by exposure to analogs of purine or riboflavin that compete with their authentic counterparts in the metabolic pathways of the host; bacteria that survive such exposure will have mutations that allow them to overproduce the authentic counterpart to the analog, thus "competing out" the purine or riboflavin analog that would otherwise be lethal. The biosynthesis of riboflavin in *B. subtilis* originates with guanosine triphosphate (FIG. 1, structure 1). Guanosine triphosphate (GTP), via guanosine monophosphate (GMP), is a product of the purine biosynthetic pathway (FIG. 2). In a preferred embodiment, to obtain a host strain that overproduces riboflavin, one can use classical genetics to both increase the amount of GTP that the cell produces and to deregulate the riboflavin pathway. Purine overproduction in *B. subtilis* can be achieved by obtaining mutants resistant to purine analogs or antagonists. Examples of some of the purine analogs that can be used include but are not limited to 8-azaguanine (Ishii and Shiio, *Agric. Biol. Chem.* 36:1511, 1972; Konishi and Shiro, *Agric. Biol. Chem.* 32:396, 1968), psicofuranine and decoyinine (Matsui et al., *Adric. Biol. Chem.* 43:1739, 1979; Matsui et al., *Agric. Biol. Chem.* 43:393, 1979), 8-azaxanthine, sulfaguanine, 6-thioguanine (Debabov, V. G. in *The Molecular Biology of the Bacilli* vol. 1 *Bacillus subtilis*, D. A. Dubnau, ed. (Academic Press, New York), pp. 331–370, 1982) and others, and/or the antagonist methionine sulfoxide (Matsui et al., *App. Env. Microbiol.* 34:337, 1977), and any combination thereof.

The riboflavin pathway can be deregulated by obtaining mutants resistant to a riboflavin analog. An example of a riboflavin analog that can be utilized is roseoflavin (Matsui et al., *Agric. Biol. Chem.* 46:2003, 1982).

In a specific embodiment of the present invention, bacteria that are mutationally resistant to the analogs azaguanine, decoyinine and roseoflavin, can be used. Specific mutants resistant to each of these compounds are described below. Bacteria with mutations rendering them resistant to other analogs can also be used. It is also deemed within the scope of the present invention to utilize bacteria with different mutations rendering resistance to these same analogs, or different combinations of these mutations, either in combination, with or without, various mutations to other analogs.

If exposure to the analog alone does not produce resistant mutants at a high enough frequency, various mutagens can be used to increase the frequency of mutation in general and thus increase the number of analog-resistant mutants. As one example, ethyl methyl sulfonate can be used, but other mutagens including but not limited to nitrosoguanidine or UV irradiation can also be used.

Suitable bacterial hosts include all Bacilli species (including in a preferred embodiment *B. subtilis*), *E. coli*, and many other gram-positive and gram-negative bacteria. Species which can recognize the promoter sequences of the cloned rib operon to be inserted within their genome are suitable for use. The plasmids described below can be used to introduce rib genes into other bacteria by standard procedure,.e.g., transformation. Expression of the inserted rib genes can be determined by spectroscopy as described below, or by observation of the bacteria under UV light, as described below.

In addition to creating mutations by exposure to purine or riboflavin analogs, bacterial strains that already contain mutations that are known to affect their, purine or riboflavin biosynthetic pathways can be utilized. For example, the present invention makes use of but is not limited to *B. subtilis* strain 1A382, which contains the mutation pur-60, making it auxotrophic for adenine. Because this mutation blocks the utilization of the riboflavin precursor inosine monophosphate (IMP) in a metabolic pathway other than riboflavin production, increased amounts of IMP are available for riboflavin biosynthesis, thus increasing riboflavin production. There are many other mutations which can be utilized to potentially increase riboflavin production, including but not limited to guaC3, his⁻ and others that are included within the scope of the present invention. The guaC3 mutation prevents the conversion of GMP back into IMP (see FIG. 2), thus increasing the amount of riboflavin biosynthetic precursors available.

Suitable mutations affecting riboflavin overproduction can be mapped by various methods known in the art. In a specific embodiment, a mutation can be mapped by complementation of auxotrophic mutants.

Riboflavin Biosynthetic Genes

The riboflavin biosynthetic genes from various bacteria can be cloned for use in the present invention. Yeast or bacterial cells from species including but not limited to the genus *Bacillus*, *E. coli* and many other gram-positive and gram-negative bacteria can potentially serve as the nucleic acid source for the molecular cloning of the rib operon. The DNA containing the rib operon may be obtained, by standard procedures known in the art, for example, from a DNA library prepared by cloning chromosomal DNA or fragments thereof, purified from the desired bacterial cell, into a suitable vector for propagation of the gene. (See, for example, Maniatis et al., 1982, *Molecular Cloning, A Laboratory Manual*, Cold Spring Harbor Laboratory, Cold Spring Harbor, N.Y.; Glover, D. M. (ed.), 1982, *DNA Cloning: A Practical Approach*, MRL Press, Ltd., Oxford, U.K., Vol. I, II).

In the molecular cloning of the gene from chromosomal DNA, fragments are generated, some of which will encode the desired rib operon. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to agarose and polyacrylamide gel electrophoresis and density gradient centrifugation.

Once the DNA fragments are generated, DNA libraries are prepared using an appropriate cloning and/or expression vector. A large number of vector-host systems known in the art may be used. Possible vectors include, but are not limited to, plasmids or modified viruses, but the vector system must be compatible-with the host cell used. For *E. coli* such vectors include, but are not limited to, bacteriophages such as λ derivatives, high-copy plasmids such as pBR322 or pUC plasmids, or low-copy plasmids derived from *Pseudomonas* plasmid RK2. For *Bacillus* such vectors include, but are not limited to, bacteriophages such as ρ11 (Dean et al., *J. Virol.* 20: 339, 1976; Kawamura et al., *Gene* 5:87, 1979) or ø105 derivatives (Iijima et al., *Gene* 9:115, 1980; Errington, *J. Gen. Microbiology* 130:2615 1984; Dhaese et al., *Gene* 32: 181, 1984; Errington, J. in *Bacillus Molecular Biology and Biotechnology Applications*, A. T. Ganesan and J. A. Hoch, eds. (Academic Press, New York,), p. 217, 1986), high-copy plasmids such as pUB110 (Ehrlich, *Proc. Natl. Acad Sci.* (*USA*) 74: 1680, 1977) or pBD64, or low-copy plasmids such as pE194 derivatives (Gryczan, T. J. in *The Molecular Biology of the Bacilli*, D. A. Dubnau, ed. (Academic Press, New York), pp. 307–329, 1982; Ho◆inouchi and Weisblum, *J. Bacteriol.* 150: 804, 1982). Recombinant molecules can be introduced into host cells via transformation, transfection, protoplasting, infection, electroporation, etc.

Once the DNA libraries are generated, identification of the specific clones harboring recombinant DNA containing the rib operon may be accomplished in a number of ways (as described, for example, in Maniatis et. al., supra). For example, if an amount of the operon or a fragment thereof is available from another bacterial source (e.g., from *E. coli*) and is sufficiently homologous to the riboflavin biosynthetic genes of *Bacillus* to hybridize thereto, that DNA can, be purified and labeled, and the generated bank of DNA fragments may be screened by nucleic acid hybridization to the labeled probes (Benton, W. and Davis, R., 1977, *Science* 196:180; Grunstein, M. and Hogness, D., 1975, *Proc. Natl. Acad. Sci. U.S.A.* 72:3961). Alternatively, sequences comprising open reading frames of the endogenous rib operon, or subsequences thereof comprising about 10, preferably 15 or more nucleotides, may be used as hybridization probes. Such probes can be made synthetically, based on a portion of the nucleic acid or amino acid sequence (examples of which are provided below) of a gene product known to be encoded by the operon ("reverse genetics"). If a purified rib operon-specific probe is unavailable, cloned gene libraries of restriction fragments (from partial Sau3A-digests, for example) can be made in bacteria, especially *B. subtilis* or *E. coli*, and the rib operon-containing recombinant clones can be identified by either marker-rescue or complementation of known rib mutations.

In a preferred embodiment, the rib operon of *B. subtilis* can be isolated for use from an *E. coli* plasmid library of *B. subtilis* DNA. In particular, and as described below, the *B. subtilis* rib operon can be isolated by virtue of its homology to a radiolabelled, synthesized nucleotide probe that is derived from an internal region of a gene product known to be encoded by the operon of *B. subtilis*. Although a portion of the amino acid sequence for β-riboflavin synthase (Ludwig et al., *J. Biol. Chem.* 262:1016, 1987) can be the basis for such a probe, with the third nucleotide of each codon estimated from frequency of codon usage, a similar probe based on another region of this protein or another protein from the rib operon can be utilized and would fall within the scope of the present invention. The present invention further enables screening by use of synthetic probes which are derived from the nucleic acid sequence shown in FIG. 3.

Analogous methods to those detailed here can be used to isolate the rib operon of other bacteria, especially other Bacilli or *E. coli*. In a specific embodiment, such clones can be selected by assay for ability to hybridize to the labeled *B. subtilis* rib operon or a hybridizable portion thereof. It is well known in the art that starting from an appropriate mRNA preparation, cDNA can be prepared; such cDNA can also be used in accordance with the present invention to prepare vectors for the transformation of appropriate bacteria for riboflavin overproduction.

Once the host cells with recombinant DNA molecules that include the isolated rib operon or a portion thereof are identified, the DNA may be obtained in large quantities. This then permits the rib operon to be manipulated and its nucleotide sequence to be determined using various cloning and sequencing techniques familiar to those knowledgeable in the art.

For example, insertional mutagenesis can be used to locate and characterize the rib operon and genes thereof within a cloned piece of DNA. In a specific embodiment, rib-biosynthetic containing regions can be identified by inserting small cat (chloramphenicol acetyltransferase)-containing restriction fragments into several different restriction enzyme sites of the cloned DNA, and testing each derivative for insertional inactivation of riboflavin biosynthesis in an appropriate host (see below).

The cloned DNA corresponding to the rib operon can be analyzed by methods including but not limited to Southern hybridization (Southern, E. M., 1975, *J. Mol. Biol.* 98:503–517), Northern hybridization (see e.g., Freeman et al., 1983, *Proc. Natl. Acad. Sci. U.S.A.* 80:4094–4098), restriction endonuclease mapping (Maniatis et al., 1982, *Molecular Cloning, A Laboratory Manual*, Cold Spring Harbor Laboratory, Cold Spring Harbor, N.Y.), and DNA sequence analysis. Restriction endonuclease mapping can be used to roughly determine the genetic structure of rib operon. Restriction maps derived by restriction endonuclease cleavage can be confirmed by DNA sequence analysis.

DNA sequence analysis can be performed by any techniques known in the art, including but not limited to the method of Maxam and Gilbert (1980, *Meth. Enzymol.* 65:499–560), the Sanger dideoxy method (Sanger, F., et al., 1977, *Proc. Natl. Acad. Sci. U.S.A.* 74:5463), or use of an automated DNA sequenator (e.g., Applied Biosystems, Foster City, Calif.). As an example, the DNA sequence of the rib operon of *B. subtilis* is presented in FIG. 3.

Once the nucleotide sequence of the rib operon has been determined, putative open reading frames (ORFs) can then be identified along with the deduced amino acid sequence of their encoded product. Actual identification of the encoded product can be carried out, e.g., by performing S-30 coupled in vitro transcription/translation reactions, with various ORFs used as templates. Various mutational derivatives of the ORFs can also be tested for activity in functional assays of the S-30 reaction products, in order to test the function of the encoded products.

In a specific embodiment of the invention relating to the *B. subtilis* rib operon, and detailed in the examples below, the above-described methods were used to determine that *B. subtilis* riboflavin biosynthesis is controlled by a single operon of approximately 4.2 kb containing five biosynthetic genes: the β subunit of riboflavin synthase and ORFs designated 2, 3, 4, and 5 (see FIG. 4). ORFs 2, 3, 4, and 5 were subsequently shown to encode proteins with molecular weights of about 15 kd, 47 kd, 26 kd, and 44 kd, respectively. As described below, ORF 5 was shown to encode a putative rib-specific deaminase that catalyzes the reduction of a deaminated pyrimidine to a ribitylamino-linkage in an early step in riboflavin biosynthesis. Our data also indicated that ORF 4 encodes the α subunit of riboflavin synthase and ORF 3 encodes a GTP cyclohydrolase, while ORF 2 possibly encodes a rib-specific reductase. ORF 1 and ORF6 were found to be outside the primary transcription unit of the rib operon. The primary site for initiation of transcription of the rib operon was determined to be probably the apparent $\sigma^A$ promoter located 290 bp upstream from the first gene in the operon, ORF 5 (FIG. 4, $P_1$). The coding regions, promoters and transcription termination sites of the *B. subtilis* rib operon are shown in Table VI below.

The present invention encompasses the nucleotide and amino acid sequences of the genes of the rib operon, as well as subsequences thereof encoding functionally active peptides, and sequences which are substantially the same as such sequences. A functionally active peptide, as used herein, shall mean a protein or peptide which is capable of catalysing a reaction leading to riboflavin biosynthesis. A functionally active nucleic acid sequence shall mean a sequence capable of regulating riboflavin biosynthesis. A sequence substantially the same as another sequence shall mean a sequence capable of hybridizing to the complementary sequence thereof. In addition, a nucleic acid sequence not naturally controlling the expression of a second nucleic acid sequence shall mean a sequence which does not control the expression of the second sequence in the bacterium from which the second sequence is isolated.

Once the genetic structure of the rib operon is known, it is possible to manipulate the structure for optimal use in the present invention. For example, the rib operon can be engineered to maximize riboflavin production.

Depending on the host-vector system utilized, any one of a number of suitable transcription and translation elements may be used. Promoters produced by recombinant DNA or synthetic techniques may also be used to provide for transcription of the inserted sequences. When propagating in bacteria the regulatory sequences of the rib operon itself may be used. In an embodiment in which the entire rib operon, or greater than one gene thereof, is desired to be expressed as a polycistronic message, a prokaryatic host is required. In an embodiment in which a eukaryotic host is to be used, appropriate regulatory sequences (e.g., a promoter) must be placed in the recombinant DNA upstream of each gene/ORF that is desired to be expressed.

Specific initiation signals are also required for efficient translation of inserted protein coding sequences. These signals include the initiation codon (ATG, GTG or TTG) and adjacent sequences, such as the ribosome binding site (RBS). It should be noted that the RBS of a given coding sequence can be manipulated to effect a more efficient expression of that coding sequence at the translational level. In cases where an entire open reading frame of the rib operon, including its own initiation codon and adjacent regulatory sequences, is inserted into the appropriate expression vectors, no additional translational control signals may be needed. However, in cases where only a portion of the coding sequence is inserted, or where the native regulatory signals are not recognized by the host cell, exogenous translational control signals, including the initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

In addition, a host cell strain may be chosen which modulates the expression of the rib operon gene(s) or modifies and processes the gene product(s) thereof in the specific fashion desired. Expression from certain promoters can be elevated in the presence of certain inducers; thus, expression of the genetically engineered rib operon proteins may be controlled. In one embodiment, the regulatory regions of the operon, such as the promoter and the termination/anti-termination regulatory sequences, can be manipulated or replaced with constitutive or growth-regulated promoters to deregulate the rib operon and thus increase riboflavin production. Furthermore, appropriate cell lines or host systems can be chosen to ensure the desired modification and processing of the expressed proteins. Many manipulations are possible and within the scope of the present invention.

In one specific embodiment of the invention, the 5' regulatory sequence of the B. subtilis rib operon can be removed and replaced with one or more of several B. subtilis promoters; such a construction will cause high-level expression of the rib biosynthetic genes. This approach would involve the introduction of new restriction sites within a 20–30 bp region between the end of the transcription terminator and the RBS sequence of the first gene in the operon ORF 5. Such restriction sites can be introduced by either site-directed mutagenesis or by deleting all regulatory sequences upstream from the right-most BglII (BglII$_R$) site located within the first 30 bp of ORF 5 (see FIGS. 3 and 4) and inserting at this site a synthetic oligonucleotide that finishes off the 5' end of ORF 5 (including the ribosomal-binding site) and contains new upstream restriction sites. Once these constructions are made, promoter-containing restriction, fragments with ends compatible to the new restriction sites can be introduced, causing expression of the rib genes under the control of the new promoter. Both constitutive and growth-regulated B. subtilis promoters can be used, including but not limited to strong promoters from the lytic bacteriophage SPO1 genes, veg, amy (amylase), and apr (subtilisin).

In another aspect of the invention, rib operon DNA fragments which have transcriptional regulatory activity (e.g., promoters) can be used to regulate the expression of heterologous gene products.

Introduction of Rib Operon into Bacterial Host

According to the present invention, the rib operon can be introduced into bacteria, including for example, Bacilli and E. coli, where it is expressed. In a preferred embodiment, the bacterial host is one of the mutant hosts described above. In a specific embodiment, the cloned rib operon is integrated into the host chromosomal DNA, where it is replicated and expressed along with host genomic DNA. In a most preferred embodiment, multiple copies of the rib operon are integrated into the host chromosomal DNA, thus providing for amplified expression of the rib operon in the deregulated host. One method in which this may be accomplished is chromosomal insertion of a cat-containing rib operon followed by chloramphenicol amplification of the operon, as detailed in the examples sections infra. One can also use a tet$^r$ gene, or certain other drug resistance genes that are expressed in Bacillus, with the same technique.

In specific embodiments, integration vectors containing the rib operon fragment can be engineered so as to contain the rib operon on the smallest possible DNA fragment, in an attempt to obtain greater amplification of the vector within the host chromosome. For example, vector DNA sequences may be deleted, and/or nonessential DNA flanking the rib operon can be deleted.

Riboflavin Production

In general, bacteria that are prototrophic for riboflavin survive on minimal medium in the absence of riboflavin. Production of riboflavin can be detected and quantified by various methods. In a preferred embodiment, overproduction of riboflavin is readily observed when overproducing bacteria are exposed to UV light at 366 nm, as described infra, producing an observable, yellow fluorescence. For example, many of the engineered plasmids of the present invention are produced in E. coli. For some of these plasmids, overproduction of riboflavin has been confirmed by this method. The amount of riboflavin produced can be quantitated, e.g., with reverse-phase high performance liquid chromatography (HPLC). Cell-free supernatants from bacteria can be fractionated over an HPLC column, as described infra, and monitored for riboflavin at 254 nm. By extrapolation from a standard curve, the concentration of riboflavin can be determined by the area of the peak on the chromatogram.

Riboflavin can also be quantitated by fluorescence spectrophotometry. For example, samples containing riboflavin can be read in a fluorescence spectrophotometer set at an emission wavelength of 525 nm and an excitation wavelength of 450 nm.

In addition, other methods known in the art are available to detect or quantitate riboflavin based on its physical and biological properties.

Fermentation

Riboflavin overproducing bacteria can be grown in vessels ranging from shake flasks to large "batch" fermentors, by methods known in the art (see below). In a preferred embodiment, nutrient feed can be manipulated to maximize riboflavin production at the minimum cost by varying the nutrients in the medium.

In a specific embodiment, amplified rib-containing genes can be maintained at high-copy number in the bacterial chromosome by the inclusion of about 60 μg/ml chloramphenicol in the inoculum seed strain (but not necessarily in the fermentor). Chemap 14-liter fermentors can be used at 1000 rpm with a head pressure of 0.6 atmospheres.

The cells (especially recombinant bacteria as specifically mentioned herein) are grown under suitable growth conditions. Such suitable growth conditions are characterized by limiting the availability of a component of the growth medium and/or feed medium in such a way that aerobic conditions for the growth of said recombinant bacterium are maintained. Such conditions can be also characterized e.g. by maintaining a level of dissolved oxygen at a concentration between about 5% to 30%. One skilled in the art is familiar with the fact that such levels of dissolved oxygen can vary dependent on the specific technical equipment used for growing said recombinant bacteria and for measuring said dissolved oxygen concentration. Under anaerobic conditions the synthesis of riboflavin is reduced. In some embodiments, the limiting component is chosen from a carbon source, nitrogen source, or a component required by the cells (e.g., in the feed medium). For example, if the cells are auxotrophic, for example, for methionine, a limiting level of methionine may be provided in the growth medium. In another example, such component could be glucose or a carbonic acid, e.g. a citric acid cycle acid, such as citric acid or succinic acid, or an amino acid.

EXAMPLE 1

Riboflavin-Overproducing B. subtilis Mutants

We describe in the examples herein the production of strains of Bacillus subtilis which overproduce riboflavin. In order to accomplish this, we used classical genetics, genetic engineering, and fermentation. Classical genetics with selection using purine and riboflavin analogs was used to deregulate the pathways for purine (riboflavin precursor) and riboflavin biosynthesis. Riboflavin production was increased further by cloning and engineering the genes of the riboflavin biosynthetic pathway (the rib operon), allowing for constitutive, high-level production of rate-limiting biosynthetic enzyme(s).

The biosynthesis of riboflavin in *B. subtilis* originates with GTP (FIG. 1). To obtain a host that overproduces riboflavin we used classical genetics to both increase the amount of GTP that the cell produces and to deregulate the riboflavin pathway. Purine overproduction in *B. subtilis* can be achieved by obtaining mutants resistant to purine analogs such as azaguanine and decoyinine, and other antagonists such as methionine sulfoxide (see e.g., Ishii and Shiio, *Agric. Biol. Chem.* 36(9):1511–1522, 1972; Matsui et al., *Agric. Biol. Chem.* 43(8):1739–1744, 1979). The riboflavin pathway can be deregulated by obtaining mutants resistant to the riboflavin analog roseoflavin (Matsui et al., *Agric. Biol. Chem.* 46(8):2003–2008, 1982). Roseoflavin-resistant strains were selected from several strains which had been previously mutagenized and which were resistant to several purine analogs. Described below are the methods used to produce a strain (RB50) which overproduces riboflavin.

8-Azapuanine-Resistant Mutants

*B. subtilis* is effectively killed by the purine analogue 8-azaguanine (Sigma Chemical Co., St. Louis, Mo.) at a concentration of 500 μg/ml, and resistant mutants appear spontaneously at a frequency of less than 1 in $10^8$. Ethyl methyl sulfonate (EMS; Sigma) at 30 μg/ml was used as a mutagen to increase the frequency of azaguanine-resistant ($Ag^r$) mutations. Mutagenesis was performed on cells from *B. subtilis* strain 168 by standard procedures (Miller, 1972, *Experiments in Molecular Genetics*, Cold Spring Harbor Laboratory, Cold Spring Harbor, N.Y.). After plating $4 \times 10^6$ mutagenized cells on minimal medium (Sloma et al., *J. Bact.* 170:5557, 1988) containing 500 μg/ml azaguanine and restreaking for single colonies, 35 $Ag^r$ colonies resulted. one mutant, RB11 ($Ag^r$-11), was used in the construction of RB50.

Decoyinine-Resistant Mutants

Decoyinine-resistant ($Dc^r$) mutations were obtained spontaneously at a frequency of 1 in $10^6$ or after EMS mutagenesis at 1 in $10^5$ by plating cells on minimal medium containing 100 μg/ml of decoyinine (Upjohn Co., Kalamazoo, Mich.). A $DC^r$ mutant of RB11 was obtained by mutagenesis with EMS as described above. One $Dc^r$ colony, RB15 ($Ag^r$-11, $Dc^r$-15), was used in the construction of RB50.

Transfer of the Ag and Dc Mutations

These purine analog-resistant mutations were transferred to a different strain background in order to isolate them from any unwanted EMS-induced mutations and to verify that the $Ag^r$ and $Dc^r$ mutations were due to single loci. Since part of the "carbon flow" from inosine monophosphate (IMP), a riboflavin precursor, is also used for adenine nucleotide biosynthesis, a host strain was selected that-was blocked in the adenosine monophosphate (AMP) pathway via the mutation pur-60, allowing more carbon material to "flow" from IMP to the guanine nucleotide precursors of riboflavin (FIG. 2). *B. subtilis* strain 1A382 (hisH2, trpC2, pur-60) was made competent (Sloma et al., *J. Bact.* 170:5557 (1988)) and transformed (by the method of Gryczan et al., *J. Bact.* 134:318 (1978)) with total DNA prepared from the $Ag^r$/$Dc^r$ mutant RB15. The Trp⁺ (tryptophan) revertant colonies were selected, with 3.3% (10/300) of those also being $Dc^r$ and 2.3% (7/300) $Ag^r$. This result was not unexpected since, due to "congression" (transformation of a second unlinked marker), a number of the Trp⁺ colonies should also be resistant to decoyinine or azaguanine.

One $Dc^r$ colony, RB36 (his H2, pur-60, $Dc^r$-15), one $Ag^r$ colony, RB40 (his H2; r-60, $Ag^r$-11), and one $Dc^r$/$Ag^r$ colony (which was also found to be his⁺), RB39 (pur-60, $Ag^r$-11, $Dc^r$-15), were all selected for further study.

Methionine Sulfoxide-Resistant Mutants

Selection using high levels of methionine sulfoxide (MS; 10 mg/ml, Sigma) resulted in spontaneous mutants appearing at a sufficiently high frequency that mutagenesis with EMS was not necessary. The $Ag^r$/$Dc^r$ mutant, RB39, was streaked onto minimal medium containing 10 μg/ml MS. Resistant colonies were obtained and were restreaked for single resistant colonies. One strain, RB46 (pur-60, $Ag^r$-11, $Dc^r$-15, $MS^r$-46) was selected for further study.

Roseoflavin Resistant Mutants

Although many of these $Ag^r$, $Dc^r$ and $MS^r$ mutants were likely to be overproducing GTP, none of them produced levels of riboflavin detectable on plates. In order to deregulate the riboflavin biosynthetic pathway, conditions were determined to select for resistance to the riboflavin analog roseoflavin (Toronto Research Chemical). Maximum killing of cells occurred at 100 μg/ml of roseoflavin in minimal or complete medium; increasing the concentration did not result in any additional killing. Mutations to roseoflavin resistance ($RoF^r$) spontaneously occurred at a sufficiently high rate (approximately $5 \times 10^{-5}$) such that mutagenesis with EMS or other chemicals was not necessary.

Approximately 1000 $RoF^r$ colonies were obtained from each of the strains described above, 1A382, RB36, RB39, RB40 and RB46. $RoF^r$ mutants from all of these strains showed a low level of fluorescence on minimal media plates when exposed to long-wave UV light (366 nm), indicating some riboflavin production. One of the $RoF^r$ colonies obtained from RB46, RB46Y (pur-60, $Ag^r$-11, $Dc^r$-15, $MS^r$-46, $RoF^r$-46), when grown on minimal medium, produced 14 mg/l of riboflavin as determined by HPLC (described above).

Of all the strains treated, only RB39 and RB46 produced a significantly different phenotype when $ROF^r$ colonies were selected. Approximately 0.5% to 1.0% of the $RoF^r$ colonies of either RB39 or RB46 produced an intensely fluorescent, yellow colony. Of these colonies, RB51 (pur-60, $Ag^r$-11, $Dc^r$-15, $RoF^r$-51), arising from RB39, and RB50 (pur-60, $Ag^r$-11, $Dc^r$-15, $MS^r$-46, $RoF^r$-50), arising from RB46, produced a stable, fluorescent-yellow phenotype which correlated with a higher level of riboflavin production, as determined by HPLC. When grown in minimal medium, both RB50 and RB51 produced higher levels of riboflavin in their supernatants than the other $RoF^r$ strains, about 40 mg/l and 30 mg/l, respectively. The lineage of RB50 is depicted in FIG. 5.

Because intensely fluorescent (and thus riboflavin overproducing) colonies could be obtained in non-$MS^r$ strains such as RB51, it appeared that this mutation in general might not be contributing significantly to the higher production phenotype. Both of the other mutations, $Ag^r$ and $DC^r$ ($Ag^r$-11 and $Dc^r$-15 in RB39), appear to be necessary to produce high levels of riboflavin since no intensely fluorescent $RoF^r$ colonies could be found in strains containing only the $Ag^r$-11 (from RB40) or $Dc^r$-15 (from RB36) mutation alone.

guaC Mutations

Another possibly important mutation for achieving overproduction of GTP, and thus riboflavin, is quaC3, which prevents the conversion of GMP back into IMP (see FIG. 2). To construct a strain containing guaC3 that overproduces riboflavin, competent *B. subtilis* strain 62121 cells (guaC3, trpC2, metC7) (Endo et al., *J. Bact.* 15: 169, 1983) were transformed with RB50 DNA and selected for Dc$^r$ on plates containing 100 µg/ml of decoyinine. Thousands of Dc$^r$ colonies resulted. Of 200 colonies which were patched onto Dc$^r$ plates, one was found that exhibited the riboflavin overproduction phenotype (based on UV fluorescence), and was RoF$^r$. This colony was designated RB52 (guaC3, trpC2, metC7, Dc$^r$-15, RoF$^r$-50) and was reserved for subsequent study.

Other Analog-Resistant Mutants

Finally, because mutants resistant to several additional purine analogs also have been reported to be altered in purine metabolism, such mutations were assayed in order to investigate their effect on riboflavin-overproducing strains. It was determined that 500 g/ml of 8-azaxanthine, 1 mg/ml of 6-thioguanine, or 2 mg/ml of sulfaguanidine(Sigma) effectively kills wild-type *B. subtilis*. The azaguanine-resistant, riboflavin-overproducing strains RB50::[pRF8]$_9$ and RB53::[pRF8]$_{90}$ (see below) were found to be already resistant to azaxanthine. Although separate azaguanine- and azaxanthine-resistant mutations with different properties have been described previously, in this case the Ag$^r$-11 and Ag$^r$-53 mutations appear to also convey azaxanthine resistance.

HPLC Analysis of Riboflavin in Crude Supernatants of *B. subtilis*

Accumulation of riboflavin in *B. subtilis* cultures was quantitated by reverse-phase HPLC. Riboflavin standards (Sigma Chemical Co., St. Louis, Mo.) or cell-free supernatants from strains to be tested were fractionated over a 4.6 mm×250 mm Vydac C$_{18}$ column equilibrated with 1% ammonium acetate (pH 6.0). At injection, the column was developed with a linear gradient of methanol and monitored for riboflavin at 254 nm. Authentic riboflavin (i.e. riboflavin "standard") elutes at the mid-point of the gradient.

EXAMPLE 2

Cloning *B. subtilis* Rib Operon

Our general strategy to isolate a restriction fragment containing the rib operon was to screen a "mini" *E. coli* plasmid library of *B. subtilis* DNA by hybridization with a synthetic oligonucleotide probe, the DNA sequence of which was partially derived from the published amino acid sequence for the β subunit of riboflavin synthase (Ludwig et al., *J. Biol. Chem.* 262:1016, 1987). A summary of the protocol is presented in FIG. 6.

A synthetic, 54-base "guess-a-mer" oligonucleotide probe (SEQ ID NO: 17) was used for this screening based on amino acids 84–102 of the 240 amino acid riboflavin synthase protein, sequenced by Ludwig et al. (*J. Biol. Chem.* 262:1016–1021, 1987). The third nucleotide of each codon in the probe was chosen according to estimates made of the most frequent codon usage of *B. subtilis*, based upon, for example, some of the sequences available in GenBank® (Los Alamos Nat. Lab, Los Alamos, N. Mex.). The probe consisted of the following sequence: 5'-GGAGCTACAA-CACATTATGATTATGTTTGCAAT-GAAGCTGCTAAAGGAATTGCT-3'. To test the specificity of the probe, the $^{32}$P-labelled 54-mer DNA was hybridized to nylon filters containing EcoRI-digested chromosomal DNA (Southern, *J. Mol. Biol.* 98:503, 1975) isolated from wild-type and the mutant *B. subtilis* strains. The probe strongly hybridized to a single 9–10 kb fragment of EcoRI-digested *B. subtilis* (rib$^+$ met$^-$) DNA, which is in good agreement with the predicted size of the rib-containing fragment (Osina et al., *FEBS. Lett.* 196:75, 1986). A labelled fragment of the identical size was detected when the probe was hybridized to two mutant strains, RB46 (pur-60, Ag$^r$-11, Dc$^r$-15, MS$^r$-46) and RB50 (pur-60, Ag$^r$-11, Dc$^r$-15, MS$^r$-46, RoF$^r$-50), the latter being a riboflavin overproducer. These hybridization experiments were repeated using HindIII-cut chromosomal DNA, which resulted in the probe identifying a smaller, single fragment of approximately 1.8 kb; this latter result was useful in determining the general location of the rib biosynthetic operon within the cloned DNA.

Isolation of Plasmids pRF1, pRF2 and pRF3, Containing Wild-type rib Biosynthetic Genes A "mini" gene library of 9–11 kb EcoRI fragments from *B. subtilis* strain 168 (rib$^+$) DNA was prepared using pRK290, a low-copy number vector derived from the Pseudomonas replicon RK2 (Ditta et al., *Plasmid* 13:149, 1985). EcoRI fragments (size 9–11 kb) of *B. subtilis* (rib$^+$ met$^-$) DNA were isolated by sucrose (10–40%) rate-zonal centrifugation. A four-fold excess of these fragments (0.22 µg) was ligated to EcoRI-cut pRK290 (0.26 µg), that had been dephosphorylated with calf intestinal alkaline phosphatase (CIAP), at a total DNA concentration of 10 µg/ml. Approximately 10 ng of ligated DNA was transformed into *E. coli* DH5 (F-, endA1, hsdR11 [r$_k$-, m$_k$+], supE$_{44}$, thi-1, λ-, recA1, gyrA96, relA1), resulting in tetracycline-resistant (Tc$^r$) colonies at a frequency of 7.7×10$^4$/µg of DNA. To determine the fraction of transformants containing insert DNA of 9–11 kb, plasmid mini-lysates were prepared from several Tc$^r$ transformants, and their DNA was analyzed by restriction enzyme digestion. About 40% of the Tc$^r$ transformants were found to contain single EcoRI-generated inserts of 9–11 kb.

Approximately 1140 of the Tc$^r$ colonies were screened with the $^{32}$P-labelled 54-mer probe specific for the riboflavin synthase gene. One colony gave a positive signal. Plasmid DNA, designated pRF1, was isolated from this clone and tested for Rib$^+$-marker rescue activity by transforming the DNA into *B. subtilis* 1A210 that contains the riboflavin-deficient mutation rib-2, and selecting for Rib$^+$ prototrophic colonies. pRF1 transformed 1A210 to Rib$^+$ prototrophy at a high frequency. Plasmid DNA from a randomly chosen Tc$^r$ transformant failed to rescue this marker.

Restriction enzyme analysis revealed that pRF1 actually contained two EcoRI-fragment inserts, of 10 kb and 11 kb. To determine which fragment contained the rib operon, EcoRI-digested pRF1 was probed with the $^{32}$P-labelled, 54-mer riboflavin synthase probe. The results indicated that only the smaller, 10 kb fragment cross-reacted with the probe. Moreover, when the 10 kb EcoRI fragment was recloned into the EcoRI site of pBR322, recombinant plasmids pRF2 and pRF3 resulted, representing the two possible orientations of insertion. Both plasmids were found to rescue the rib-2 mutation of *B. subtilis* 1A210 to prototrophy at a high frequency.

Isolation of Plamsids pRF6 and DRF7 Containing rib Biosynthetic Genes From RoF$^r$-*B. subtilis* Strain RB50

RB50 is one of the RoF$^r$ mutants of *B. subtilis*, produced as described above, that is deregulated for riboflavin biosynthesis. It has been reported that approximately 80% of RoF$^r$ mutations reside within the rib operon at the ribo locus (Stepanov, et al., *Genetika* (USSR) 13:490, 1977). Like the wild-type rib operon, rib genes in RB50 were also contained on a 9–10 kb EcoRI fragment; thus this fragment was cloned using the protocol outlined in FIG. 6, with pBR322 used as the cloning vector. Size-selected 9–11 kb EcoRI fragments (0.1 µg) from RB50 were prepared as before and-ligated to a two-fold excess of ends of EcoRI-cut, dephosphorylated pBR322 DNA (0.34 µg) at a total DNA concentration of 22 µg/ml. Approximately 9 ng of ligated DNA was transformed into *E. coli* DH5, resulting in ampicillin-resistant ($AP^r$) colonies at a frequency of $3.5 \times 10^5/\mu g$ of DNA.

Restriction enzyme analysis of plasmid DNA isolated from a sampling of 12 $Ap^r$ colonies revealed that 50% contained plasmids with 9–11 kb EcoRI inserts. Approximately 1140 $AP^r$ colonies were screened with the $^{32}$-P-labelled 54-mer probe specific for the riboflavin synthase gene by colony hybridization. Six colonies gave positive signals. Plasmids pRF6 and pRF7, isolated from two of these six colonies, were identified by restriction enzyme analysis as containing inserts with the same orientation as pRF2 and pRF3, respectively. In addition, both plasmids were able to marker-rescue the rib-2 mutation at high frequencies.

EXAMPLE 3

Introducing Rib$^+$ DNA Into *B. subtilis*

As described supra, the rib operon from both a wild-type strain and a $RoF^r$ mutant of *B. subtilis* were cloned as identical 10 kb EcoRI fragments into the EcoRI site of the *E. coli* replicon pBR322; the derivation of these recombinant plasmids is schematically diagrammed in FIG. 6. To introduce the 10 kb EoRI fragment containing the rib operon into *B. subtilis* in multiple copies, and thus further increase riboflavin production, we constructed a plasmid vector which would allow integration into the *B. subtilis* chromosome. The integrated DNA was amplified by selecting colonies that would grow at high drug concentrations of chloramphenicol.

Construction of and Transformation with International Rib Plasmids pRF4 and pRF8

To construct the international vector, the drug-resistance gene chloramphenicol acetyltransferase (cat), which is selectable in *B. subtilis*, was introduced into pRF2 and pRF6, the pBR322 vectors with the 10 kb fragment from wild-type or $RoF^r$ *B. subtilis* strains, respectively. The plasmids pRF2 and pRF6 were digested with BamHI, which cuts the plasmids uniquely within the pBR322 sequence, and dephosphorylated with CIAP. The cleaved DNA was ligated to a 1.3 kb BamHI fragment containing the cat gene (Youngman et al., *Plasmid* 12: 1–9, 1984), and the ligated DNAs then transformed into *E. coli* DH5 cells (Hanahand, *J. Mol. Biol.* 166: 557, 1983). Approximately 80–90% of the Apr transformants were chloramphenicol resistant ($Cm^r$); restriction analysis of the isolated plasmids (Maniatis et al.) confirmed that plasmid DNA from the $Cm^r$ colonies contained the 1.3 kb fragment. The plasmid containing the wild-type riboflavin fragment and the cat gene was designated pRF4; the plasmid containing the cloned riboflavin fragment from the $ROF^r$ strain was called pRF8. (Since the $RoF^r$ mutation was subsequently shown to be outside the rib operon, these plasmids are presumably identical).

The plasmids pRF4 and pRF8 were transformed into four different *B. subtilis* strains: the riboflavin overproducer RB50 ($Ag^r$-11, $Dc^r$-15, $MS^r$-46, $RoF^r$-50), the RB50 parent RB46 ($Ag^r$-11, $Dc^r$-15, $MS^r$-46), the RB50 parent 1A382, and IS75, a common laboratory strain. Competent IS75 and 1A382 cells were transformed with pRF4 or pRF8; these same plasmids were introduced into RB46 and RB50 by transformation of protoplasts (Chang and Cohen, *Mol. Gen. Genet* 168:111–115, 1979). The pRF4 or pRF8 DNA integrated into each of these four strains was amplified by selecting for colonies that grew at higher chloramphenicol concentrations. In each strain, we were able to obtain colonies that grew in up to 60 µg/ml of chloramphenicol.

In addition, RB52 (guaC3, trpC2, metC7 $Dc^r$-15, $RoF^r$-50), produced by transforming the gauC3 *B. subtilis* strain 62121 with DNA from RB50, was made competent and transformed with pRF8. The integrated plasmid in one of the many $Cm^r$ colonies that resulted was amplified using 90 µg/ml of-chloramphenicol. The resulting cells, RB52::(pRF8)$_{90}$, were grown to mid-log phase and plated on minimal-media containing 500 µg/ml azaguanine. Approximately 20 $Ag^r$ colonies resulted. One such colony seemed to produce a more intense fluorescence. The lineage of this strain, RB53::[pRF8]$_{90}$, is given in FIG. 7.

EXAMPLE 4

Riboflavin Overproduction by Strains Containing pRF4 or pRF8

RB50 containing pRF4 or pRF8 displayed the riboflavin overproduction phenotype (yellow and UV-fluorescent colonies). Amplification of the rib$^+$ DNA in a wild-type strain or the parent strains of RB50 did not yield yellow or UV-fluorescent colonies, a finding that indicates that the $RoF^r$ mutation (which deregulates the biosynthesis of riboflavin) is required for chromosomal amplification of wild-type DNA to cause riboflavin overproduction. A series of shake flask fermentations were performed in 25 ml of riboflavin minimal medium (RMM, in Table I) in a 300 ml baffled flask (Bellco) to measure the production of riboflavin from RB50 that contained the integrated and amplified rib operon.

TABLE I

| COMPOSITION OF MEDIA | |
|---|---|
| RMM | g/l |
| Sodium glutamate | 2.0 |
| Casamino acids (Difco) | 0.2 |
| Yeast extract (Difco) | 0.2 |
| $KH_2PO_4$ | 6.0 |
| $K_2HPO_4$ | 14.0 |
| $(NH_4)_2SO_4$ | 2.0 |
| Sodium citrate | 1.0 |
| $MgSO_4 \cdot 7H_2O$ | 0.2 |
| Adenosine | 0.05 |
| (adjusted to pH 7.0 and autoclaved) | |
| Maltose | 15.0 |
| (added as sterile 20% solution after autoclaving) | |

The fermentations were run with strains RB46, RB50 and RB50 containing pRF4 amplified by selection for resistance to 30 µg/ml of chloramphenicol (RB50::[pRF4]$_{30}$) and 90 µg/ml of chloramphenicol (RB50::[pRF4]$_{90}$). At 24 and 48 hours, supernatant samples were removed and measured for riboflavin content by reverse-phase HPLC.

As shown in Table II, RB50::(pRF4)$_{30}$ produced 0.3 g/l of riboflavin, and RB50::(pRF4)$_{90}$ produced 0.7 g/l of riboflavin, in 48 hours, which is significantly more than that produced by the strains without rib amplification, such as RB46 and RB50.

TABLE II

QUANTITATIVE ANALYSIS OF RIBOFLAVIN-
CONTAINING SUPERNATANTS FROM *B. SUBTILIS*

| Strain | Culture Time (hours) | Riboflavin* (g/l) |
|---|---|---|
| RB46 | 24 | 0.009 |
| RB50 | 24 | 0.02 |
| RB50::[pRF4]$_{30}$ | 24 | 0.1 |
| RB50::[pRF4]$_{90}$ | 24 | 0.4 |
| RB46 | 48 | 0.007 |
| RB50 | 48 | 0.05 |
| RB50::[pRF4]$_{30}$ | 48 | 0.3 |
| RB50::[pRF4]$_{90}$ | 48 | 0.7 |

*Riboflavin was measured using an HPLC assay.

The dramatic increase in riboflavin production resulting from amplification of rib genes in the deregulated host argues that information encoded by the cloned DNA is rate-limiting for riboflavin biosynthesis.

EXAMPLE 5

Mapping the RoF$^r$-50 Mutation

The RoF$^r$-50 mutation in RB50 appeared to be critical to the riboflavin-overproduction phenotype. To identify and possibly move the mutation into different strain backgrounds it was necessary to map the location of the RoF$^r$-50 mutation on the *B. subtilis* chromosome. Since pRF4 and pRF8 gave very similar-levels of riboflavin production in all strain backgrounds, it seemed unlikely that the ROF$^r$-50 mutation was located on the cloned 10 kb EcoRI, rib-containing fragment. More likely, the RoF$^r$-50 mutation is an unlinked repressor-type mutation, possibly in ribC, a repressor mutation which has been reported to map in the lys-aroD region of the *B. subtilis* chromosome (Chernik et al., *Genetika* (USSR) 15:1569, 1979). To determine whether the RoF$^r$-50 mutation was linked or unlinked to the, riboflavin operon, competent *B. subtilis* 1A210 (rib-2) cells were transformed with RB50 DNA, selecting for rib$^+$. Thousands of rib$^+$ colonies resulted, and 200 colonies were patched onto tryptose blood agar base containing 100 g/ml of roseoflavin. No RoF$^r$ colonies resulted, and none of the colonies exhibited the riboflavin overproduction phenotype, confirming that the RoF$^r$-50 mutation is not located in the rib operon.

EXAMPLE 6

Locating rib$^+$-Biosynthetic Genes Using CAT Insertional Mutagenesis

FIG. 4 contains a restriction map of the rib-containing 10 kb EcoRI fragment of pRF2, prepared according to standard procedures. Restriction enzyme sites for XbaI, BglII, SstI, HpaI and NcoI are unique to the insert DNA, whereas SalI and PstI cut once in the insert and once in the vector; the insert does not contain any BamHI, XhoI or NheI restriction sites. Restriction enzyme HindIII cleaves the insert at multiple sites; the 54-mer probe specific for the riboflavin synthase gene hybridized to an approximately 1.8 kb HindIII fragment, suggesting that the rib operon must also reside in the general area surrounding the SalI and left-most BglII (BglII$_L$) sites.

In general, to determine the boundaries of the rib operon, small cat-containing restriction fragments were used to construct insertions and deletions in the rib$^+$-cloned DNA fragment of pRF2.

*E. coli* plasmid pEcc1 served as the primary source of restriction fragments bearing a cat gene which confers chloramphenicol-resistance in both *E. coli* and *B. subtilis*. This plasmid, a derivative of pMI1101 (Youngman et al., Plasmid 12:1–9, 1984) in which a non-essential region of the plasmid was removed by standard recombinant DNA techniques, contains a 1.3 kb cat-containing fragment flanked by the "polylinkers" of M13mp7, and therefore is capable of generating cat cassettes with either SmaI, EcoRI, SalI, or BamHI ends. To generate SstI or XbaI-ended fragments containing the cat gene, the 1.3 kb cat-containing BamHI fragments of pEcc1 was isolated, the ends modified with HindIII linkers, and the modified fragment cloned into the HindIII site within the polylinker region of pIC10R, generating plasmid pEcc4.

Integrative plasmid derivatives were first constructed in *E. coli* and then transferred to the rib chromosomal locus of *B. subtilis* by DNA transformation. This was done by linearizing the plasmid by a restriction enzyme cut outside the cloned DNA insert, transforming competent *B. subtilis* strain 1A382 or PY79 (SPβ$^c$, SPβ$^c$ rib$^+$) cells with this cut DNA, and selecting for Cm$^r$. Because the pBR322 replicon is unable to replicate in *B. subtilis*, and the cat gene is bounded on both sides by sequences homologous to the rib$^+$ locus, the cat-containing insertion or deletion can only be inserted into the chromosome by a double-crossover recombination event to yield Cm$^r$ transformants. To determine whether the insertion or deletion inactivated riboflavin synthesis, Cm$^r$ colonies were assessed for growth on minimal medium agar plates with or without the presence of riboflavin (Rib phenotype).

As diagrammed in FIG. 8, cat-containing restriction fragments were inserted by ligation into the individual restriction sites for XbaI, SstI, SalI and BglII of pRF2, inserted between the pair of BglII or NcoI sites (generating deletions removing either a 2.0 kb BglII fragment or a 0.8 kb NcoI fragment) or inserted into single HaeIII and EcoRV sites of the approximately 1.8 kb HindIII fragment that hybridized to the rib-specific DNA probe, according to standard techniques. The results are shown in Table III.

TABLE III

CHARACTERIZATION OF INSERTION AND
DELETION DERIVATIVES OF rib$^+$ DNA

| Insertion derivative[a] | *B. subtilis*[b] Riboflavin Phenotype |
|---|---|
| A(XbaI) | |
| r | + |
| l | ND |
| B(SstI$_L$) | |
| r | + |
| l | ND |
| C(SstI$_R$) | |
| r | — |
| l | — |
| D(BglII$_L$) | |
| r | — |
| l | — |
| E(SalI) | |
| r | — |
| l | — |
| F(BglII$_R$) | |
| r | — |
| l | — |
| G(HaeIII) | |
| r | ND |
| l | + |

TABLE III-continued

CHARACTERIZATION OF INSERTION AND
DELETION DERIVATIVES OF rib± DNA

| | B. subtilis[b] Riboflavin Phenotype |
|---|---|
| H(EcoRV) | |
| r | + |
| l | ND |
| Deletion derivative | |
| Bgl | |
| r | — |
| l | — |
| Nco | |
| r | + |
| l | + |

[a]"r" (right) and "l" (left) identify the transcriptional orientation of the inserted cat gene relative to the restriction map in FIG. 8.
[b]B. subtilis strain 1A382 (rib+, trpC2, pur-60, hisH2) or PY79 (SP β[c], rib+)

As summarized in FIG. 8 and Table III, insertions into the SalI, either BglII, or the "right most" SstI (SstI$_R$) sites, or deletion of the 2.0 kb BglII fragment, all generated Cm[r] colonies that could not produce riboflavin. (Rib−), indicating that the rib operon was centrally located within the cloned DNA. Significantly, removal of the 0.8 kb NcoI fragment apparently had no effect on riboflavin production (Rib+), suggesting that one end of the rib gene cluster was located to the left of the "left most" NcoI (NcoI$_L$) site. The other end of the rib operon was initially determined to map within the approximately 1.8 kb HindIII fragment because the two insertions at sites within the fragment, EcoRV and HaeIII, as well as sites distal to the fragment, XbaI and SstI$_L$, all generated Cm[r] colonies that produced riboflavin.

EXAMPLE 7

Nucleotide Sequence of the Rib Operon

Based on the cat-insertional mutagenesis of the cloned 10 kb DNA fragment, the entire rib operon was localized within a 6.0 kb region bounded by the SstI$_L$ and NcoI$_L$ sites.

This 6.0 kb region of pRF2 containing the rib operon and flanking regions was sequenced by the dideoxy method of Sanger et al. (*Proc. Natl. Acad. Sci. USA* 74:5463, 1977). Briefly, M13 clones for sequencing were prepared either by subcloning specific restriction fragments into M13, by using the exonuclease activity of T4 DNA polymerase to generate a series of overlapping deletions (Dale et al., *Plasmid* 13:31, 1985), or by "shot-gun" cloning random fragments, from sonicated restriction fragments, into M13. In some cases, the nucleotide sequence across a restriction site juncture of adjacent fragments was also determined by primer extension sequencing. Approximately 5500 bp were sequenced on both strands and analyzed for sequences. resembling typical open reading frames with gram positive-bacteria ribosome binding sites, gram-positive promoters and rho-independent transcription termination sites.

Analysis revealed six complete, non-overlapping open reading frames (FIG. 3): ORF 2 (124 amino acids), the gene coding for the β subunit of riboflavin synthase (154 amino acids), ORF 3 (398 amino acids), ORF 4 (215 amino acids), ORF 5 (361 amino acids) and ORF 6 (105 amino acids). Each ORF was preceded by a strong Bacillus ribosome binding site (RBS) with calculated thermostability ranging from ΔG=−16 to −22 kcal/mol, and all of them were oriented in the same transcriptional direction. In addition, within the coding region of ORF 5, a second RBS site and ATG start codon were identified, potentially encoding a smaller protein of 248 amino acids. However, based on S-30 in vitro coupled transcription/translation reactions (see below), ORF 5 appears to encode only a 361 amino acid protein. Finally, part of another coding region, ORF 1, encoding the last 170 amino acids of a protein and oriented in the opposite direction, was also identified.

Based on the following observations, riboflavin biosynthesis in *Bacillus* is controlled by a single operon containing 5 genes: the β riboflavin synthase gene, ORF 2, ORF 3, ORF 4, and ORF 5, of which at least four, the β-riboflavin synthase gene, ORF 3, ORF 4 and ORF 5, unambiguously encode biosynthetic enzymes, with the remaining one, ORF 2, possibly encoding a biosynthetic enzyme.

1. ORF 3, ORF 4 and ORF 5 overlap restriction enzyme sites where insertion of cat-containing restriction fragments caused inactivation of riboflavin production in *B. subtilis* (FIGS. 4 and 8).

2. ORF 1 overlaps a restriction enzyme site(s) where insertion of cat-containing restriction fragments did not cause inactivation of riboflavin production in a rib+ *B. subtilis* strain (Table III and FIG. 8), nor did it cause reduction of riboflavin production in the deregulated, ROF[r] *B. subtilis* strain RB52.

3. ORF 2 also overlaps a restriction enzyme site, EcoRV, where insertion of cat-containing restriction fragments did not-cause inactivation of riboflavin production in a rib+*B. subtilis* strain (Table III and FIG. 8). However, such an insertion did cause a detectable reduction of riboflavin production in the deregulated, RoF[r] *B. subtilis* strain RB52, indicating that the mutated ORF 2 gene product was partially inactive for riboflavin production. The results suggest that ORF 2 does encode a rib-specific enzyme.

4. Two DNA sequences capable of forming stem-loop structures indicative of rho-independent transcriptional termination sites were identified within the intercistronic gaps between ORF 1 and ORF 2 and between ORF 5 and ORF 6 (FIGS. 4 and 9). Removal of structures between ORF5 and ORP6 enhances expression of riboflavin. The structures impart riboflavin sensitivity to lacZ-fusion constructs; thus, they can be used to impart such sensitivity to any other gene to which they are fused at the 5'-end upstream of the promoter.

5. A DNA sequence, TTGCGT-(17bp)-TATAAT (nucleotides 770–799 of SEQ ID NO: 1), resembling the promoter recognized by the σ[A] (vegetative form) of *B. subtilis* RNA polymerase was identified approximately 290 bp upsteam from ORF 5, oriented in the same transcriptional direction as ORF 5 (FIG. 4). A transcriptional fusion of this promoter (P$_1$, on a 1.1 kb BglII-NcoI restriction fragment) to a promoterless *E. coli* lacZ gene (P$_1$-lacZ) displayed riboflavin-regulated expression of β-galactosidase activity in a rib+, *B. subtilis* strain (62121) and high-level, constitutive (unregulated) expression of β-galactosidase activity in a rib+, RoF[r] *B. subtilis* strain (RB52) only when the promoter was oriented in the same transcriptional direction as the gene, as shown in Table IV. Primer extension analysis was used to confirm the start site. Transcriptional and Northern analyses were used to show a polycistronic RNA of 4.2 kb encompasses the entire rib operon.

TABLE IV

RIBOFLAVIN-REGULATED EXPRESSION OF P₁-LacZ TRANSCRIPTIONAL FUSIONS

| Strain (integrated plasmid) | β-Galactosidase Specific Activity (Miller Units) | |
|---|---|---|
| | +Riboflavin (2 μg/ml) | −Riboflavin |
| B. subtilis 62121 (P$_1$-lacZ$^a$) | 1.3 | 4.2 |
| B. subtilis RB52 (P$_1$-lacZ$^a$) | 31 | 38 |
| B. subtilis 62121 (P$_1$-lacZ$^b$) | <0.1 | <0.1 |
| B. subtilis 62121 | <0.1 | <0.1 |

[a]P$_1$ and lacZ oriented in the same direction
[b]P$_1$ and lacZ oriented in opposite directions
Based on these results, this σ$^A$ promoter, P$_1$, is a primary promoter for transcription of ORF 5, ORF 4, ORF 3, β-riboflavin synthase gene and ORF 2.

6. A second DNA sequence, TTGAAG-(17bp)-TACTAT (nucleotides 2528–2556 of SEQ ID NO: 1), resembling a promoter recognized by the σ$^A$ (vegetative form) of B. subtilis RNA polymerase was identified within the 3' end of ORF 4, approximately 295 bp upstream from ORF 3 and oriented in the same transcriptional direction as ORF 3(FIG. 4). Integration into B. subtilis by a Campbell-type recombination event of an E. coli plasmid containing this promoter sequence on a 0.7 kb SalI-BglII restriction fragment did not cause inactivation of riboflavin production in B. subtilis, results which indicated that this second sequence (P$_2$) has promoter activity and thus may actually control transcription (in addition to the σ$^A$ P1 promoter) of ORF 3, the β subunit riboflavin synthase gene and ORF 2. LacZ fusions and Northern analysis confirmed the existence of this promoter.

7. A third DNA sequence, TTGAAT-(18bp)-TAAAAA (nucleotides 4545–4574 of SEQ ID NO: 1), possibly resembling the promoter recognized by the σ$^A$ (vegetative form) of B. subtilis RNA polymerase was identified within the intercistronic region between the β subunit of the riboflavin synthase gene and ORF 2, approximately 83 bp upstream of ORF 2 and oriented in the same transcriptional direction (FIG. 4). This σ$^A$ promoter, P$_3$, may also control transcription of ORF 2, in addition to P$_1$ and P$_2$.

8. In vitro-coupled transcription/translation analysis of S-30 reactions of the cloned DNA confirmed that ORF 2, ORF 3, ORF 4, and ORF 5 all actually encoded proteins of the size predicted from their respective sequences.

9. Three of the five presumed enzymatic steps in riboflavin biosynthesis were assigned to specific coding regions by comparing predicted amino acid sequences or molecular weights of their products to published protein sequences, using GenBank®, or known protein sizes.

a. The putative protein encoded by the open reading frame between ORF 2. and ORF 3 almost identically matched the published 154 amino acid sequence of the β subunit for the riboflavin synthase enzyme (Ludwig et al., *J. Biol. Chem.* 262:1016, 1987). Only one amino acid difference was detected: lysine was substituted for glycine at residue 65. This enzyme is reported to catalyze the formation of 6,7-dimethyl-8-ribityllumazine from 5-amino-6-ribitylamino-2,4(1H,3H)-pyrimidinedione-5'-phosphate (FIG. 1, structures 5 and 4, respectively) and 3,4-dihydroxybutanone-4-phosphate.

b. A 39% identity in an 88-amino acid overlap was identified between the putative product of ORF5 and deoxycytidylate deaminase, a 188 amino acid protein encoded by the E. coli bacteriophage T$_2$ (Maley et al., *J. Biol. Chem.* 258:8290, 1983). Based on this result, ORF 5 most likely encodes the rib-specific deaminase that catalyzes the formation of 5-amino-6-(ribosylamino)-2,4(1H,3H)-pyrimidinedione-5'-phosphate from 2,5-diamino-6-(ribosylamino)-4(3H)-pyrimidinone-5-phosphate (FIG. 1, structures 3 and 2, respectively).

c. The predicted molecular weight of the ORF 4 gene product (26,000 Da) was in good agreement with the molecular weight of the α-subunit for riboflavin synthase. (23,000 Da; Bacher et al., *J. Biol. Chem.* 255: 632, 1980). Based on this result, ORF 4 encodes the α-subunit for riboflavin synthase, which catalyzes the final step of the biosynthetic pathway: dismutation of 6,7-dimethyl-8-ribityllumazine to riboflavin (FIG. 1, structures 5 and 6, respectively) and 5-amino-6-ribitylamnio-2,4(1H,3H) -pyrimidinedione.

10. The remaining enzymatic steps in riboflavin synthesis were tentatively assigned to coding regions by aligning the position of ORFs to a physical map of rib mutations in the operon (Morozov et al., *Mol. Genet. Mik. Virusol.* no. 7:42 (1984)). Mutations for defective GTP cyclohydrolase were reported to map to the 0.5 kb HindIII fragment. Since ORF 3 encompasses this restriction fragment, we concluded that ORF 3, at least in part, encodes this enzymatic function, which catalyzes the formation of 2,5-diamino-6-(ribosylamino)-4(3H)-pyrimidinone-5'-phosphate from GTP (FIG. 1, structures 2 and 1, respectively). In addition, the biosynthetic gene encoding a rib-specific reductase was reported to be contained entirely within the approximately 1.8 kb HindIII fragment. Since this fragment contains only two complete coding regions, the β subunit of the riboflavin synthase gene and ORF 2, we speculate that ORF 2 encodes the reductase, which catalyzes the formation of 5-amino-6-(ribitylamino)-2,4(1H,3H)-pyrimidinedione-5'-phosphate from 5-amino-6-(ribosylamino)-2,4(1H,3H)-pyrimidinedione-5'-phosphate (FIG. 1, structures 4 and 3, respectively).

In addition, a similar rho-independent transcription termination site was detected in the apparent leader region of the operon, downstream of the putative σ$^A$ P$_1$ promoter but just upstream of the first coding region of the operon, ORF 5 (FIGS. 4 and 9). This potential terminator structure may be involved in regulation of the rib operon by a termination/anti-termination mechanism. In addition, a roseoflavin-resistant (R$_O$F$^R$) dependent regulatory region is present on a 0.7 kb SalI-BglII restriction fragment of ORF3.

Assignment of Rib ORFs to Protein Products

One method for confirming whether the rib-specific ORFs encode proteins is to "visualize" the size and number of proteins synthesized from the cloned DNA in an S-30 in vitro coupled transcription/translation reaction using pRF2 and its various derivatives as templates. The S-30 fraction kit (New England Nuclear; used according to manufacturer's specifications) is especially efficient in translating B. subtilis genes due to the presence of their strong ribosome binding sites.

Using the cloned 10 kb EcoRI fragment of pRF2 or pRF4 as templates, we expected to detect five putative rib-specific proteins: β riboflavin synthase, 14.7 kilodaltons (kd) (Ludwig et al., *J. Biol. Chem.* 262:1016, 1987); and the proteins from ORF 2, 13.6 kd; ORF 3, 43.7 kd; ORF 4, 23 kd; and ORF 5, 39.7 kd. We also expected to detect at least two other proteins, encoded by ORF 6 (11.6 kd) and ORF 1 (at least 18.7 kd), as well as any additional proteins encoded by genes present in the unsequenced regions of the 10 kb cloned DNA fragment. In addition, vector-associated proteins, including the bla and cat antibiotic resistance gene products, were also expected (the tet gene is not strongly expressed in S-30 reactions).

Excluding the bla- and cat-specific proteins (32 kd and 18 kd, respectively) and other vector-associated proteins, a total of six major $^{35}$S-labelled proteins were detected, with molecular weights of 47 kd, 44 kd, 38 kd, 26 kd, 20 kd and 15 kd, on a 15%-SDS polyacrylamide gel of the S-30 reactions with pRF2 or pRF4. To assign these protein products to their corresponding rib-specific ORFs, S-30 reactions were repeated using various available deletion derivatives, cat-insertion derivatives, and subcloned fragments of the 10 kb EcoRI cloned DNA (FIG. 10). The results are shown in Table V.

TABLE V

RIB-SPECIFIC PROTEINS OBSERVED IN S-30 REACTIONS

| Plasmid | 47,000 Daltons (ORF 3) | 44,000 Daltons (ORF 5) | 26,000 Daltons (ORF 4) | 15,000 Daltons (ORF 2) |
|---|---|---|---|---|
| pRF2 | + | + | + | + |
| pRF4 | + | + | + | + |
| pRF21 | − | − | + | − |
| pRF5 | − | − | − | + |
| pRF29 | − | − | − | − |
| pRF12 | + | − | + | + |
| pRF10 | − | − | − | − |
| pRF38 | − | − | − | − |
| pRF24/pRF20 | − | + | + | + |
| pRF23 | + | − | + | + |

Based on these results, protein products were assigned to ORF 3 (47 kd); ORF 5 (44 kd); ORF 4 (26 kd); and ORF 2 (15 kd), with molecular weights in close agreement with the predicted sizes.

The assignment of products to ORF 2 and the β riboflavin synthase gene were less straightforward than the assignments to the other ORFs. Since the S-30 reaction of pRF2 produced a 15 kd protein which was close to the predicted size of the proteins encoded by either gene, it was first assumed that this protein band actually contained both protein species. However, the cat insertion into ORF 2 in plasmid pRF38 completely; removed this protein band, replacing it with a much smaller protein of 6 kd, which is in close agreement with the predicted size of the truncated ORF 2. Based on these results, the 15 kd protein appears to be generated only by ORF 2. It is not clear why the β riboflavin synthase protein is not visualized on the gels of the S-30 reactions. Taken in total, however, the results confirmed the existence of five rib-specific coding regions: ORF 5, ORF 4, ORF 3, ORF 2 and the β riboflavin synthase gene.

In addition, ORF 1 appeared to encode a 38 kd protein, while no product was identified for ORF 6.

Regulatory Mechanisms of the Rib Operon

In *B. subtilis*, a recurring pattern of gene organization and regulation for biosynthetic pathways has been observed by several investigators. The nucleotide sequences of the tryptophan biosynthetic pathway (Henner et al., *Gene* 34:169, 1984) and the de novo purine nucleotide pathway (Ebbole and Zalkin, *J. Biol. Chem.* 262:8274, 1987) of *B. subtilis* both contain clustered, overlapping genes transcribed as a polycistronic message and regulated at least in part by a novel transcription termination/anti-termination mechanism, involving a repressor protein which can be encoded by a gene unlinked to the biosynthetic operon (Zalkin and Ebbole, *J. Biol. Chem.* 263:1595, 1988). Since we found that the organization of the rib biosynthetic and regulatory genes is strikingly similar to those of the *B. subtilis* trp and pur pathways, we hypothesized that the rib operon might be regulated, at least in part, in a similar manner.

Briefly, the key characteristics of the transcription termination/anti-termination model include (Shimotsu et al., *J. Bacteriol.* 166:461, 1986): (i) the presence of a long 5' leader sequence that precedes the first gene in the operon; (ii) the presence in the RNA leader of two or more overlapping dyad symmetries that have the potential to form mutually exclusive RNA stem-loops, one structure functioning as a rho-independent transcription terminator and the other as an "anti-terminator" (blocking the formation of the rho-independent transcription terminator); (iii) under repressive conditions, the repressor protein, activated by the end product of the pathway, binds to the nascent mRNA at a site which prevents formation of the anti-terminator, thus allowing formation of the terminator which terminates transcription; (iv) under derepressive conditions, binding of the unactivated repressor is precluded, resulting in the formation of the anti-terminator causing read-through transcription into the coding region of the operon.

As discussed above, the most likely site for initiation of transcription in the rib operon is a $\sigma^A$ promoter, $P_1$, located about 290 bp upstream from the first gene in the operon. Preliminary analysis of the RNA leader sequence indicated that it contained most, if not all, of the structures required for regulation by the termination/anti-termination model. Within this region, a stem-loop structure followed by a string of thymidines resembling a rho-independent transcription terminator was identified approximately 50 bp upstream of ORF 5; this sequence has the potential to form a hairpin with a $\Delta G$ of −26 kcal/mol (FIG. 9). In addition, several potential stem-loop structures with $\Delta G$'s ranging from −13 to −16 kcal/mol were located within the rib 5' leader that could possibly qualify as the anti-terminator sequence.

In addition to the primary site for the initiation of transcription, usually located upstream from the first gene in the operon, there exist in some biosynthetic pathways secondary promoter sites located within the internal regions of the operon. The possibility of there being a second promoter site within the rib locus was also suggested by previous R-loop heteroduplex studies of the rib operon (Osina et al., *FEBS Letters* 196:75–78, 1986), showing two or more sites for the initiation of mRNA synthesis. Our preliminary analysis of the intercistronic gaps of the rib operon did not detect such secondary promoter sites. However, when this analysis was extended to all of the sequences within the operon, another $\sigma^A$ promoter, $P_2$, was identified within the 3' end of ORF 4, just downstream from the SalI restriction site (FIG. 4). Thus it is possible that the expression of ORF 2, ORF 3, and the β-subunit for riboflavin synthase is also under the control of this secondary promoter. In addition, a possible third $\sigma^A$ promoter, $P_3$, was identified just upstream of ORF 2. Therefore ORF 2 is possibly also under the control of this additional promoter.

The location of putative coding regions, promoters and transcription termination sites on the DNA sequence of the 5.5 kb *B. subtilis* rib-specific region is shown in Table VI.

TABLE VI

CODING REGIONS, PROMOTER, AND TRANSCRIPTION TERMINATION SITES OF THE *B. SUBTILIS* RIB OPERON

|  |  | bp Number[a] |
|---|---|---|
| Coding Regions | ORF 6 | 364–678 |
|  | ORF 5 | 1101–2183 |
|  | ORF 4 | 2197–2841 |
|  | ORF 3 | 2859–4052 |
|  | β riboflavin-synthase gene | 4088–4549 |
|  | ORF 2 | 4665–5036 |
|  | ORF 1 | 5567–5057[b] |
| $\sigma^A$ Promoters | $P_1$ | 771–799 |
|  | $P_2$ | 2528–2556 |

TABLE VI-continued

CODING REGIONS, PROMOTER, AND
TRANSCRIPTION TERMINATION SITES
OF THE *B. SUBTILIS* RIB OPERON

| | | bp Number[a] |
|---|---|---|
| | P$_3$ | 4545–4574 |
| rho-Independent Termination Sites | Upstream from 5' promoter | 708–748 |
| | Within 5' leader RNA | 1034–1067 |
| | At 3' end of rib operon | 5038–5090 |

[a] of FIG. 3.
[b] Coding region oriented in opposite direction.

EXAMPLE 8

Construction of Vectors Containing a Modified Rib Operon

The above functional analysis of the rib operon of *Bacillus subtilis* for the first time delimiting the regulatory regions and open reading frames in the nucleotide sequence permits construction of new vectors which are useful for increasing the yield of riboflavin production. The knowledge of the location of the specific genes required for riboflavin biosynthesis, of the location of transcriptional control regions, and other relevant regions (e.g., RBS) in those genes allows changes in such regions to be made. There follow a few examples of such manipulations.

Construction of an Integration Plasmid with a Rib Operon on a Smaller DNA Fragment The integrating vector used to construct the riboflavin overproducing strain RB50::[pRF8] contains a 10 kb EcoRI fragment including the rib operon. Since the rib operon appears to occupy less than 6 kb of DNA a new integration vector was constructed (pRF40) containing the rib operon on a smaller DNA fragment. The smaller size of this clone allows higher amplification of rib genes resulting in higher yields of riboflavin.

Referring to FIG. 12, pRF40 was constructed from pRF36 which is a plasmid in which the 0.8 kb NcoI fragment of pRF2 is replaced with a cat gene. The rib operon is contained on a 6.5 kb XbaI-EcoRI fragment. This fragment was isolated and ligated to pUC19 (Yanisch-Perron et al., 33 *Gene* 103, 1985; available from New England Biolabs, Boston, Mass., and Bethesda Research Laboratories, Maryland) digested with XbaI and EcoRI. The ligated DNA was transformed into DH5α *E. coli* and plated onto LB plates containing 40 µg/ml X-gal and 50 µg/ml ampicillin. Analysis of miniprep DNA prepared from white colonies indicated that pRF39 contained the 6.5 kb XbaI-EcoRI fragment.

pRF39 was digested with EcoRI, treated with CIAP, and then ligated to a 1.6 kb EcoRI fragment containing the cat gene. The ligated DNA was then transformed into DH5α *E. coli* and appropriate colonies selected for plating onto LB +10 µg/ml chloramphenicol; two colonies were chloramphenicol-resistant. Analysis of miniprep DNA prepared from these colonies confirmed the presence of the cat gene. One of these plasmids is pRF40 (FIG. 14).

Construction of Plasmids Containing Transcriptionally Modified Rib Operon

As described above, it is useful to replace the promoter and operator regions of the riboflavin operon with promoters allowing constitutive expression of the riboflavin biosynthetic genes. Plasmids containing such constructs can then be used to produce bacterial strains which will produce increased levels of riboflavin. A few examples, not limiting in the invention, are provided below.

Referring to FIG. 13, the riboflavin promoter and regulatory region were removed and replaced with an SPO1 promoter. We took advantage of the BglII site located at position 1130 at the start of ORF3. Oligonucleotides were synthesized (RB5 and RB6, see FIG. 18) that recreated the DNA sequence 5' to the BglII site (the first few amino acids of ORF5 and the SD sequence) up to position 1058. Reconstruction of the 5'-end of the operon stopped before any of the proposed DNA regulatory structures (FIG. 13). At their 5' ends the oligonucleotides contained BamHI, NsiI, and EcoRI restriction sites, allowing for placement of various promoters 5' to the rib operon. Because of the various restrictions sites in the rib operon it was necessary to construct the operon with the new promoters in several steps, as follows.

A 1.4 kb SalI-BglII fragment was isolated from pRF36 (FIG. 13). This fragment was ligated with the two oligonucleotides and EcoRI-SalI-digested pUC19. The ligated mixture was then transformed into *E. coli* DH5α cells and plated onto LB containing 50 µg/ml ampicillin and 40 µg/ml X-gal. Minipreps were prepared from AP$^r$ white colonies; one plasmid having the desired structure is pRF46 (FIG. 13).

pRF46 was digested with BamHI and SalI and the 1.4 kb fragment isolated. This fragment was then ligated with the 400 bp EcoRI-BamHI fragment of pNH202 (pUC8 containing the SPO1-15 promoter, Lee and Pero, *J. Mol. Biol.*, 152:247–265, 1981) and pUC19 cut with SalI and EcoRI. The ligated DNA was then transformed in DH5α *E. coli*, which were plated onto LB+ampicillin+X-gal. Miniprep DNA was prepared from white colonies; and pRF48 had the desired structure (FIG. 13).

pRF48 was digested with EcoRI and SalI and the 1.8 kb fragment isolated. This fragment was ligated with the 4.0 kb XbaI-SalI fragment (containing the rest of the rib operon) from pRF2 and XbaI, EcoRI-cut pUC19. The ligated mixture was then transformed into *E. coli* DH5α cells which were plated on LB+ampicillin+X-gal. Miniprep DNA was prepared from white colonies; pRF49 had the desired structure, and supernatants from culture containing this plasmid was yellow, indicating riboflavin production (FIG. 13).

To place the cat gene in pRF49, to allow selection in *B. subtilis*, the plasmid was digested with XbaI and ligated to a 1.3 kb cat-containing XbaI fragment from pEcc4. The ligated DNA was transformed in *E. coli* DH5 cells. Hundreds of Ap$^r$ colonies resulted, and the colonies were patched onto plates containing LB +10 µg/ml chloromphenicol. Approximately 10% of the colonies grew on the chloramphenicol plates, indicating the presence of the cat gene. One cat-containing plasmid is called pRF50 (FIG. 14).

The above example shows placement of a new promoter upstream of ORF5. We found that it is also useful to place a promoter after P$_2$ between ORF3 and ORF4 in order to further increase riboflavin production. An example off such construction now follows.

Referring to FIGS. 14 and 15, to place a copy of the SPO1-15 promoter upstream of ORF3 we made use of the restriction sites adjacent to the ORF4-ORF3 junction. The ClaI site at position 2767 is located at the end of ORF4 and is unique in the rib operon. Another useful restriction site near the beginning of ORF3 is the DraI site at position 2892. Oligonucleotides were synthesized that recreated the sequence from the above-mentioned DraI site past the start of ORF3 and placed a unique BamHI site before the beginning of ORF3 (linkers P2-A and P2-B, FIG. 18). Another set of oligonucleotides recreated the sequence from the ClaI site past the end of ORF4 and placed an EcoRI site at that location (linkers P2-CII and P2-DII, FIG. 18). The SPO1-15 promoter, located on a EcoRI-BamHI fragment, was then be placed between the BamHI and EcoRI sites created by the oligonucleotides. The entire operon was put together with this additional SPO1-15 promoter as follows.

Referring to FIG. 15, the 750 bp SalI-BglII fragment containing the ORF4-0RF3 function was subcloned to pIC2OR (Marsh et al., Gene 32:481–485, 1984). The resulting plasmid, pRF57, was then digested with DraI and BglII, and the predicted 270 bp DraI-BglII fragment was isolated. This fragment and linkers P2-A and P2-B were ligated to pIC2OR cut with SalI and BglII. The linkers placed BamHI and SalI sites upstream of the 5' end of ORF3. (The SalI site was chosen for convenience since BglII and BamHI sites are compatible and will be removed later.) The ligation was transformed into *E. coli* DH5α cells. Plating onto LB medium+Amp and X-gal resulted in white colonies; pRF58 had the desired structure. The 330 bp BglII-SalI fragment from pRF58 was isolated and ligated with 3.3 kb BglII-XbaI fragment containing the 3'-end of the rib operon from pRF36 (FIG. 12) and PUC19 cut with XbaI and SalI. The ligated DNA was then transformed into *E. coli* DH5α cells, resulting in white colonies; pRF62 (FIG. 15) had the desired structure. For convenience, the 3.6 kb BamHI-XbaI fragment was isolated from pRF62 and subcloned into BamHI-, XbaI-cut pUC19 (PRF64, FIG. 15). This plasmid now contained the 3.6 kb 3'-end of the rib operon with an engineered BamHI site preceding ORF3.

To place the SPO1-15 promoter in front of the 3'-half of the rib operon containing the last three open reading frames, we digested pRF64 with EcoRI and BamHI and ligated it to a 400 bp EcoRI-BamHI fragment containing the SPO1-15 promoter. The ligated DNA was transformed into *E. coli* DH5 cells and miniprep DNA was prepared; pRF65 has the desired structure.

The SPO1-15 promoter was than engineered to place a ClaI site upstream of the promoter to reconstruct the end of ORF4. The EcoRI-BamHI fragment from pNH202 containing the SPO1-15 promoter was ligated with linkers P2-CII and P2-DII and pCI20R-digested with BamHI and ClaI. The ligated DNA was then transformed into *E. coli* DH5α cells. White colonies resulted and miniprep analyses indicated that pRF63 had the desired structure. The 470 bp ClaI-BamHI fragment was isolated then from pRF63 and ligated to the 2 kb EcoRI-ClaI fragment from pRF49 containing the SPOI-15 promoter and the 5'-end of the rib operon and pRF64 (FIG. 15), containing the SPO1 promoter and the 3'-end of the operon, digested with EcoRI and BamHI. The ligated DNA was then transformed into *E. coli* DH5α cells. Miniprep DNA was prepared; pRF66 had the desired structure. In addition, *E. coli* containing pRF66 produced small amounts of riboflavin on LB medium+ampicillin plates, confirming that the operon was still intact.

The last step was to ligate the cat gene into the unique XbaI sites of pRF66 as described above. The resulting plasmid, pRF69 (FIG. 15) contained the cat gene in the same direction as the rib operon.

To construct a plasmid containing the entire operon with the natural or wild-type ribP$_1$ promoter and the SPO1-15 promoter after ribP$_2$, the 6.3 kb EcoRI-BamHI fragment of pRF64, the 2.75 kb EcoRI-ClaI fragment of pRF36, and the 470 bp ClaI-BamHI fragment of pRF63 were ligated and tranformed into *E. coli* DH5α cells. About 50% of the Ap$^r$ colonies were yellow, indicating ribflavin production. Mini-prep DNA was prepared from yellow colonies and pRF68 had the desired structure (FIG. 16). A cat gene was added to pRF68 at the XbaI site, as discussed above, to generate pRF71 (FIG. 16). This plasmid contained the cat gene in the same direction as the rib operon.

As another example of the construction of useful plasmids in this invention, there now follows an example in which one or more promoters can be introduced within the riboflavin operon without prior removal of existing DNA sequences.

As an example, a prototype modified operon was constructed in pRF78, which contains a single copy of the SPO1-15 promoter inserted within a 30 bp non-essential region located between ribP$_1$ and a putative rho-independent transcriptional termination site (FIG. 14) an inactivated ribP$_1$ promoter to prevent possible transcriptional interference of the SPO1-15 promoter, an active ribP$_2$ promoter, the five structural genes encoding rib biosynthetic enzymes, and approximately 1.5 kb of flanking DNA nucleotide sequences downstream from the end of the riboflavin operon.

Referring to FIG. 14, the 1.7 kb NcoI-PstI fragment of pRF2, a fragment that contains the 5' promoter region of the rib operon and flanking regions, was first subcloned into mp19, a derivative of the *E. coli* bacteriophage vector M13 (United States Biochemical Catalog, 60–61, 1987; available from New England Biolabs, Massachusetts). One recombinant phage, M1.7, was recovered and standard DNA sequence analysis of the promoter region revealed a spontaneous mutation of the −10 region of the ribP$_1$ promoter, a TA-to-CT change, which may inactivate the promoter. Single stranded DNA was prepared and annealed to a synthetically-generated 55 bp DNA oligomer. (see FIG. 17), containing a combination of restriction enzymes sites, 5'-EcoRI-SmaI-BamHI-3', flanked on either side by additional sequences homologous to the DNA region upstream from ribP$_1$. Double-stranded DNA molecules were synthesized using standard site-directed mutagenesis (SDM) protocols. These DNA molecules were introduced into the *E. coli* host TG-1 (available from Amersham Corp. Illinois) by transfection to generate recombinant phage plaques. One recombinant phage was found to contain the desired modified DNA sequence; as determined by standard DNA-sequence analysis.

The modified rib promoter region was then rejoined to the rib structural genes of the operon using a pair of unique NsiI restriction enzymes sites 750 bp apart that flank the ribP$_1$ region and surrounding sequences. Double-stranded DNA molecules of the phage recombinant were prepared, digested with NsiI, the 750 bp fragment isolated, and the fragment ligated to dephosphorylated, 8.7 kb NsiI fragment of pRF39ΔR1 (a plasmid derived from pRF39, FIG. 12, that contains the wild-type rib operon). The ligated DNA molecules were introduced into *E. coli* DH5α cells by transformation, selecting for ampicillin-resistance, which resulted in the recovery of an Ap$^r$ colony harboring the desired recombinant plasmid, pRF75.

The SP01-15 promoter was next inserted upstream from ribP$_1$ by digesting pRF75 with a combination of EcoRI and BamHI enzymes, ligating the cut DNA to purified 400 bp EcoRI-BamHI SPO1-15-containing restriction fragment, and introducing the ligated DNA into *E. coli* DH5α cells by transformation, selecting for ampicillin-resistance. One Ap$^r$ colony was found to harbor the recombinant plasmid, pRF77, containing the desired SPO1-15-modified rib operon. A chloramphenicol-resistance gene, cat, on a 1.6 kb XbaI restriction fragment, was subsequently introduced into pRF77 at the unique XbaI site, generating plasmid pRF78 (FIG. 14).

This prototype operon was further modified to contain an active ribP$_1$ promoter, and/or a second copy of the SPO1-15 promoter introduced downstream from ribP$_2$ within a intercistronic region between the rib coding regions ORF3 and ORF4, as described above. For example, plasmid pRF88, containing a derivative of the modified rib operon in pRF78 with an active ribP$_1$ promoter (FIG. 14) was constructed by the same procedure described above, using a recombinant phage containing the wild-type ribP$_1$ promoter. In other examples, a second copy of the SPO1-15 promoter, located downstream from ribP$_2$ was inserted into the existing modified rib operon-containing plasmids pRF78 and pRF88 by removing the 2.0 kb BglII fragment of either plasmid DNA and inserting the 2.4 kb BglII fragment of pRF66, generating plasmids pRF81 and pRF89 respectively (FIG. 14).

Construction of Ade$^\pm$-RB50 Strains

It is important to use strains of bacteria that require as few components to be added to a fermentation medium as possible. Such strains are cheaper to ferment in order to produce riboflavin. To this end, adenine revertants which contained amplified modified rib operons were constructed. These revertants may not be true revertants of pur-60, but rather include mutations at another site which suppresses the requirement for adenine. As discussed below they produce about 25% more riboflavin than the non-reverted strains. Examples of such constructions are now described.

Plasmids PRF8, pRF40, pRF50, pRF69, pRF71, pRF78, pRF81, pRF88 and pRF89 were each transformed into RB50 (a RoF$^r$, deregulated *B. subtilis* strain) selecting for chloramphonicol resistance (Cm$^r$). A resistant colony was chosen for each strain. Ade$^+$ revertants of each strain was isolated by growing bacteria in RMM1 broth containing 10 μg/ml adenosine, and plating samples of the cultures onto minimal agar plates. One colony from each Ade$^+$ strain was selected and the vector DNA was amplified by selecting colonies that grow on increasingly higher levels of chloramphenicol, to a maximum level of 60 μg/ml.

Second Site Integration

As described above, it is important to amplify an engineered rib operon in the *B. subtilis* chromosome to achieve high titers of riboflavin. It is also important to ensure that the number of DNA copies of the rib operon. within a chromosome are not limiting to riboflavin production. Further amplification of the rib operon can be achieved by integrating and amplifying copies of the rib operon at more than one site in the *B. subtilis* chromosome to further increase riboflavin yield one example of how such second site integration can be achieved is described below.

The above described vectors have all relied upon the cat gene to select for integration at the site of the rib operon. In order to insert the rib genes at a second site, it is preferable to have a different antibiotic resistance gene for use at that second site. For example, a tetracycline-resistance (tet) from *B. subtilis* can be used (Perkins and Youngman, *J. Bacteriol.*, 155:607–615, 1983). Such tet genes are well known to those of ordinary skill in the art and are readily available to such persons. In one such construction, for example, pRF78 (FIG. 14), which contains a modified version of the rib operon, the plasmid can be cut with XbaI and ligated to a 2.4 XbaI fragment containing the tet gene. The resulting plasmid contains the tet gene at the XbaI site and is called pRF85 as shown in FIG. 16.

A strain which is deleted for the entire rib operon and which has a tet gene integrated at a second site is required to cause integration of pRF85 at that site. One such site is the bpr gene encoding bacillopeptidase F, a minor non-essential extracellular protease. An *E. coli* plasmid containing the bpr gene, pKT2, (Sloma et al., *J. Bacteriol.*, 172:1470–1477, 1990) was digested with EcoRV. This EcoRV site is in the coding region of bpr. The DNA was then ligated to a 2.4 kb EcoRI fragment containing the tet gene that had been blunt-ended. The resulting plasmid (containing the tet gene at the EcoRV site of bpr) was called PKT2-tet. This DNA was linearized with EcoRI and then transformed into RB52, a strain deregulated for riboflavin synthesis. Tet$^r$ colonies resulted and one such colony was called RB54. The integrated tet gene at bpr will function as a homologous sequence for the integration of pRF85.

To ensure that the cloned riboflavin operon of pRF85 would be inserted at the second chromosomal site containing the tetracycline-resistance gene, a region containing the original riboflavin operon and flanking DNA, equalling that contained in pRF85, was deleted from the chromosome of RB54 by in vitro methods. Briefly, this involves first generating an *E. coli* recombinant plasmid where the cloned riboflavin operon and flanking regions between the NcoI and XbaI restriction sites are removed and replaced by a chloramphenicol-resistance gene, cat, that is expressed in *B. subtilis* bacteria. This plasmid is then used to delete the chromosomal riboflavin operon by transforming RF54 with linearized plasmid molecules and selecting for chloramphenicol resistant (Cm$^r$) bacteria. Cm$^r$ bacteria result from a recombinant event (marker-replacment) which replaces the wild-type rib genes with the deleted copy containing the cat gene.

Specifically, plasmid pRF34 (see example 6) was used to generate an *E. coli* plasmid containing an in vitro-generated riboflavin operon deletion. This plasmid is derived from pRF2 where the riboflavin operon is flanked on either end by two unique XbaI sites (one site located upstream from the 5'-end of the rib operon next to the deleted 0.8 kb NcoI fragment and the second site located approximately 1.6 kb downstream from the end of the operon) and a cat gene is inserted outside of this region. By digesting pRF34 with XbaI and ligating the cut DNA molecules under dilute DNA concentrations, a recombinant plasmid, pRF82, was recovered where a 7.2. kb region containing the riboflavin operon is removed and essentially replaced with the cat gene. Plasmid pRF82 was linearized by restriction enzyme digestion and the cut DNA used to remove the chromosomal riboflavin operon of RB54 by DNA transformation, selecting for Cm$^r$ bacteria, resulting in marker replacement. Cm$^r$ colonies were screened for riboflavin auxotrophy and one Rib$^-$Cm$^r$ colony, RB55, was recovered for further investigation.

Plasmid pRF85 was transformed into strain RB55, selecting for Rib$^+$. One Rib$^+$ transformant was chosen and called RB58. This strain has the rib operon integrated at bpr by homologous recombination between the tet$^r$ genes in the plasmid and the chromosome. A transducing lysate of RB58 was prepared using standard techniques, and it was used to transduce RB50::[pRF69], selecting for Tet$^r$. These resistant colonies were found to have the modified rib operon integrated at the site of the rib operon and at bar. One such Tc$^r$ colony RB50::[pRF69]$_{60}$::[pRF85]$_{120}$Ade$^+$ was recovered for further study. The rib operon integrated at rib was amplified by selecting for colonies that grow in the presence of increasing levels of chloramphenicol as described above, and the second copy of the rib operon was amplified by selecting colonies that grow on increasing levels of tetracycline to 120 μg/ml.

EXAMPLE 9

Fermentative Production of Riboflavin

Evaluation of riboflavin-overproducing strains was conducted in Chemap 14-liter vessels in carbon-limited fed-batch fermentations, with riboflavin content measured by HPLC. Since enzymes encoded by the genes for riboflavin synthesis are rate-limiting, the rib genes, which were amplified, were maintained at high-copy number by the inclusion of 60 µg/ml chloramphenicol in the inoculum seed train, but not in the fermentor.

A culture of a riboflavin-overproducing strain such as *B. subtilis* RB50::[pRF69]$_{60}$Ade$^+$ was grown on Tryptose Blood Agar Base (TBAB Difco) containing 60 ug/ml of chloramphenicol (CAM). Colonies were transferred to 300 ml baffled flasks containing 25 ml of riboflavin minimal medium (RMM; containing sodium glutamate 2.0 g/l, Casamino acids (Difco) 0.2 g/l, Yeast extract (Difco) 0.2 g/l KH$_2$PO$_4$ 6.0 g/l, K$_2$HPO$_4$ 14.0 g/l, (NH$_4$)$_2$SO$_4$ 2.0 g/l, sodium citrate 1.0 g/l, MgSO$_4$.7H$_2$O 0.2 g/l, glucose 15.0 g/l, pH 7.0) with 60 ug/ml CAM. The inoculated flasks were incubated by shaking at 250 rpm and 37° C. After 8 hours, sterile glycerol was added to a final concentration of 15% and 1 ml aliquots were stored at −80° C.

In order to initiate a fermentation a frozen vial of the appropriate strain, e.g., RB50::[pRF69]$_{60}$Ade$^+$ was thawed at 37° C. and transferred into a 300 ml baffled flask with 25 ml of RMM with 60 ug/ml CAM and shaken at 250 rpm and 37° C. After 8 hours, 6 ml of the growing culture was used to inoculate 300 ml of fermentation medium (see Table VII below) in a series of 2 liter transfer flasks. Each flask contained 300 ml of fermentation medium to which had been added 90 ml of 15% glucose. Chlorphemicol was added to a final concentration of 60 ug/ml. After incubation for 12 hours at 200 rpm on an shaker with a 2" diameter orbit at 37° C., the contents of each flask was transferred to 7 liters of fermentation medium in a 14 liter fermentation vessel.

During fermentation, the broth was continually monitored for pH and dissolved oxygen (DO$_2$). Off gas was continuously analyzed by quadrapole mass spectrometry and carbon dioxide evolution (CER) and oxygen uptake rates were recorded.

A comparison of several fermentations demonstrated the reproducibility of the control systems. The initial carbohydrate was exhausted from fermentation with RB50::[pRF8]$_{60}$ after 4 hours of growth, causing a rise in pH and a fall in CER. At that point, carbohydrate feeding was initiated and logarithmic growth resumed until DO$_2$ became limiting at 6 hours. The rate of carbohydrate feeding was computer-controlled to maintain the DO$_2$ between 10–20% of saturation throughout the remaining fermentation time.

Excess carbohydrate in the fermentors does lead to oxygen starvation and reduced riboflavin production. oxygen transfer limitations determine the duration of logarithmic growth, final cell density and the riboflavin production rate. To increase the oxygen transfer rate, Chemap fermentors were run at 1000 rpm with a head pressure of 0.6 atmospheres.

Supplementation of the medium carbohydrate feed with yeast extract led to an increase in riboflavin production as compared to media without supplementation (FIG. 11, open squares: RBF-14; Table VII). However, because of its high cost, the amount of yeast extract was systematically reduced by substituting less expensive, inorganic ingredients. Substitution of ammonium hydroxide for sodium hydroxide in pH control allowed a reduction of yeast extract in the feed and resulted in an increase in both cell mass and riboflavin titer (FIG. 11, closed squares: RBF-22; Table VII). Fermentation times were also reduced. In other fermentations, moreover, yeast extract was completely eliminated from the feed and replaced with a combination of inorganic salts of ammonium and phosphate, resulting in a further increase in riboflavin production and a reduction of process time (FIG. 11, open circles: RBF-23; Table VII).

The original RB50::[pRF8]$_{60}$ was auxotrophic for adenine because of its pur-60 mutation. When experiments were conducted to determine the minimum amount of adenosine required by the strain, in order to minimize its inhibition of earlier biosynthetic enzymes involved in the pathway leading to the riboflavin-precursor IMP (FIG. 2). RB50::[pRF8]$_{60}$ (and, in general, RB50 strains with a rib operon amplified within their chromosome) was found to be unstable in its adenosine requirement and prototrophic revertants (Ade$^+$) were produced at a fairly high frequency. In shake flasks, the Ade$^+$ revertants appeared to grow and produce riboflavin at least as well as the RB50::[pRF8]$_{60}$ parent. When evaluated in fermentors, the revertant, RB50::[pRF8]$_{60}$(Ade$^+$), did not require adenosine in the media formulation. More importantly, the revertant grew at a faster rate and produced 25% more riboflavin than its parent strain in less time. A titer of 5.4 g/l riboflavin was produced in 49 hours (FIG. 11, closed circles: RBF-29; Table VII). In additional fermentations, moreover, Hy Soy T was removed from the initial charge or medium and replaced with corn steep liquor, resulting in a further increase in riboflavin production to 6.3 g/l in 48 hours. (RBF-42, Table VII).

Under these fermentation conditions, further significant increases in riboflavin production were demonstrated using bacterial strains that contained engineered riboflavin operon DNA. Strains containing the wild-type riboflavin operon on a 6.5 kb EcoRI-XbaI restriction fragment, RB50::[pRF40]$_{60}$ (Ade$^+$), produced 7.4 g/l of riboflavin in 48 hours. Moreover, strains containing a transcriptionally-modified rib operon where the ribP$_1$ promoter and regulatory region were replaced by the constitutive SPO1-15 promoter, RB50::[pRF50]$_{60}$(Ade$^+$), produced 9.0 g/l of riboflavin in 48 hours. These results demonstrate that modification of the riboflavin operon through the removal of regulatory regions and/or through the introduction of stronger, constitutive exogenous promoters leads to increases in riboflavin titer.

TABLE VII

| FERMENTATION COMPONENTS AND CONDITIONS | | | | | |
| --- | --- | --- | --- | --- | --- |
| Component | RBF-14 | RBF-22 | RBF-23 | RBF-29 | RBF-42 |
| Initial Charge (g/l) | | | | | |
| Glucose | 10.00 | 15.00 | 15.00 | 15.00 | 15.00 |
| Corn step liquor | — | — | — | — | 10.00 |
| Hy Soy T | 15.00 | 15.00 | 15.00 | 10.00 | — |
| Sodium glutamate | — | — | — | 5.00 | 5.00 |
| Amberex 500 | 15.00 | 15.00 | 20.00 | 20.00 | 20.00 |
| KH$_2$PO$_4$ | 5.00 | 5.00 | 7.50 | 7.50 | 7.50 |
| M$_g$Cl$_2$.6H$_2$O | 0.5 | 0.5 | 1.50 | 1.50 | 1.50 |
| MnSO$_4$ | 0.05 | 0.05 | 0.05 | 0.05 | 0.05 |
| Adenosine | 0.05 | 0.05 | 0.05 | — | — |
| MAZU DF37 | 2.50 | 2.50 | 2.50 | 2.50 | 2.50 |
| FeCl$_3$ | — | — | 0.025 | 0.02 | 0.02 |
| CaCl$_2$ | — | — | 0.50 | 0.50 | 0.50 |
| ZnSO$_4$ | — | — | 0.0005 | — | — |

TABLE VII-continued

FERMENTATION COMPONENTS AND CONDITIONS

| Component | RBF-14 | RBF-22 | RBF-23 | RBF-29 | RBF-42 |
|---|---|---|---|---|---|
| CuCl$_2$ | — | — | 0.001 | — | — |
| CoCl$_2$ | — | — | 0.0013 | — | — |
| Nutrient Feed (g/l) | | | | | |
| Amberex 500 | 160.00 | 120.00 | — | — | — |
| NH$_4$Cl | — | — | 7.50 | 7.50 | 7.50 |
| (NH$_4$)$_2$SO$_4$ | — | — | 7.50 | 7.50 | 7.50 |
| KH$_2$PO$_4$ | — | — | 15.00 | 15.00 | 15.50 |
| MgSO$_4$.7H$_2$O | — | — | 2.50 | 2.50 | 2.50 |
| DL-70 syrup (as DS) | 600.00 | 600.00 | 600.00 | 660.00 | 600.00 |
| pH Control Range | | | | | |
| 6.6 | H$_2$SO$_4$ | H$_2$SO$_4$ | H$_2$SO$_4$ | H$_2$SO$_4$ | H$_2$SO$_4$ |
| 6.5 | NaOH | NH$_4$OH | NH$_4$OH | NH$_4$OH | NH$_3$ |
| Conditions | | | | | |
| Air (vvm) | 1.0 | 1.5 | 1.5–2.0 | 1.5 | 1.50 |
| RPM | 1000.0 | 1000.0 | 1000.0 | 1000.0 | 1000.0 |
| Temp ° C. | 37.0 | 37.0 | 37.0 | 37.0 | 37.0 |
| Pressure (bar) | 0.5 | 0.5 | 0.5–0.75 | 0.6 | 0.6 |
| Riboflavin (g/l) | 3.4 (64 hrs) | 4.1 (56 hrs) | 4.3 (53 hrs) | 5.4 (49 hrs) | 6.3 (48 hrs) |
| Dry Weight (g/l) | 33.6 | 36.0 | 36.8 | ND | 44.6 |

The kinetics of riboflavin production in the various fermentations were analyzed using the Luedeking-Piret model. In all cases, the specific productivity declined from the conclusion of the exponential growth phase to the end of fermentation. Also, it was clear that riboflavin production was growth-associated under the fermentation conditions used.

We have discovered that the yield of riboflavin can be increased by changing the fermentation components and conditions. The yield of riboflavin can be increased compared to those conditions described above using those fermentation components and conditions shown in Table VIII.

TABLE VIII

| | RBF 150 (g/liter) | RBF 184 (g/liter) |
|---|---|---|
| Initial Batch | | |
| Yeast Extract | 20 | 20 |
| Glucose | 25 | 25 |
| KH$_2$PO$_4$ | 7.5 | 7.5 |
| MgCl$_2$.H$_2$O | 1.5 | 1.5 |
| CaCl$_2$.2H$_2$O | 1.0 | 1.0 |
| MnSO$_4$ | 0.05 | 0.05 |
| FeCl$_3$.6H$_2$O | 0.025 | 0.025 |
| Mazu DF37C | 2.5 | 2.5 |
| Corn Steep Liquor | 10 | — |
| Sodium Glutamate | 5 | 5 |
| (NH$_4$)$_2$ SO$_4$ | — | 0.3 |
| Feed Medium (3 liters total used) | | |
| Glucose | 583.3 | — |
| NaCitrate | 6.67 | 6.67 |
| KH$_2$PO$_4$ | 15 | 15 |
| Succinic Acid | 1.67 | 1.67 |
| MgSO$_4$.7H$_2$O | 1.67 | 1.67 |
| Corn Syrup Solids | — | 833 |

Briefly, in one such fermentation the starting material is 6.65 liters of batch medium and 0.35 liters of bacterial (RB50::[pRF50]$_{60}$Ade$^+$) inoculant. Oxygen levels are monitored with a Chemap polarographic dissolved oxygen electrode. Dissolved oxygen levels are E maintained at 15%±5% by means of computer regulated addition of the feed medium. Total feed added is about 3.0 liters in 48–56 hours. Fermentation pH is maintained at 6.5±0.1 (using 1N H$_2$SO$_4$ and NH3 gas), and fermenter pressure is maintained at 0.6 bars, temperature at 37° C., and air flow at 10.5 liters/min. Under these conditions, strain RB50::[pRF50]$_{60}$(Ade$^+$) produced 11.0 g/l riboflavin in 48 hours, which represents an improvement in production of approximately 20% compared to the previous fermentation conditions. An increase in riboflavin production was demonstrated (RBF150, Table VIII) using the bacterial strains RB50::[pRF69]$_{60}$(Ade$^+$) containing a transcriptionally-modified riboflavin operon containing two SPO1-15 promoters, one replacing ribP$_1$ and regulatory sequences, and a second inserted between ORF3 and ORF4. This strain produced 13.0–14.0 g/l riboflavin in 48 hours, and 15 g/l in 56 hours, demonstrating that increased transcription of the riboflavin operon using two strong exogenous promoters increases production levels of riboflavin. Finally, a further increase in riboflavin production was demonstrated using the bacterial strain RB50:: [pRF69]$_{60}$::[pRF85]$_{120}$Ade$^+$ containing two amplifiable rib loci as in Example 8. This strain was grown at pH 6.8 and 39° C. using the modified fermentation medium shown in Table VIII (RBF 184) and riboflavin was isolated.

Deposits of Microorganisms

Plasmid pRF69, and strains containing plasmids pRF50 and pRF78, as well as strain RB58 have been deposited with the American Type Culture Collection on the following dates, and have been assigned the following accession numbers.

| Material | Deposit Date | Accession Number |
|---|---|---|
| pRF69 | Jun. 6, 1990 | 68338 |
| RB58 | May 30, 1990 | 55053 |
| pRF50 | May 30, 1990 | 68332 |
| pRF78 | May 30, 1990 | 68333 |

*Bacillus subtilis* strain RB50 was deposited with the Agricultural Research Culture Collection (NRRL), Peoria, Ill., under the Budapest Treaty on the International Recognition of the Deposit of Microorganisms for the Purposes of Patent Procedures, and was assigned accession number B 18502. Applicants' assignee, Hoffmann-LaRoche, acknowledges its responsibility to replace these cultures should they die before the end of the term of a patent issued hereon, 5 years after the last request for a culture, or 30 years, whichever is the longer, and its responsibility to notify the depository of the issuance of such a patent, at which time the deposits will be made available to the public. Until that time the deposits will be made irrevocably available to the Commissioner of Patents under the terms of 37 C.F.R. §1–14 and 35 U.S.C. §112.

The present invention is not to be limited in scope by the microorganism deposited since the deposited embodiment is intended as a single illustration of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entirety.

Other embodiments are within the following claims.

SEQUENCE LISTING

```
<160> NUMBER OF SEQ ID NOS: 17

<210> SEQ ID NO 1
<211> LENGTH: 5567
<212> TYPE: DNA
<213> ORGANISM: Bacillus subtilis
<220> FEATURE:
<221> NAME/KEY: promoter
<222> LOCATION: (770)..(799)
<220> FEATURE:
<221> NAME/KEY: promoter
<222> LOCATION: (2528)..(2556)
<220> FEATURE:
<221> NAME/KEY: promoter
<222> LOCATION: (4545)..(4574)

<400> SEQUENCE: 1
ctgcaggtcg actctagagg atcccccatg gacagccgta acggccttgg cctcttcacg      60
aaaaaacaaa ttgcgggtac gtcaaagttt gttttctacc cgtttaacga aatgcgcaaa     120
acaaattagg atcaagcagc ttcccattgg ggctgctttt tttatatctt ttttacggtc     180
atcccctaaa aacagaacat aaattcgtat atctatagaa aagaaatttt tgcagaaatg     240
tgaaacatat tcccgttatg catcgttata ttaataattt acgagaattt acggtttttt     300
attcatgaaa aaaggaata actcatatga atgaatagat tcatattggc tggaggttta     360
gaaatgggaa gaataaaaac caagattacc attctgttag tgcttttgct tttacttgca     420
ggcggttata tgtacataaa tgatattgag ctgaaggatg ttccgacagc aattggacaa     480
accttgtcct cggaagaaga ggaatacacc atccaggaat ataaagtgac gaaaattgac     540
ggctcagagt atcatggagt agcagaaaac ggaacgaaaa tcatcttcaa cggaaaaaaa     600
ttaaatcagg atttatctga tataaaagaa ggtgacaaga ttaaggctta cttcagcaaa     660
tcaaagcgga tcgacggtta atcaaggttg caaaagtgaa tgattaaaaa acatccacctt     720 tcggatcgaa gggtgatgtt ttgtttttct caaattgtaa gtttatttca ttgcgtactt     780 taaaaggat cgctataata accataagg acaaatgaat aaagattgta tccttcgggg     840
cagggtggaa atcccgaccg gcggtagtaa agcacatttg ctttagagcc cgtgacccgt     900
gtgcataagc acgcggtgga ttcagtttaa gctgaagccg acagtgaaag tctggatggg     960
agaaggatga tgagccgcta tgcaaaatgt ttaaaaatgc atagtgttat ttcctattgc    1020
gtaaaatacc taaagccccg aattttttat aaattcgggg ctttttttgac ggtaaataac    1080 aaaagagggg agggaaacaa atggaagagt attatatgaa gctggcctta gatcttgcga    1140
agcagggcga aggacagacc gaatccaatc cgctcgtcgg cgctgttgtc gtaaaggacg    1200
gacaaattgt cggaatgggc gcccatttaa aatatggtga agctcatgca gaagttcatg    1260
ccatccatat ggctggagca catgcagagg gtgccgacat ttacgttaca ctcgaaccgt    1320
gcagccatta cggaaaaaca ccgccatgtg cagaattgat tatcaactct ggtatcaaaa    1380
gagtgttcgt ggcgatgaga gatcctaatc cgcttgtggc tggaagaggg atcagcatga    1440
```

```
tgaaagaagc tggcattgag gtaagggaag gcatcctggc agaccaggcg gagaggctga   1500
atgaaaaatt tctgcacttt atgaggacag gccttccgta cgtcacgcta aaagcggctg   1560
ccagccttga cggcaagata gctaccagca cgggtgacag caaatggatc acgtcagagg   1620
ctgcaagaca ggatgctcag caatacagga aaacacacca aagcattttta gtcggagttg   1680 gcacagtgaa agccgacaat ccgagcttaa cctgcagact gccgaatgta acaaaacagc   1740
cggttcgggt catacttgat accgtactct cgattcctga ggacgctaaa gtgatttgcg   1800
atcaaatagc gccgacatgg attttttacga cggcacgcgc agacgaggaa aagaaaaaac   1860
ggctttcagc tttcggagtg aacatatttta cacttgaaac cgagcgcatt caaattcctg   1920
atgttttgaa gatcctagcg gaagaaggca tcatgtcggt gtatgtggaa ggcggttcag   1980
ctgttcacgg aagctttgtc aaagaaggct gttttcaaga atcatcttc tatttttgccc   2040 ctaaactaat cggaggaacg catgctccca gcttaatctc cggtgaaggt tttcaatcaa   2100
tgaaagatgt ccccttatta caattcactg atataaccca aatcggccgt gatatcaaac   2160
tgacggcaaa accgacaaag gaataggatg gtgaccatgt ttacaggaat tatcgaagaa   2220
acaggcacaa tcgaatccat gaaaaaagca gggcatgcaa tggccttaac tattaaatgc   2280
tcaaagattt tagaggatgt tcatcttggc gacagcattg cagtgaacgg catttgtctg   2340
actgtcactg attttacaaa aaatcaattc acagtggatg ttatgcctga aacagtcaaa   2400
gctacgtcac tgaatgattt aacaaaagga agcaaagtaa atctggaaag agcgatggcg   2460
gcaaacggcc gttcggagg ccatttcgtc tcaggccatg tcgacggaac tgcggaaatc   2520
acacgaattg aagagaaaag caacgcagtt tactatgatt taaaaatgga cccgtcatta   2580
acaaaaacat tggttttaaa gggatcaatt actgtggatg gcgtgagctt aaccatattc   2640
ggcctgacag aagacacagt gacgatctcc ttaataccgc atacgatcag cgaaacgatc   2700
ttttcagaaa aaacgatcgg ctctaaagtg aatatcgaat gcgatatgat cggaaaatat   2760
atgtatcgat ttttgcataa agccaatgaa aataagaccc aacaaaccat tacaaaagcc   2820
ttcttaagcg aaaacggctt ttagagagga agatttgcat gtttcatccg atagaagaag   2880
cactggacgc tttaaaaaaa ggcgaagtca tcatcgttgt agatgatgaa acagagaaaa   2940
atgaaggaga ctttgtggct cttgccgagc atgcaacgcc ggaagtcatt aactttatgg   3000
cgacacatgg gagaggactg atctgcacgc cgctcagtga ggaaatcgca gacaggcttg   3060
atcttcaccc tatggttgag cataatacag actctcacca cactgcattt accgtaagca   3120
tagaccatcg tgaaacgaag acaggtatca gcgctcaaga aagatctttt accgttcaag   3180
cattgctgga cagcaaatcc gtgccatctg attttcagcg tccggggcac attttttccac   3240 tgattgcgaa aaaggaggt gtcctgaaaa gcgcgggcca tacagaagct gctgttgatc   3300
ttgctgaagc ttgcggatct ccaggagccg gcgtcatttg tgaaattatg aatgaagacg   3360
gaacgatggc gagagtgcct gagctcattg aaattgcgaa aaagcatcaa ttaaaaatga   3420
tcaccattaa ggatttgatt caataccgtt acaatctgac aacacttgtc gagcgtgaag   3480
ttgacattac gctgcctact gattttggga catttaaggt ttatggatac acaaatgagg   3540
tagatggaaa agagcatgtc gcatttgtga tgggagatgt gccgttcgga aagaaccgg   3600 tattggtccg ggtgcattca gaatgtctca caggtgacgt gtttggctct catcgctgtg   3660
attgcggacc gcagctgcac gccgcgctga accaaattgc cgcagaaggc cgtggagtgc   3720
tcctgtactt gcgccaagaa ggacgaggca tcggtttaat caataaatta aaagcttata   3780
agcttcagga acaaggctat gacaccgtag aagccaatga ggcgcttgga ttcttgccgg   3840
```

-continued

| | |
|---|---|
| atcttcgcaa ctatggcatc ggagcacaaa ttttacgcga cctcggtgtc cggaatatga | 3900 |
| agcttttgac gaataatccg cgaaaaatcg caggccttga aggctacgga ctcagtattt | 3960 |
| cagaaagagt gccgcttcaa atggaggcga agaacacaa taaaaaatat ttgcaaacca | 4020 |
| aaatgaacaa gctaggtcat ttacttcatt tctaatcaca aatatcacaa aaaaggatgg | 4080 |
| gaatcatatg aatatcatac aaggaaattt agttggtaca ggtcttaaaa tcggaatcgt | 4140 |
| agtaggaaga tttaatgatt ttattacgag caagctgctg agcggagcag aagatgcgct | 4200 |
| gctcagacat ggcgtagaca caaatgacat tgatgtggct tgggttccag gcgcatttga | 4260 |
| aataccgttt gctgcgaaaa aaatggcgga acaaaaaaa tatgatgcta ttatcacatt | 4320 |
| gggcactgtc atcagaggcg caacgacaca ttacgattat gtctgcaatg aagctgcaaa | 4380 |
| aggcatcgcg caagcagcaa acactactgg tgtacctgtc atctttggaa ttgtaacaac | 4440 |
| tgaaaacatc gaacaggcta tcgagcgtgc cggcacaaaa gcgggcaaca aggtgtaga | 4500 |
| ttgtgctgtt tctgccattg aaatggcaaa tttaaaccgc tcatttgaat aatttgctga | 4560 |
| aaacagttta aaaatatggc gaaaatgata taatgtgaga aaacggatca cctattcgta | 4620 |
| tccgttaata gcagactgga cattttggat atagaggggt ttttatgtta attcgttata | 4680 |
| aaaaatcgtt tgaaaagatt gcgatggggc ttctttcgtt tatgccgaat gaaaaagacc | 4740 |
| ttaagcagct tcagcagaca attaaggact acgaaacgga tacagaccgc cagctctttc | 4800 |
| tttggaaaga ggacgaggat atcgtcggag caatcggagt cgaaaaaag gattctgagg | 4860 |
| ttgagatccg gcatatcagt gtgaatcctt ctcatcgcca tcaaggaatc ggaaaacaga | 4920 |
| tgatggatgc tttaaagcat ttattcaaaa cgcaagtact ggttccaaat gaattaacgc | 4980 |
| agagcttttt cgaacgttgt caaggtcagc aggatcaaga catttcatac aataattaag | 5040 |
| cagaggctgt gatcagtctc tgcttttttt tctgcgttct atttcttttt cacgttcacg | 5100 |
| gatgacgtca gtccgatccc gcaaacggtg tttgtcgata agaaatatgt tgctgagtgc | 5160 |
| actgggctgc cccatgtat acttttttt cctgcattcg atcctgcatg cttcctccag | 5220 |
| tttctcatct ttgattggca gtataatgct tttataggca gagacggttt cgatttgttc | 5280 |
| gtaaaccgat tgcataagtt cgagcaaacg gccatgatca agccctaagt cttcgactgc | 5340 |
| ccggtgttct gcttgaagaa tccggatgct gttcgccatc agtctttttg ccccggctgt | 5400 |
| attctgcctt ctgtgatgat ataaagccac tgcaagctga ataaagccca cccaatagcg | 5460 |
| ttttcgtttc tttggcggat cttccttcca atattcttct aatatttcat ggcattcaaa | 5520 |
| ataatcccgt gtcgcatgaa actcaacgag ataatctata taagctt | 5567 |

<210> SEQ ID NO 2
<211> LENGTH: 5567
<212> TYPE: DNA
<213> ORGANISM: Bacillus subtilis

<400> SEQUENCE: 2

| | |
|---|---|
| gacgtccagc tgagatctcc taggggggtac ctgtcggcat tgccggaacc ggagaagtgc | 60 |
| ttttttgttt aacgcccatg cagtttcaaa caaaagatgg gcaaattgct ttacgcgttt | 120 |
| tgtttaatcc tagttcgtcg aagggtaacc ccgacgaaaa aatatagaa aaaatgccag | 180 |
| taggggattt ttgtcttgta tttaagcata tagatatctt ttctttaaaa acgtctttac | 240 |
| actttgtata aggcaatac gtagcaatat aattattaaa tgctcttaaa tgccaaaaaa | 300 |
| taagtacttt ttttccttat tgagtatact tacttatcta agtataaccg acctccaaat | 360 |

-continued

```
ctttacccctt cttattttg gttctaatgg taagacaatc acgaaaacga aaatgaacgt      420
ccgccaatat acatgtattt actataactc gacttcctac aaggctgtcg ttaacctgtt      480
tggaacagga gccttcttct ccttatgtgg taggtcctta tatttcactg cttttaactg      540
ccgagtctca tagtacctca tcgtcttttg ccttgctttt agtagaagtt gcctttttt       600 aatttagtcc taaatagact atattttctt ccactgttct aattccgaat gaagtcgttt      660
agtttcgcct agctgccaat tagttccaac gtttttcactt actaatttt tgtagtggaa      720 agcctagctt cccactacaa aacaaaaaga gtttaacatt caaataaagt aacgcatgaa      780 attttttccta gcgatattat tggttattcc tgtttactta tttctaacat aggaagcccc     840
gtcccacctt tagggctggc cgccatcatt tcgtgtaaac gaaatctcgg gcactgggca     900
cacgtattcg tgcgccacct aagtcaaatt cgacttcggc tgtcactttc agacctaccc     960
tcttcctact actcggcgat acgttttaca aattttacg tatcacaata aaggataacg     1020
cattttatgg atttcgggc ttaaaaata tttaagcccc gaaaaactg ccatttattg      1080 ttttctcccc tcccttttgtt taccttctca taatatactt cgaccggaat ctagaacgct     1140
tcgtcccgct tcctgtctgg cttaggttag gcgagcagcc gcgacaacag catttcctgc     1200
ctgtttaaca gccttacccg cgggtaaatt ttataccact tcgagtacgt cttcaagtac     1260
ggtaggtata ccgacctcgt gtacgtctcc cacggctgta aatgcaatgt gagcttggca     1320
cgtcggtaat gccttttgt ggcggtacac gtcttaacta atagttgaga ccatagtttt     1380
ctcacaagca ccgctactct ctaggattag gcgaacaccg accttctccc tagtcgtact     1440
actttcttcg accgtaactc cattcccttc cgtaggaccg tctggtccgc ctctccgact     1500
tactttttaa agacgtgaaa tactcctgtc cggaaggcat gcagtgcgat tttcgccgac     1560
ggtcggaact gccgttctat cgatggtcgt gcccactgtc gtttacctag tgcagtctcc     1620
gacgttctgt cctacgagtc gttatgtcct tttgtgtggt ttcgtaaaat cagcctcaac    1680
cgtgtcactt tcggctgtta ggctcgaatt ggacgtctga cggcttacat tgttttgtcg     1740
gccaagccca gtatgaacta tggcatgaga gctaaggact cctgcgattt cactaaacgc    1800
tagtttatcg cggctgtacc taaaaatgct gccgtgcgcg tctgctcctt tcttttttg     1860 ccgaaagtcg aaagcctcac ttgtataaat gtgaactttg gctcgcgtaa gtttaaggac     1920
tacaaaactt ctaggatcgc cttcttccgt agtacagcca catacacctt ccgccaagtc     1980
gacaagtgcc ttcgaaacag tttcttccga caaaagttct ttagtagaag ataaaacggg    2040
gatttgatta gcctccttgc gtacgagggt cgaattagag gccacttcca aaagttagtt     2100
actttctaca ggggaataat gttaagtgac tatattgggt ttagccggca ctatagtttg     2160
actgccgttt tggctgtttc cttatcctac cactggtaca aatgtcctta atagcttctt     2220
tgtccgtgtt agcttaggta ctttttcgt cccgtacgtt accggaattg ataatttacg     2280
agtttctaaa atctcctaca agtagaaccg ctgtcgtaac gtcacttgcc gtaaacagac    2340
tgacagtgac taaaatgttt tttagttaag tgtcacctac aatacggact ttgtcagttt     2400
cgatgcagtg acttactaaa ttgttttcct tcgtttcatt tagaccttc tcgctaccgc     2460 cgtttgccgg caaagcctcc ggtaaagcag agtccggtac tgctgccttg acgcctttag    2520
tgtgcttaac ttctctttc gttgcgtcaa atgatactaa attttttacct gggcagtaat    2580 tgttttttgta accaaaattt ccctagttaa tgacacctac cgcactcgaa ttggtataag    2640
ccggactgtc ttctgtgtca ctgctagagg aattatggcg tatgctagtc gctttgctag    2700 aaaagtctttt tttgctagcc gagatttcac ttatagctta cgctatacta gccttttata    2760
```

-continued

```
tacatagcta aaaacgtatt tcggttactt ttattctggg ttgtttggta atgttttcgg      2820
aagaattcgc ttttgccgaa aatctctcct tctaaacgta caaagtaggc tatcttcttc      2880
gtgacctgcg aaattttttt ccgcttcagt agtagcaaca tctactactt ctgtctcttt      2940
tacttcctct gaaacaccga gaacggctcg tacgttgcgg ccttcagtaa ttgaaatacc      3000
gctgtgtacc ctctcctgac tagacgtgcg gcgagtcact cctttagcgt ctgtccgaac      3060
tagaagtggg ataccaactc gtattatgtc tgagagaggt gtgacgtaaa tggcattcgt      3120
atctggtagc actttgcttc tgtccatagt cgcgagttct ttctagaaaa tggcaagttc      3180
gtaacgacct gtcgtttagg cacggtagac taaaagtcgc aggccccgtg taaaaaggtg      3240
actaacgctt ttttcctcca caggactttt cgcgcccggt atgtcttcga cgacaactag      3300
aacgacttcg aacgcctaga ggtcctcggc cgcagtaaac actttaatac ttacttctgc      3360
cttgctaccg ctctctcgga ctcgagtaac tttaacgctt tttcgtagtt aatttttact      3420
agtggtaatt cctaaactaa gttatggcaa tgttagactg ttgtgaacag ctcgcacttc      3480
aactgtaatg cgacggatga ctaaaaccct gtaaattcca atacctatg tgttactcc       3540
atctacctt tctcgtacag cgtaaacact accctctaca cggcaagcct cttcttggcc       3600
ataaccaggc ccacgtaagt cttacagagt gtccactgca caaaccgaga gtagcgacac     3660
taacgcctgg cgtcgacgtg cggcgcgact tggtttaacg gcgtcttccg gcacctcacg     3720
aggacatgaa cgcggttctt cctgctccgt agccaaatta gttatttaat tttcgaatat     3780
tcgaagtcct tgttccgata ctgtggcatc ttcggttact ccgcgaacct aagaacggcc     3840
tagaagcgtt gataccgtag cctcgtgttt aaaatgcgct ggagccacag gccttatact     3900
tcgaaaactg cttattaggc gctttttagc gtccggaact tccgatgcct gagtcataaa     3960
gtctttctca cggcgaagtt tacctccgct ttcttgtgtt atttttttata aacgtttggt     4020
tttacttgtt cgatccagta aatgaagtaa agattagtgt ttatagtgtt ttttcctacc     4080
cttagtatac ttatagtatg ttcctttaaa tcaaccatgt ccagaatttt agccttagca     4140
tcatccttct aaattactaa aataatgctc gttcgacgac tcgcctcgtc ttctacgcga     4200
cgagtctgta ccgcatctgt gtttactgta actacaccga acccaaggtc cgcgtaaact     4260
ttatggcaaa cgacgctttt tttaccgcct ttgtttttt atactacgat aatagtgtaa      4320
cccgtgacag tagtctccgc gttgctgtgt aatgctaata cagacgttac ttcgacgttt     4380
tccgtagcgc gttcgtcgtt tgtgatgacc acatggacag tagaaacctt aacattgttg     4440
actttgtag cttgtccgat agctcgcacg gccgtgtttt cgcccgttgt ttccacatct      4500
aacacgacaa agacgtaac tttaccgttt aaatttggcg agtaaactta ttaaacgact      4560
tttgtcaaat ttttataccg cttttactat attacactct tttgcctagt ggataagcat     4620
aggcaattat cgtctgacct gtaaaaccta tatctcccca aaaatacaat taagcaatat     4680
ttttagcaa acttttctaa cgctaccccg aagaaagcaa atacggctta cttttctgg       4740
aattcgtcga agtcgtctgt taattcctga tgctttgcct atgtctggcg gtcgagaaag     4800
aaacctttct cctgctccta tagcagcctc gttagcctca gctttttttc ctaagactcc     4860
aactctaggc cgtatagtca cacttaggaa gagtagcggt agttccttag ccttttgtct     4920
actacctacg aaatttcgta aataagtttt gcgttcatga ccaaggttta cttaattgcg     4980
tctcgaaaaa gcttgcaaca gttccagtcg tcctagttct gtaaagtatg ttattaattc     5040
gtctccgaca ctagtcagag acgaaaaaaa agacgcaaga taaagaaaaa gtgcaagtgc     5100
```

-continued

```
ctactgcagt caggctaggg cgtttgccac aaacagctat tctttataca acgactcacg    5160
tgacccgacg ggggtacata tgaaaaaaaa ggacgtaagc taggacgtac gaaggaggtc    5220
aaagagtaga aactaaccgt catattacga aaatatccgt ctctgccaaa gctaaacaag    5280
catttggcta acgtattcaa gctcgtttgc cggtactagt tcgggattca gaagctgacg    5340
ggccacaaga cgaacttctt aggcctacga caagcggtag tcagaaaaac ggggccgaca    5400
taagacggaa gacactacta tatttcggtg acgttcgact tatttcgggt gggttatcgc    5460
aaaagcaaag aaaccgccta gaaggaaggt tataagaaga ttataagta ccgtaagttt     5520 tattagggca cagcgtactt tgagttgctc tattagatat attcgaa                  5567
```

<210> SEQ ID NO 3
<211> LENGTH: 1769
<212> TYPE: PRT
<213> ORGANISM: Bacillus subtilis

<400> SEQUENCE: 3

```
Leu Gln Val Asp Ser Arg Gly Ser Pro Met Asp Ser Arg Asn Gly Leu
1               5                   10                  15

Gly Leu Phe Thr Lys Lys Gln Ile Ala Gly Thr Ser Lys Phe Val Phe
            20                  25                  30

Tyr Pro Phe Asn Glu Met Arg Lys Thr Asn Asp Gln Ala Ala Ser His
        35                  40                  45

Trp Gly Cys Phe Phe Tyr Ile Phe Phe Thr Val Ile Pro Lys Gln Asn
    50                  55                  60

Ile Asn Ser Tyr Ile Tyr Arg Lys Glu Ile Phe Ala Glu Met Asn Ile
65                  70                  75                  80

Phe Pro Leu Cys Ile Val Ile Leu Ile Tyr Glu Asn Leu Arg Phe
                85                  90                  95

Phe Ile His Glu Lys Lys Glu Leu Ile Met Asn Arg Phe Ile Leu Ala
            100                 105                 110

Gly Gly Leu Glu Met Gly Arg Ile Lys Thr Lys Ile Thr Ile Leu Leu
        115                 120                 125

Val Leu Leu Leu Leu Leu Ala Gly Gly Tyr Met Tyr Ile Asn Asp Ile
    130                 135                 140

Glu Leu Lys Asp Val Pro Thr Ala Ile Gly Gln Thr Leu Ser Ser Glu
145                 150                 155                 160

Glu Glu Glu Tyr Thr Ile Gln Glu Tyr Lys Val Thr Lys Ile Asp Gly
                165                 170                 175

Ser Glu Tyr His Gly Val Ala Glu Asn Gly Thr Lys Ile Ile Phe Asn
            180                 185                 190

Gly Lys Lys Leu Asn Gln Asp Leu Ser Asp Ile Lys Glu Gly Asp Lys
        195                 200                 205

Ile Lys Ala Tyr Phe Ser Lys Ser Lys Arg Ile Asp Gly Ser Arg Leu
    210                 215                 220

Gln Lys Met Ile Lys Lys His Leu Ser Asp Arg Arg Val Met Phe
225                 230                 235                 240

Cys Phe Ser Gln Ile Val Ser Leu Phe His Cys Val Leu Lys Gly Ser
                245                 250                 255

Leu Pro Ile Arg Thr Asn Glu Arg Leu Tyr Pro Ser Gly Gln Gly Gly
            260                 265                 270

Asn Pro Asp Arg Arg Ser Thr Phe Ala Leu Glu Pro Val Thr Arg Val
        275                 280                 285

His Lys His Ala Val Asp Ser Val Ala Glu Ala Asp Ser Glu Ser Leu
```

-continued

```
                290                 295                 300
Asp Gly Arg Arg Met Met Ser Arg Tyr Ala Lys Cys Leu Lys Met His
305                 310                 315                 320

Ser Val Ile Ser Tyr Cys Val Lys Tyr Leu Lys Pro Arg Ile Phe Tyr
                325                 330                 335

Lys Phe Gly Ala Phe Leu Thr Val Asn Asn Lys Arg Gly Glu Gly Asn
                340                 345                 350

Lys Trp Lys Ser Ile Ile Ser Trp Pro Ile Leu Arg Ser Arg Ala Lys
                355                 360                 365

Asp Arg Pro Asn Pro Ile Arg Ser Ser Ala Leu Leu Ser Arg Thr Asp
370                 375                 380

Lys Leu Ser Glu Trp Ala Pro Ile Asn Met Val Lys Leu Met Gln Lys
385                 390                 395                 400

Phe Met Pro Ser Ile Trp Leu Glu His Met Gln Arg Val Pro Thr Phe
                405                 410                 415

Thr Leu His Ser Asn Arg Ala Ala Ile Thr Glu Lys His Arg His Val
                420                 425                 430

Gln Asn Leu Ser Thr Leu Val Ser Lys Glu Cys Ser Trp Arg Glu Ile
                435                 440                 445

Leu Ile Arg Leu Trp Leu Glu Glu Gly Ser Ala Lys Lys Leu Ala Leu
            450                 455                 460

Arg Gly Lys Ala Ser Trp Gln Thr Arg Arg Gly Met Lys Asn Phe
465                 470                 475                 480

Cys Thr Leu Gly Gln Ala Phe Arg Thr Ser Arg Lys Arg Leu Pro Ala
                485                 490                 495

Leu Thr Ala Arg Leu Pro Ala Arg Val Thr Ala Asn Gly Ser Arg Gln
                500                 505                 510

Arg Leu Gln Asp Arg Met Leu Ser Asn Thr Gly Lys His Thr Lys Ala
                515                 520                 525

Phe Ser Glu Leu Ala Gln Lys Pro Thr Ile Arg Ala Pro Ala Asp Cys
                530                 535                 540

Arg Met Gln Asn Ser Arg Phe Gly Ser Tyr Leu Ile Pro Tyr Ser Arg
545                 550                 555                 560

Phe Leu Arg Thr Leu Lys Phe Ala Ile Lys Arg Arg His Gly Phe Leu
                565                 570                 575

Arg Arg His Ala Gln Thr Arg Lys Arg Lys Asn Gly Phe Gln Leu Ser
                580                 585                 590

Glu Thr Tyr Leu His Leu Lys Pro Ser Ala Phe Lys Phe Leu Met Phe
                595                 600                 605

Arg Ser Arg Lys Lys Ala Ser Cys Arg Cys Met Trp Lys Ala Val Gln
610                 615                 620

Leu Phe Thr Glu Ala Leu Ser Lys Lys Ala Val Phe Lys Lys Ser Ser
625                 630                 635                 640

Ser Ile Leu Pro Ile Asn Ser Glu Glu Arg Met Leu Pro Ala Ser Pro
                645                 650                 655

Val Lys Val Phe Asn Gln Lys Met Ser Pro Tyr Tyr Asn Ser Leu Ile
                660                 665                 670

Pro Lys Ser Ala Val Ile Ser Asn Arg Gln Asn Arg Gln Arg Asn Arg
                675                 680                 685

Met Val Thr Met Phe Thr Gly Ile Ile Glu Glu Thr Gly Thr Ile Glu
                690                 695                 700

Ser Met Lys Lys Ala Gly His Ala Met Ala Leu Thr Ile Lys Cys Ser
705                 710                 715                 720
```

-continued

Lys Ile Leu Glu Asp Val His Leu Gly Asp Ser Ile Ala Val Asn Gly
                725                 730                 735

Ile Cys Leu Thr Val Thr Asp Phe Thr Lys Asn Gln Phe Thr Val Asp
                740                 745                 750

Val Met Pro Glu Thr Val Lys Ala Thr Ser Leu Asn Asp Leu Thr Lys
                755                 760                 765

Gly Ser Lys Val Asn Leu Glu Arg Ala Met Ala Ala Asn Gly Arg Phe
                770                 775                 780

Gly Gly His Phe Val Ser Gly His Val Asp Gly Thr Ala Glu Ile Thr
785                 790                 795                 800

Arg Ile Glu Glu Lys Ser Asn Ala Val Tyr Tyr Asp Leu Lys Met Asp
                805                 810                 815

Pro Ser Leu Thr Lys Thr Leu Val Leu Lys Gly Ser Ile Thr Val Asp
                820                 825                 830

Gly Val Ser Leu Thr Ile Phe Gly Leu Thr Glu Asp Thr Val Thr Ile
                835                 840                 845

Ser Leu Ile Pro His Thr Ile Ser Glu Thr Ile Phe Ser Glu Lys Thr
                850                 855                 860

Ile Gly Ser Lys Val Asn Ile Glu Cys Asp Met Ile Gly Lys Tyr Met
865                 870                 875                 880

Tyr Arg Phe Leu His Lys Ala Asn Glu Asn Lys Thr Gln Gln Thr Ile
                885                 890                 895

Thr Lys Ala Phe Leu Ser Glu Asn Gly Phe Arg Gly Arg Phe Ala Cys
                900                 905                 910

Phe Ile Arg Lys Lys His Trp Thr Leu Lys Lys Ala Lys Ser Ser Ser
                915                 920                 925

Leu Met Met Lys Thr Glu Lys Met Lys Glu Thr Leu Trp Leu Leu Pro
                930                 935                 940

Ser Met Gln Arg Arg Lys Ser Leu Thr Leu Trp Arg His Met Gly Glu
945                 950                 955                 960

Asp Ser Ala Arg Arg Ser Val Arg Lys Ser Gln Thr Gly Leu Ile Phe
                965                 970                 975

Thr Leu Trp Leu Ser Ile Ile Gln Thr Leu Thr Thr Leu His Leu Pro
                980                 985                 990

Ala Thr Ile Val Lys Arg Arg Gln Val Ser Ala Leu Lys Lys Asp Leu
                995                 1000                1005

Leu Pro Phe Lys His Cys Trp Thr Ala Asn Pro Cys His Leu Ile
     1010                1015                1020

Phe Ser Val Arg Gly Thr Phe Phe His Leu Arg Lys Lys Glu Val
     1025                1030                1035

Ser Lys Ala Arg Ala Ile Gln Lys Leu Leu Leu Ile Leu Leu Lys
     1040                1045                1050

Leu Ala Asp Leu Gln Glu Pro Ala Ser Phe Val Lys Leu Met Lys
     1055                1060                1065

Thr Glu Arg Trp Arg Glu Cys Leu Ser Ser Leu Lys Leu Arg Lys
     1070                1075                1080

Ser Ile Asn Lys Ser Pro Leu Arg Ile Phe Asn Thr Val Thr Ile
     1085                1090                1095

Gln His Leu Ser Ser Val Lys Leu Thr Leu Arg Cys Leu Leu Ile
     1100                1105                1110

Leu Gly His Leu Arg Phe Met Asp Thr Gln Met Arg Met Glu Lys
     1115                1120                1125

-continued

```
Ser Met Ser His Leu Trp Glu Met Cys Arg Ser Glu Lys Asn Arg
    1130            1135                1140

Tyr Trp Ser Gly Cys Ile Gln Asn Val Ser Gln Val Thr Cys Leu
    1145            1150                1155

Ala Leu Ile Ala Val Ile Ala Asp Arg Ser Cys Thr Pro Arg Thr
    1160            1165                1170

Lys Leu Pro Gln Lys Ala Val Glu Cys Ser Cys Thr Cys Ala Lys
    1175            1180                1185

Lys Asp Glu Ala Ser Val Ser Ile Asn Lys Leu Ile Ser Phe Arg
    1190            1195                1200

Asn Lys Ala Met Thr Pro Lys Pro Met Arg Arg Leu Asp Ser Cys
    1205            1210                1215

Arg Ile Phe Ala Thr Met Ala Ser Glu His Lys Phe Tyr Ala Thr
    1220            1225                1230

Ser Val Ser Gly Ile Ser Phe Arg Ile Ile Arg Glu Lys Ser Gln
    1235            1240                1245

Ala Leu Lys Ala Thr Asp Ser Val Phe Gln Lys Glu Cys Arg Phe
    1250            1255                1260

Lys Trp Arg Arg Lys Asn Thr Ile Lys Asn Ile Cys Lys Pro Lys
    1265            1270                1275

Thr Ser Val Ile Tyr Phe Ile Ser Asn His Lys Tyr His Lys Lys
    1280            1285                1290

Gly Trp Glu Ser Tyr Glu Tyr His Thr Arg Lys Phe Ser Trp Tyr
    1295            1300                1305

Arg Ser Asn Arg Asn Arg Ser Arg Lys Ile Phe Tyr Tyr Glu Gln
    1310            1315                1320

Ala Ala Glu Arg Ser Arg Arg Cys Ala Ala Gln Thr Trp Arg Arg
    1325            1330                1335

His Lys His Cys Gly Leu Gly Ser Arg Arg Ile Asn Thr Val Cys
    1340            1345                1350

Cys Glu Lys Asn Gly Gly Asn Lys Lys Ile Cys Tyr Tyr His Ile
    1355            1360                1365

Gly His Cys His Gln Arg Arg Asn Asp Thr Leu Arg Leu Cys Leu
    1370            1375                1380

Gln Ser Cys Lys Arg His Arg Ala Ser Ser Lys His Tyr Trp Cys
    1385            1390                1395

Thr Cys His Leu Trp Asn Cys Asn Asn Lys His Arg Thr Gly Tyr
    1400            1405                1410

Arg Ala Cys Arg His Lys Ser Gly Gln Gln Arg Cys Arg Leu Cys
    1415            1420                1425

Cys Phe Cys His Asn Gly Lys Phe Lys Pro Leu Ile Ile Ile Cys
    1430            1435                1440

Lys Gln Phe Lys Asn Met Ala Lys Met Ile Cys Glu Lys Thr Asp
    1445            1450                1455

His Leu Phe Val Ser Val Asn Ser Arg Leu Asp Ile Leu Asp Ile
    1460            1465                1470

Glu Gly Phe Leu Cys Phe Val Ile Lys Asn Arg Leu Lys Arg Leu
    1475            1480                1485

Arg Trp Gly Phe Phe Arg Leu Cys Arg Met Lys Lys Thr Leu Ser
    1490            1495                1500

Ser Phe Ser Arg Gln Leu Arg Thr Thr Lys Arg Ile Gln Thr Ala
    1505            1510                1515

Ser Ser Phe Phe Gly Lys Arg Thr Arg Ile Ser Ser Glu Gln Ser
```

```
                      1520                1525                1530

Glu Ser Lys Lys Arg Ile Leu Arg Leu Arg Ser Gly Ile Ser Val
        1535                1540                1545

Ile Leu Leu Ile Ala Ile Lys Glu Ser Glu Asn Arg Trp Met Leu
        1550                1555                1560

Ser Ile Tyr Ser Lys Arg Lys Tyr Trp Phe Gln Met Asn Arg Arg
        1565                1570                1575

Ala Phe Ser Asn Val Val Lys Val Ser Arg Ile Lys Thr Phe His
        1580                1585                1590

Thr Ile Ile Lys Gln Arg Leu Ser Val Ser Ala Phe Phe Ser Ala
        1595                1600                1605

Phe Tyr Phe Phe Phe Thr Phe Thr Asp Asp Val Ser Pro Ile Pro
        1610                1615                1620

Gln Thr Val Phe Val Asp Lys Lys Tyr Val Ala Glu Cys Thr Gly
        1625                1630                1635

Leu Pro Pro Cys Ile Leu Phe Phe Pro Ala Phe Asp Pro Ala Cys
        1640                1645                1650

Phe Leu Gln Phe Leu Ile Phe Asp Trp Gln Tyr Asn Ala Phe Ile
        1655                1660                1665

Gly Arg Asp Gly Phe Asp Leu Phe Val Asn Arg Leu His Lys Phe
        1670                1675                1680

Glu Gln Thr Ala Met Ile Lys Pro Val Phe Asp Cys Pro Val Phe
        1685                1690                1695

Cys Leu Lys Asn Pro Asp Ala Val Arg His Gln Ser Phe Cys Pro
        1700                1705                1710

Gly Cys Ile Leu Pro Ser Val Met Ile Ser His Cys Lys Leu Asn
        1715                1720                1725

Lys Ala His Pro Ile Ala Phe Ser Phe Leu Trp Arg Ile Phe Leu
        1730                1735                1740

Pro Ile Phe Phe Tyr Phe Met Ala Phe Lys Ile Ile Pro Cys Arg
        1745                1750                1755

Met Lys Leu Asn Glu Ile Ile Tyr Ile Ser Phe
        1760                1765

<210> SEQ ID NO 4
<211> LENGTH: 1740
<212> TYPE: PRT
<213> ORGANISM: Bacillus subtilis

<400> SEQUENCE: 4

Cys Arg Ser Thr Leu Glu Asp Pro Pro Trp Thr Ala Val Thr Ala Leu
1               5                   10                  15

Ala Ser Ser Arg Lys Asn Lys Leu Arg Val Arg Gln Ser Leu Phe Ser
                20                  25                  30

Thr Arg Leu Thr Lys Cys Ala Lys Gln Ile Arg Ile Lys Gln Leu Pro
            35                  40                  45

Ile Gly Ala Ala Phe Phe Ile Ser Phe Leu Arg Ser Ser Pro Lys Asn
        50                  55                  60

Arg Thr Ile Arg Ile Ser Ile Glu Lys Lys Phe Leu Gln Lys Cys Glu
65                  70                  75                  80

Thr Tyr Ser Arg Tyr Ala Ser Leu Tyr Phe Thr Arg Ile Tyr Gly Phe
                85                  90                  95

Leu Phe Met Lys Lys Arg Asn Asn Ser Tyr Glu Ile Asp Ser Tyr Trp
                100                 105                 110
```

-continued

```
Leu Glu Val Lys Trp Glu Glu Lys Pro Arg Leu Pro Phe Cys Cys Phe
        115                 120                 125
Cys Phe Tyr Leu Gln Ala Val Ile Cys Thr Met Ile Leu Ser Arg Met
        130                 135                 140
Phe Arg Gln Gln Leu Asp Lys Pro Cys Pro Arg Lys Lys Arg Asn Thr
145                 150                 155                 160
Pro Ser Arg Asn Ile Lys Arg Lys Leu Thr Ala Gln Ser Ile Met Glu
                165                 170                 175
Gln Lys Thr Glu Arg Lys Ser Ser Thr Glu Lys Asn Ile Arg Ile
        180                 185                 190
Tyr Leu Ile Lys Lys Val Thr Arg Leu Arg Leu Thr Ser Ala Asn Gln
        195                 200                 205
Ser Gly Ser Thr Val Asn Gln Gly Cys Lys Ser Glu Leu Lys Asn Ile
    210                 215                 220
Thr Phe Arg Ile Glu Gly Cys Phe Val Phe Leu Lys Leu Val Tyr Phe
225                 230                 235                 240
Ile Ala Tyr Phe Lys Lys Asp Arg Tyr Asn Asn Gln Gly Gln Met Asn
                245                 250                 255
Lys Asp Cys Ile Leu Arg Gly Arg Val Glu Ile Pro Thr Gly Gly Ser
            260                 265                 270
Lys Ala His Leu Leu Ser Pro Pro Val Cys Ile Ser Thr Arg Trp Ile
        275                 280                 285
Gln Phe Lys Leu Lys Pro Thr Val Lys Val Trp Met Gly Glu Gly Ala
        290                 295                 300
Ala Met Gln Asn Val Lys Cys Ile Val Leu Phe Pro Ile Ala Asn Thr
305                 310                 315                 320
Ser Pro Glu Phe Phe Ile Asn Ser Gly Leu Phe Arg Ile Thr Lys Glu
                325                 330                 335
Gly Arg Glu Thr Asn Gly Arg Val Leu Tyr Glu Ala Gly Leu Arg Ser
            340                 345                 350
Cys Glu Ala Gly Arg Arg Thr Asp Arg Ile Gln Ser Ala Arg Arg Arg
        355                 360                 365
Cys Cys Arg Lys Gly Arg Thr Asn Cys Arg Asn Gly Arg Pro Phe Lys
        370                 375                 380
Ile Trp Ser Ser Cys Arg Ser Ser Cys His Pro Tyr Gly Trp Ser Thr
385                 390                 395                 400
Cys Arg Gly Cys Arg His Leu Arg Tyr Thr Arg Thr Val Gln Pro Leu
                405                 410                 415
Arg Lys Asn Thr Ala Met Cys Arg Ile Asp Tyr Gln Leu Trp Tyr Gln
            420                 425                 430
Lys Ser Val Arg Gly Asp Glu Arg Ser Ser Ala Cys Gly Trp Lys Arg
        435                 440                 445
Asp Gln His Asp Glu Arg Ser Trp His Gly Lys Gly Arg His Pro Gly
        450                 455                 460
Arg Pro Gly Gly Glu Glu Lys Ile Ser Ala Leu Tyr Glu Asp Arg
465                 470                 475                 480
Pro Ser Val Arg His Ala Lys Ser Gly Cys Gln Pro Arg Gln Asp Ser
                485                 490                 495
Tyr Gln His Gly Gln Gln Met Asp His Val Arg Gly Cys Lys Thr Gly
            500                 505                 510
Cys Ser Ala Ile Gln Glu Asn Thr Pro Lys His Phe Ser Arg Ser Trp
        515                 520                 525
His Ser Glu Ser Arg Gln Ser Glu Leu Asn Leu Gln Thr Ala Glu Cys
```

-continued

```
            530                 535                 540
Asn Lys Thr Ala Gly Ser Gly His Thr Tyr Arg Thr Leu Asp Ser Gly
545                 550                 555                 560

Arg Ser Asp Leu Arg Ser Asn Ser Ala Asp Met Asp Phe Tyr Asp Gly
                565                 570                 575

Thr Arg Arg Arg Gly Lys Glu Lys Thr Ala Phe Ser Phe Arg Ser Glu
                580                 585                 590

His Ile Tyr Thr Asn Arg Ala His Ser Asn Ser Cys Phe Glu Asp Pro
                595                 600                 605

Ser Gly Arg Arg His His Val Gly Val Cys Gly Arg Arg Phe Ser Cys
            610                 615                 620

Ser Arg Lys Leu Cys Gln Arg Leu Phe Ser Arg Asn His Leu Leu
625                 630                 635                 640

Phe Cys Pro Thr Asn Arg Arg Asn Ala Cys Ser Gln Leu Asn Leu Arg
                645                 650                 655

Arg Phe Ser Ile Asn Glu Arg Cys Pro Leu Ile Thr Ile His Tyr Asn
                660                 665                 670

Pro Asn Arg Pro Tyr Gln Thr Asp Gly Lys Thr Asp Lys Gly Ile Gly
                675                 680                 685

Trp Pro Cys Leu Gln Glu Leu Ser Lys Lys Gln Ala Gln Ser Asn Pro
            690                 695                 700

Lys Lys Gln Gly Met Gln Trp Pro Leu Leu Asn Ala Gln Arg Phe Arg
705                 710                 715                 720

Met Phe Ile Leu Ala Thr Ala Leu Gln Thr Ala Phe Val Leu Ser Leu
                725                 730                 735

Ile Leu Gln Lys Ile Asn Ser Gln Trp Met Leu Cys Leu Lys Gln Ser
                740                 745                 750

Lys Leu Arg His Met Ile Gln Lys Glu Ala Lys Ile Trp Lys Glu Arg
                755                 760                 765

Trp Arg Gln Thr Ala Val Ser Glu Ala Ile Ser Ser Gln Ala Met Ser
            770                 775                 780

Thr Glu Leu Arg Lys Ser His Glu Leu Lys Arg Lys Ala Thr Gln Phe
785                 790                 795                 800

Thr Met Ile Lys Trp Thr Arg His Gln Lys His Trp Phe Arg Asp Gln
                805                 810                 815

Leu Leu Trp Met Ala Ala Pro Tyr Ser Ala Gln Lys Thr Gln Arg Ser
                820                 825                 830

Pro Tyr Arg Ile Arg Ser Ala Lys Arg Ser Phe Gln Lys Lys Arg Ser
                835                 840                 845

Ala Leu Lys Ile Ser Asn Ala Ile Ser Glu Asn Ile Cys Ile Asp Phe
            850                 855                 860

Cys Ile Lys Pro Met Lys Ile Arg Pro Asn Lys Pro Leu Gln Lys Pro
865                 870                 875                 880

Ser Ala Lys Thr Ala Phe Arg Glu Glu Asp Leu His Val Ser Ser Asp
                885                 890                 895

Arg Arg Ser Thr Gly Arg Phe Lys Lys Arg Ser His His Arg Cys
                900                 905                 910

Arg Arg Gln Arg Lys Arg Leu Cys Gly Ser Cys Arg Ala Cys Asn
            915                 920                 925

Ala Gly Ser His Leu Tyr Gly Asp Thr Trp Glu Arg Thr Asp Leu His
            930                 935                 940

Ala Ala Gln Gly Asn Arg Arg Gln Ala Ser Ser Pro Tyr Gly Ala Tyr
945                 950                 955                 960
```

-continued

```
Arg Leu Ser Pro His Cys Ile Tyr Arg Lys His Arg Pro Ser Asn Glu
            965                 970                 975
Asp Arg Tyr Gln Arg Ser Arg Lys Ile Phe Tyr Arg Ser Ser Ile Ala
            980                 985                 990
Gly Gln Gln Ile Arg Ala Ile Phe  Ser Ala Ser Gly Ala  His Phe Ser
            995                 1000                1005
Thr Asp Cys Glu Lys Arg Arg Cys Pro Glu Lys Arg  Gly Pro Tyr
    1010                1015                1020
Arg Ser Cys Cys Ser Cys Ser Leu Arg Ile Ser Arg  Ser Arg Arg
    1025                1030                1035
His Leu Asn Tyr Glu Arg Arg Asn Asp Gly Glu Ser Ala Ala His
    1040                1045                1050
Asn Cys Glu Lys Ala Ser Ile Lys Asn Asp His His  Gly Phe Asp
    1055                1060                1065
Ser Ile Pro Leu Gln Ser Asp Asn Thr Cys Arg Ala  Ser His Tyr
    1070                1075                1080
Ala Ala Tyr Phe Trp Asp Ile Gly Leu Trp Ile His  Lys Gly Arg
    1085                1090                1095
Trp Lys Arg Ala Cys Arg Ile Cys Asp Gly Arg Cys Ala Val Arg
    1100                1105                1110
Arg Arg Thr Gly Ile Gly Pro Gly Ala Phe Arg Met  Ser His Arg
    1115                1120                1125
Arg Val Trp Leu Ser Ser Leu Leu Arg Thr Ala Ala  Ala Arg Arg
    1130                1135                1140
Ala Glu Pro Asn Cys Arg Arg Pro Trp Ser Ala Pro Val Leu
    1145                1150                1155
Ala Pro Arg Arg Thr Arg His Arg Phe Asn Gln Ile  Lys Ser Leu
    1160                1165                1170
Ala Ser Gly Thr Arg Leu His Arg Arg Ser Gln Gly  Ala Trp Ile
    1175                1180                1185
Leu Ala Gly Ser Ser Gln Leu Trp His Arg Ser Thr  Asn Phe Thr
    1190                1195                1200
Arg Pro Arg Cys Pro Glu Tyr Glu Ala Phe Asp Glu Ser Ala Lys
    1205                1210                1215
Asn Arg Arg Pro Arg Leu Arg Thr Gln Tyr Phe Arg  Lys Ser Ala
    1220                1225                1230
Ala Ser Asn Gly Gly Glu Arg Thr Gln Lys Ile Phe Ala Asn Gln
    1235                1240                1245
Asn Glu Gln Ala Arg Ser Phe Thr Ser Phe Leu Ile  Thr Asn Ile
    1250                1255                1260
Thr Lys Lys Asp Gly Asn His Met Asn Ile Ile Gln  Gly Asn Leu
    1265                1270                1275
Val Gly Thr Gly Leu Lys Ile Gly Ile Val Val Gly  Arg Phe Asn
    1280                1285                1290
Asp Phe Ile Thr Ser Lys Leu Leu Ser Gly Ala Glu  Asp Ala Leu
    1295                1300                1305
Leu Arg His Gly Val Asp Thr Asn Asp Ile Asp Val Ala Trp Val
    1310                1315                1320
Pro Gly Ala Phe Glu Ile Pro Phe Ala Ala Lys Lys  Met Ala Glu
    1325                1330                1335
Thr Lys Lys Tyr Asp Ala Ile Ile Thr Leu Gly Thr  Val Ile Arg
    1340                1345                1350
```

```
Gly Ala Thr Thr His Tyr Asp Tyr Val Cys Asn Glu Ala Ala Lys
1355                1360                1365
Gly Ile Ala Gln Ala Ala Asn Thr Thr Gly Val Pro Val Ile Phe
1370                1375                1380
Gly Ile Val Thr Thr Glu Asn Ile Glu Gln Ala Ile Glu Arg Ala
1385                1390                1395
Gly Thr Lys Ala Gly Asn Lys Gly Val Asp Cys Ala Val Ser Ala
1400                1405                1410
Ile Glu Met Ala Asn Leu Asn Arg Ser Phe Glu Phe Ala Glu Asn
1415                1420                1425
Ser Leu Lys Ile Trp Arg Lys Tyr Asn Val Arg Lys Arg Ile Thr
1430                1435                1440
Tyr Ser Tyr Pro Leu Ile Ala Asp Trp Thr Phe Trp Ile Arg Gly
1445                1450                1455
Phe Tyr Val Asn Ser Leu Lys Ile Val Lys Asp Cys Asp Gly Ala
1460                1465                1470
Ser Phe Val Tyr Ala Glu Lys Arg Pro Ala Ala Ser Ala Asp Asn
1475                1480                1485
Gly Leu Arg Asn Gly Tyr Arg Pro Pro Ala Leu Ser Leu Glu Arg
1490                1495                1500
Gly Arg Gly Tyr Arg Arg Ser Asn Arg Ser Arg Lys Lys Gly Phe
1505                1510                1515
Gly Asp Pro Ala Tyr Gln Cys Glu Ser Phe Ser Ser Pro Ser Arg
1520                1525                1530
Asn Arg Lys Thr Asp Asp Gly Cys Phe Lys Ala Phe Ile Gln Asn
1535                1540                1545
Ala Ser Thr Gly Ser Lys Ile Asn Ala Glu Leu Phe Arg Thr Leu
1550                1555                1560
Ser Arg Ser Ala Gly Ser Arg His Phe Ile Gln Leu Ser Arg Gly
1565                1570                1575
Cys Asp Gln Ser Leu Leu Phe Phe Leu Arg Ser Ile Ser Phe Ser
1580                1585                1590
Arg Ser Arg Met Thr Ser Val Arg Ser Arg Lys Arg Cys Leu Ser
1595                1600                1605
Ile Arg Asn Met Leu Leu Ser Ala Leu Gly Cys Pro His Val Tyr
1610                1615                1620
Phe Phe Phe Leu His Ser Ile Leu His Ala Ser Ser Phe Ser
1625                1630                1635
Ser Leu Ile Gly Ser Ile Met Leu Leu Ala Glu Thr Val Ser Ile
1640                1645                1650
Cys Ser Thr Asp Cys Ile Ser Ser Ser Lys Arg Pro Ser Ser Pro
1655                1660                1665
Lys Ser Ser Thr Ala Arg Cys Ser Ala Arg Ile Arg Met Leu Phe
1670                1675                1680
Ala Ile Ser Leu Phe Ala Pro Ala Val Phe Cys Leu Leu Tyr Lys
1685                1690                1695
Ala Thr Ala Ser Ile Lys Pro Thr Gln Arg Phe Arg Phe Phe Gly
1700                1705                1710
Gly Ser Ser Phe Gln Tyr Ser Ser Asn Ile Ser Trp His Ser Lys
1715                1720                1725
Ser Arg Val Ala Asn Ser Thr Arg Ser Ile Ala Ser
1730                1735                1740
```

<210> SEQ ID NO 5
<211> LENGTH: 1801
<212> TYPE: PRT
<213> ORGANISM: Bacillus subtilis

<400> SEQUENCE: 5

```
Ala Gly Arg Leu Arg Ile Pro His Gly Gln Pro Arg Pro Trp Pro Leu
1               5                   10                  15

His Glu Lys Thr Asn Cys Gly Tyr Val Lys Val Cys Phe Leu Pro Val
            20                  25                  30

Arg Asn Ala Gln Asn Lys Leu Gly Ser Ser Phe Pro Leu Gly Leu
        35                  40                  45

Leu Phe Leu Tyr Leu Phe Tyr Gly His Pro Leu Lys Thr Glu His Lys
    50                  55                  60

Phe Val Tyr Leu Lys Arg Asn Phe Cys Arg Asn Val Lys His Ile Pro
65                  70                  75                  80

Val Met His Arg Tyr Ile Asn Asn Leu Arg Glu Phe Thr Val Phe Tyr
                85                  90                  95

Ser Lys Lys Gly Ile Thr His Met Asn Glu Ile His Ile Gly Trp Arg
            100                 105                 110

Phe Arg Asn Gly Lys Asn Lys Asn Gln Asp Tyr His Ser Val Ser Ala
        115                 120                 125

Phe Ala Phe Thr Cys Arg Arg Leu Tyr Val His Lys Tyr Ala Glu Gly
    130                 135                 140

Cys Ser Asp Ser Asn Trp Thr Asn Leu Val Leu Gly Arg Arg Gly Ile
145                 150                 155                 160

His His Pro Gly Ile Ser Asp Glu Asn Arg Leu Arg Val Ser Trp Ser
                165                 170                 175

Ser Arg Lys Arg Asn Glu Asn His Leu Gln Arg Lys Lys Ile Lys Ser
            180                 185                 190

Gly Phe Ile Tyr Lys Arg Arg Gln Asp Gly Leu Leu Gln Gln Ile Lys
        195                 200                 205

Ala Asp Arg Arg Leu Ile Lys Val Ala Lys Val Asn Asp Lys Thr Ser
    210                 215                 220

Pro Phe Gly Ser Lys Gly Asp Val Leu Phe Phe Ser Asn Cys Lys Phe
225                 230                 235                 240

Ile Ser Leu Arg Thr Leu Lys Arg Ile Ala Ile Thr Asn Lys Asp
                245                 250                 255

Lys Ile Lys Ile Val Ser Phe Gly Ala Gly Trp Lys Ser Arg Pro Ala
            260                 265                 270

Val Val Lys His Ile Cys Phe Arg Ala Arg Asp Pro Cys Ala Ala Arg
        275                 280                 285

Gly Gly Phe Ser Leu Ser Ser Arg Gln Lys Ser Gly Trp Glu Lys Asp
    290                 295                 300

Asp Glu Pro Leu Cys Lys Met Phe Lys Asn Ala Cys Tyr Phe Leu Leu
305                 310                 315                 320

Arg Lys Ile Pro Lys Ala Pro Asn Phe Leu Ile Arg Gly Phe Asp
                325                 330                 335

Gly Lys Gln Lys Arg Gly Gly Lys Gln Met Glu Glu Tyr Tyr Met Lys
            340                 345                 350

Leu Ala Leu Asp Leu Ala Lys Gln Gly Glu Gly Gln Thr Glu Ser Asn
        355                 360                 365

Pro Leu Val Gly Ala Val Val Lys Asp Gly Gln Ile Val Gly Met
    370                 375                 380
```

-continued

```
Gly Ala His Leu Lys Tyr Gly Glu Ala His Ala Glu Val His Ala Ile
385                 390                 395                 400

His Met Ala Gly Ala His Ala Glu Gly Ala Asp Ile Tyr Val Thr Leu
                405                 410                 415

Glu Pro Cys Ser His Tyr Gly Lys Thr Pro Pro Cys Ala Glu Leu Ile
            420                 425                 430

Ile Asn Ser Gly Ile Lys Arg Val Phe Val Ala Met Arg Asp Pro Asn
        435                 440                 445

Pro Leu Val Ala Gly Arg Gly Ile Ser Met Met Lys Glu Ala Gly Ile
    450                 455                 460

Glu Val Arg Glu Gly Ile Leu Ala Asp Gln Ala Glu Arg Leu Asn Glu
465                 470                 475                 480

Lys Phe Leu His Phe Met Arg Thr Gly Leu Pro Tyr Val Thr Leu Lys
                485                 490                 495

Ala Ala Ala Ser Leu Asp Gly Lys Ile Ala Thr Ser Thr Gly Asp Ser
            500                 505                 510

Lys Trp Ile Thr Ser Glu Ala Ala Arg Gln Asp Ala Gln Gln Tyr Arg
        515                 520                 525

Lys Thr His Gln Ser Ile Leu Val Gly Val Gly Thr Val Lys Ala Asp
    530                 535                 540

Asn Pro Ser Leu Thr Cys Arg Leu Pro Asn Val Thr Lys Gln Pro Val
545                 550                 555                 560

Arg Val Ile Leu Asp Thr Val Leu Ser Ile Pro Glu Asp Ala Lys Val
                565                 570                 575

Ile Cys Asp Gln Ile Ala Pro Thr Trp Ile Phe Thr Thr Ala Arg Ala
            580                 585                 590

Asp Glu Glu Lys Lys Lys Arg Leu Ser Ala Phe Gly Val Asn Ile Phe
        595                 600                 605

Thr Leu Glu Thr Glu Arg Ile Gln Ile Pro Asp Val Leu Lys Ile Leu
    610                 615                 620

Ala Glu Glu Gly Ile Met Ser Val Tyr Val Glu Gly Gly Ser Ala Val
625                 630                 635                 640

His Gly Ser Phe Val Lys Glu Gly Cys Phe Gln Glu Ile Ile Phe Tyr
                645                 650                 655

Phe Ala Pro Lys Leu Ile Gly Gly Thr His Ala Pro Ser Leu Ile Ser
            660                 665                 670

Gly Glu Gly Phe Gln Ser Met Lys Asp Val Pro Leu Leu Gln Phe Thr
        675                 680                 685

Asp Ile Thr Gln Ile Gly Arg Asp Ile Lys Leu Thr Ala Lys Pro Thr
    690                 695                 700

Lys Glu Asp Gly Asp His Val Tyr Arg Asn Tyr Arg Arg Asn Arg His
705                 710                 715                 720

Asn Arg Ile His Glu Lys Ser Arg Ala Cys Asn Gly Leu Asn Tyr Met
                725                 730                 735

Leu Lys Asp Phe Arg Gly Cys Ser Ser Trp Arg Gln His Cys Ser Glu
            740                 745                 750

Arg His Leu Ser Asp Cys His Phe Tyr Lys Lys Ser Ile His Ser Gly
        755                 760                 765

Cys Tyr Ala Asn Ser Gln Ser Tyr Val Thr Glu Phe Asn Lys Arg Lys
    770                 775                 780

Gln Ser Lys Ser Gly Lys Ser Asp Gly Gly Lys Arg Pro Phe Arg Arg
785                 790                 795                 800

Pro Phe Arg Leu Arg Pro Cys Arg Arg Asn Cys Gly Asn His Thr Asn
```

-continued

```
                805                 810                 815
Arg Glu Lys Gln Arg Ser Leu Leu Phe Lys Asn Gly Pro Val Ile Asn
            820                 825                 830
Lys Asn Ile Gly Phe Lys Gly Ile Asn Tyr Cys Gly Trp Arg Glu Leu
            835                 840                 845
Asn His Ile Arg Pro Asp Arg Arg His Ser Asp Asp Leu Leu Asn Thr
850                 855                 860
Ala Tyr Asp Gln Arg Asn Asp Leu Phe Arg Lys Asn Asp Arg Leu Ser
865                 870                 875                 880
Glu Tyr Arg Met Arg Tyr Asp Arg Lys Ile Tyr Val Ser Ile Phe Ala
                885                 890                 895
Ser Gln Lys Asp Pro Thr Asn His Tyr Lys Ser Leu Leu Lys Arg Lys
            900                 905                 910
Arg Leu Leu Glu Arg Lys Ile Cys Met Phe His Pro Ile Glu Glu Ala
            915                 920                 925
Leu Asp Ala Leu Lys Lys Gly Glu Val Ile Ile Val Val Asp Asp Glu
            930                 935                 940
Asp Arg Glu Asn Glu Gly Asp Phe Val Ala Leu Ala Glu His Ala Thr
945                 950                 955                 960
Pro Glu Val Ile Asn Phe Met Ala Thr His Gly Arg Gly Leu Ile Cys
                965                 970                 975
Thr Pro Leu Ser Glu Ile Ala Asp Arg Leu Asp Leu His Pro Met
            980                 985                 990
Val Glu His Asn Thr Asp Ser His  His Thr Ala Phe Thr  Val Ser Ile
            995                 1000                1005
Asp His  Arg Glu Thr Lys Thr  Gly Ile Ser Ala Gln  Glu Arg Ser
    1010                1015                1020
Phe Thr  Val Gln Ala Leu Leu  Asp Ser Lys Ser Val  Pro Ser Asp
    1025                1030                1035
Phe Gln  Arg Pro Gly His Ile  Phe Pro Leu Ile Ala  Lys Lys Gly
    1040                1045                1050
Gly Val  Leu Lys Ser Ala Gly  His Thr Glu Ala Ala  Val Asp Leu
    1055                1060                1065
Ala Glu  Ala Cys Gly Ser Pro  Gly Ala Gly Val Ile  Cys Glu Ile
    1070                1075                1080
Met Asn  Glu Asp Gly Thr Met  Ala Arg Val Pro Glu  Leu Ile Glu
    1085                1090                1095
Ile Ala  Lys Lys His Gln Leu  Lys Met Ile Thr Ile  Lys Asp Leu
    1100                1105                1110
Ile Gln  Tyr Arg Tyr Asn Leu  Thr Thr Leu Val Glu  Arg Glu Val
    1115                1120                1125
Asp Ile  Thr Leu Pro Thr Asp  Phe Gly Thr Phe Lys  Val Tyr Gly
    1130                1135                1140
Tyr Thr  Asn Glu Val Asp Gly  Lys Glu His Val Ala  Phe Val Met
    1145                1150                1155
Gly Asp  Val Pro Phe Gly Glu  Pro Val Leu Val Arg  Val His
    1160                1165                1170
Ser Glu  Cys Leu Thr Gly Asp  Val Phe Gly Ser His  Arg Cys Asp
    1175                1180                1185
Cys Gly  Pro Gln Leu His Ala  Ala Leu Asn Gln Ile  Ala Ala Glu
    1190                1195                1200
Gly Arg  Gly Val Leu Leu Tyr  Leu Arg Gln Glu Gly  Arg Gly Ile
    1205                1210                1215
```

-continued

```
Gly Leu Ile Asn Lys Leu Lys Ala Tyr Lys Leu Gln Glu Gln Gly
    1220            1225                1230

Tyr Asp Thr Val Glu Ala Asn Glu Ala Leu Gly Phe Leu Pro Asp
    1235            1240                1245

Leu Arg Asn Tyr Gly Ile Gly Ala Gln Ile Leu Arg Asp Leu Gly
    1250            1255                1260

Val Arg Asn Met Lys Leu Leu Thr Asn Asn Pro Arg Lys Ile Ala
    1265            1270                1275

Gly Leu Glu Gly Tyr Gly Leu Ser Ile Ser Glu Arg Val Pro Leu
    1280            1285                1290

Gln Met Glu Ala Lys Glu His Asn Lys Lys Tyr Leu Gln Thr Lys
    1295            1300                1305

Met Asn Lys Leu Gly His Leu Leu His Phe Ser Gln Ile Ser Gln
    1310            1315                1320

Lys Arg Met Gly Ile Ile Ile Ser Tyr Lys Glu Ile Leu Val Gln
    1325            1330                1335

Val Leu Lys Ser Glu Ser Glu Asp Leu Met Ile Leu Leu Arg Ala
    1340            1345                1350

Ser Cys Ala Glu Gln Lys Met Arg Cys Ser Asp Met Ala Thr Gln
    1355            1360                1365

Met Thr Leu Met Trp Leu Gly Phe Gln Ala His Leu Lys Tyr Arg
    1370            1375                1380

Leu Leu Arg Lys Lys Trp Arg Lys Gln Lys Asn Met Met Leu Leu
    1385            1390                1395

Ser His Trp Ala Leu Ser Ser Glu Ala Gln Arg His Ile Thr Ile
    1400            1405                1410

Met Ser Ala Met Lys Leu Gln Lys Ala Ser Arg Lys Gln Gln Thr
    1415            1420                1425

Leu Leu Val Tyr Leu Ser Ser Leu Glu Leu Gln Leu Lys Thr Ser
    1430            1435                1440

Asn Arg Leu Ser Ser Val Pro Ala Gln Lys Arg Ala Thr Lys Val
    1445            1450                1455

Ile Val Leu Phe Leu Pro Leu Lys Trp Gln Ile Thr Ala His Leu
    1460            1465                1470

Asn Asn Leu Leu Lys Thr Val Lys Tyr Gly Glu Asn Asp Ile Met
    1475            1480                1485

Glu Asn Gly Ser Pro Ile Arg Ile Arg Gln Thr Gly His Phe Gly
    1490            1495                1500

Tyr Arg Gly Val Phe Met Leu Ile Arg Tyr Lys Lys Ser Phe Glu
    1505            1510                1515

Lys Ile Ala Met Gly Leu Leu Ser Phe Met Pro Asn Glu Lys Asp
    1520            1525                1530

Leu Lys Gln Leu Gln Gln Thr Ile Lys Asp Tyr Glu Thr Asp Thr
    1535            1540                1545

Asp Arg Gln Leu Phe Leu Trp Lys Glu Asp Glu Asp Ile Val Gly
    1550            1555                1560

Ala Ile Gly Val Glu Lys Lys Asp Ser Glu Val Glu Ile Arg His
    1565            1570                1575

Ile Ser Val Asn Pro Ser His Arg His Gln Gly Ile Gly Lys Gln
    1580            1585                1590

Met Met Asp Ala Leu Lys His Leu Phe Lys Thr Gln Val Leu Val
    1595            1600                1605
```

-continued

```
Pro Asn Glu Leu Thr Gln Ser Phe Phe Glu Arg Cys Gln Gly Gln
    1610                1615                1620

Gln Asp Gln Asp Ile Ser Tyr Asn Asn Ala Glu Ala Val Ile Ser
    1625                1630                1635

Leu Cys Phe Phe Phe Cys Val Leu Phe Leu Phe His Val His Gly
    1640                1645                1650

Arg Gln Ser Asp Pro Ala Asn Gly Val Cys Arg Glu Ile Cys Cys
    1655                1660                1665

Val His Trp Ala Ala Pro Met Tyr Thr Phe Phe Ser Cys Ile Arg
    1670                1675                1680

Ser Cys Met Leu Pro Pro Val Ser His Leu Leu Ala Val Cys Phe
    1685                1690                1695

Tyr Arg Gln Arg Arg Phe Arg Phe Val Arg Lys Pro Ile Ala Val
    1700                1705                1710

Arg Ala Asn Gly His Asp Gln Ala Leu Ser Leu Arg Leu Pro Gly
    1715                1720                1725

Val Leu Leu Glu Glu Ser Gly Cys Cys Ser Pro Ser Val Phe Leu
    1730                1735                1740

Pro Arg Leu Tyr Ser Ala Phe Cys Asp Asp Ile Lys Pro Leu Gln
    1745                1750                1755

Ala Glu Ser Pro Pro Asn Ser Val Phe Val Ser Leu Ala Asp Leu
    1760                1765                1770

Pro Ser Asn Ile Leu Leu Ile Phe His Gly Ile Gln Asn Asn Pro
    1775                1780                1785

Val Ser His Glu Thr Gln Arg Asp Asn Leu Tyr Lys Leu
    1790                1795                1800

<210> SEQ ID NO 6
<211> LENGTH: 1778
<212> TYPE: PRT
<213> ORGANISM: Bacillus subtilis

<400> SEQUENCE: 6

Cys Thr Ser Glu Leu Pro Asp Gly Met Ser Leu Arg Leu Pro Arg Pro
1               5                   10                  15

Arg Lys Val Phe Phe Cys Ile Ala Pro Val Asp Phe Asn Thr Lys Gly
            20                  25                  30

Asn Leu Ser Ile Arg Leu Val Phe Ser Ala Ala Glu Trp Gln Pro Gln
        35                  40                  45

Lys Lys Ile Lys Lys Val Thr Met Gly Phe Cys Phe Met Phe Glu Tyr
50                  55                  60

Ile Leu Phe Ser Ile Lys Ala Ser Ile His Phe Met Asn Gly Asn His
65                  70                  75                  80

Met Thr Ile Asn Ile Ile Ser Phe Lys Arg Asn Lys Ile Ser Phe Phe
                85                  90                  95

Ser Tyr Ser Met His Ile Phe Leu Asn Met Asn Ala Pro Pro Lys Ser
            100                 105                 110

Ile Pro Leu Ile Phe Val Leu Ile Val Met Arg Asn Thr Ser Lys Ser
        115                 120                 125

Lys Ser Ala Pro Pro Ile Tyr Met Phe Ser Ile Ser Ser Phe Ser Thr
    130                 135                 140

Gly Val Ala Ile Pro Cys Val Lys Asp Glu Ser Ser Ser Ser Tyr Val
145                 150                 155                 160

Met Trp Ser Tyr Leu Thr Val Phe Ile Ser Pro Glu Ser Tyr Pro Thr
                165                 170                 175
```

-continued

```
Ala Ser Phe Pro Val Phe Ile Met Lys Leu Pro Phe Phe Asn Phe Ser
            180                 185                 190

Lys Asp Ser Ile Phe Ser Pro Ser Leu Ile Leu Ala Lys Leu Leu Asp
        195                 200                 205

Phe Arg Ile Ser Pro Asp Leu Asn Cys Phe His Ile Ile Leu Phe Cys
        210                 215                 220

Arg Glu Ser Arg Leu Thr Ile Asn Gln Lys Glu Ile Thr Leu Lys Asn
225                 230                 235                 240

Gln Thr Ser Phe Pro Asp Ser Tyr Tyr Gly Ile Leu Val Phe Ser Tyr
                245                 250                 255

Leu Asn Tyr Gly Glu Pro Cys Pro Pro Phe Gly Ser Arg Arg Tyr Tyr
            260                 265                 270

Leu Val Asn Ala Lys Ser Gly Thr Val Arg Thr Cys Leu Cys Ala Thr
        275                 280                 285

Ser Glu Thr Ala Ser Ala Ser Leu Ser Leu Arg Ser Pro Leu Leu Ile
    290                 295                 300

Ile Leu Arg Ala Phe His Lys Phe Ile Cys Leu Thr Ile Glu Gln Thr
305                 310                 315                 320

Phe Tyr Arg Phe Gly Arg Ile Lys Leu Asn Pro Ala Lys Lys Val Thr
                325                 330                 335

Phe Leu Leu Leu Pro Ser Pro Phe Leu His Phe Leu Ile Ile His Leu
            340                 345                 350

Gln Gly Ile Lys Arg Leu Leu Ala Phe Ser Leu Gly Phe Gly Ile Arg
        355                 360                 365

Glu Asp Ala Ser Asn Asp Tyr Leu Val Ser Leu Asn Asp Ser His Ala
    370                 375                 380

Gly Met Phe Ile Thr Phe Ser Met Cys Phe Asn Met Gly Asp Met His
385                 390                 395                 400

Ser Ser Cys Met Cys Leu Thr Gly Val Asn Val Asn Cys Glu Phe Arg
                405                 410                 415

Ala Ala Met Val Ser Phe Cys Arg Trp Thr Cys Phe Gln Asn Asp Val
            420                 425                 430

Arg Thr Asp Phe Ser His Glu His Arg His Ser Ile Arg Ile Arg Lys
        435                 440                 445

His Ser Ser Ser Pro Asp Ala His His Phe Phe Ser Ala Asn Leu Tyr
    450                 455                 460

Pro Phe Ala Asp Gln Cys Val Leu Arg Leu Pro Gln Ile Phe Phe Lys
465                 470                 475                 480

Gln Val Lys His Pro Cys Ala Lys Arg Val Asp Arg Phe Arg Ser Gly
                485                 490                 495

Ala Lys Val Ala Leu Tyr Ser Gly Ala Arg Thr Val Ala Phe Pro Asp
            500                 505                 510

Arg Leu Ser Cys Ser Leu Ile Ser Leu Leu Val Pro Phe Cys Val Leu
        515                 520                 525

Ala Asn Asp Ser Asn Ala Cys His Phe Gly Val Ile Arg Ala Gly Ala
    530                 535                 540

Ser Gln Arg Ile Tyr Cys Phe Leu Arg Asn Pro Asp Tyr Lys Ile Gly
545                 550                 555                 560

Tyr Glu Arg Asn Arg Leu Val Ser Phe His Asn Ala Ile Leu Tyr Arg
                565                 570                 575

Arg Cys Pro Asn Lys Arg Arg Cys Ala Cys Val Leu Phe Leu Phe Phe
            580                 585                 590
```

```
Pro Lys Ser Glu Ser His Val Tyr Lys Cys Lys Phe Gly Leu Ala Asn
        595                 600                 605

Leu Asn Arg Ile Asn Gln Leu Asp Arg Phe Phe Ala Asp His Arg His
        610                 615                 620

Ile His Phe Ala Thr Ser Asn Val Ser Ala Lys Asp Phe Phe Ala Thr
625                 630                 635                 640

Lys Leu Phe Asp Asp Glu Ile Lys Gly Arg Phe Asp Ser Ser Arg Met
                645                 650                 655

Ser Gly Ala Asp Gly Thr Phe Thr Lys Leu His Phe Ile Asp Gly Leu
                660                 665                 670

Glu Ser Ile Tyr Gly Leu Asp Ala Thr Ile Asp Phe Gln Arg Cys Phe
        675                 680                 685

Arg Cys Leu Phe Leu Ile Thr Val Met Asn Val Pro Ile Ile Ser Ser
        690                 695                 700

Val Pro Val Ile Ser Asp Met Phe Phe Ala Pro Cys Ala Ile Ala Lys
705                 710                 715                 720

Val Ile Leu His Glu Phe Ile Lys Ser Ser Thr Arg Pro Ser Leu Met
                725                 730                 735

Ala Thr Phe Pro Met Gln Arg Val Thr Val Ser Lys Val Phe Phe Asn
                740                 745                 750

Val Thr Ser Thr Ile Gly Ser Val Thr Leu Ala Val Asp Ser Phe Ser
        755                 760                 765

Lys Val Phe Pro Leu Leu Thr Phe Arg Ser Leu Ala Ile Ala Ala Phe
        770                 775                 780

Pro Arg Lys Pro Pro Trp Lys Thr Glu Pro Trp Thr Ser Pro Val Ala
785                 790                 795                 800

Ser Ile Val Arg Ile Ser Ser Phe Leu Leu Ala Thr Ser Lys Phe Ile
                805                 810                 815

Ser Gly Asp Asn Val Phe Val Asn Thr Lys Phe Pro Asp Ile Val Thr
                820                 825                 830

Ser Pro Thr Leu Lys Val Met Asn Pro Arg Val Ser Ser Val Thr Val
        835                 840                 845

Ile Glu Lys Ile Gly Cys Val Ile Leu Ser Val Ile Lys Glu Ser Phe
        850                 855                 860

Val Ile Pro Glu Leu Thr Phe Ile Ser His Ser Ile Ile Pro Phe Tyr
865                 870                 875                 880

Ile Tyr Arg Asn Lys Cys Leu Ala Leu Ser Phe Leu Val Trp Cys Val
                885                 890                 895

Met Val Phe Ala Lys Lys Leu Ser Phe Pro Lys Leu Pro Leu Asn Ala
                900                 905                 910

His Lys Met Arg Tyr Phe Phe Cys Gln Val Ser Phe Phe Ala Phe Asp
        915                 920                 925

Asp Asp Asn Tyr Ile Ile Phe Val Ser Phe Ile Phe Ser Val Lys His
        930                 935                 940

Ser Lys Gly Leu Met Cys Arg Arg Phe Asp Asn Val Lys His Arg Cys
945                 950                 955                 960

Met Pro Ser Ser Gln Asp Ala Arg Arg Glu Thr Leu Phe Asp Cys Val
                965                 970                 975

Pro Lys Ile Lys Val Arg His Asn Leu Met Ile Cys Val Arg Val Val
                980                 985                 990

Ser Cys Lys Gly Tyr Ala Tyr Val  Met Thr Phe Arg Leu  Cys Thr Asp
        995                 1000                1005

Ala Ser  Leu Phe Ser Arg Lys  Gly Asn Leu Cys Gln  Gln Val Ala
```

-continued

```
                1010                1015                1020
Phe Gly His Trp Arg Ile Lys Leu Thr Arg Pro Val Asn Lys Trp
    1025                1030                1035

Gln Asn Arg Phe Phe Ser Thr Asp Gln Phe Ala Arg Ala Met Cys
    1040                1045                1050

Phe Ser Ser Asn Ile Lys Ser Phe Ser Ala Ser Arg Trp Ser Gly
    1055                1060                1065

Ala Asp Asn Thr Phe Asn His Ile Phe Val Ser Arg His Arg Ser
    1070                1075                1080

His Arg Leu Glu Asn Phe Asn Arg Phe Leu Met Leu Phe His Asp
    1085                1090                1095

Gly Asn Leu Ile Gln Asn Leu Val Thr Val Ile Gln Cys Cys Lys
    1100                1105                1110

Asp Leu Thr Phe Asn Val Asn Arg Gln Arg Ser Ile Lys Pro Cys
    1115                1120                1125

Lys Leu Asn Ile Ser Val Cys Ile Leu Tyr Ile Ser Phe Leu Met
    1130                1135                1140

Asp Cys Lys His His Ser Ile His Arg Glu Ser Phe Phe Tyr Gln
    1145                1150                1155

Asp Pro His Met Phe Thr Glu Cys Thr Val His Lys Ala Arg Met
    1160                1165                1170

Ala Thr Ile Ala Ser Arg Leu Gln Val Gly Arg Gln Val Leu Asn
    1175                1180                1185

Gly Cys Phe Ala Thr Ser His Glu Gln Val Gln Ala Leu Phe Ser
    1190                1195                1200

Ser Ala Asp Thr Asp Ile Phe Phe Ser Ile Leu Lys Leu Phe Leu
    1205                1210                1215

Ala Ile Val Gly Tyr Phe Gly Ile Leu Arg Lys Ser Glu Gln Arg
    1220                1225                1230

Ile Lys Ala Val Ile Ala Asp Ser Cys Leu Asn Ala Val Glu Thr
    1235                1240                1245

Asp Pro Ile His Leu Lys Gln Arg Ile Ile Arg Ser Phe Asp Cys
    1250                1255                1260

Ala Lys Phe Ala Val Ser Glu Thr Asn Phe Ser His Arg Lys Leu
    1265                1270                1275

His Leu Arg Phe Phe Val Ile Phe Phe Ile Gln Leu Gly Phe His
    1280                1285                1290

Val Leu Thr Met Lys Met Glu Leu Leu Tyr Leu Phe Pro His Ser
    1295                1300                1305

Asp Tyr Ser Tyr Val Leu Phe Asn Leu Gln Tyr Leu Asp Phe Arg
    1310                1315                1320

Phe Arg Leu Leu Phe Ile His Asn Ser Cys Ala Ala Ser Arg Leu
    1325                1330                1335

Leu Leu His Ala Ala Val His Arg Leu Cys Leu His Cys Gln His
    1340                1345                1350

Pro Lys Pro Glu Leu Arg Met Gln Phe Val Thr Gln Gln Ser Phe
    1355                1360                1365

Phe Pro Pro Phe Leu Phe Ile His His Met Pro Cys Gln Leu Arg
    1370                1375                1380

Leu Ser Val Asn Arg Asn His Arg Cys His Leu Gln Leu Leu Cys
    1385                1390                1395

Arg Ala Leu Leu Leu Cys Gln His Val Gln Arg Gln Phe Gln Leu
    1400                1405                1410
```

```
Leu Gln Phe Cys Arg Val Pro Arg Ala His Arg Cys Leu Leu Pro
    1415                1420                1425

Cys Cys Leu His Leu Asn His Gln Lys Gln Trp Gln Phe Pro Leu
    1430                1435                1440

Asn Leu Gly Ser Met Gln Ile Ile Gln Gln Phe Cys Asn Leu Phe
    1445                1450                1455

Ile Ala Phe Ile Ile Tyr His Ser Phe Val Ser Arg Asn Thr Asp
    1460                1465                1470

Thr Leu Leu Leu Ser Ser Met Lys Ser Ile Ser Pro Asn Lys His
    1475                1480                1485

Asn Thr Ile Phe Phe Arg Lys Phe Leu Asn Arg His Pro Lys Lys
    1490                1495                1500

Arg Lys His Arg Ile Phe Phe Val Lys Leu Leu Lys Leu Leu Cys
    1505                1510                1515

Asn Leu Val Val Phe Arg Ile Cys Val Ala Leu Glu Lys Lys Pro
    1520                1525                1530

Phe Leu Val Leu Ile Asp Asp Ser Cys Asp Ser Asp Phe Phe Leu
    1535                1540                1545

Ile Arg Leu Asn Leu Asp Pro Met Asp Thr His Ile Arg Arg Met
    1550                1555                1560

Ala Met Leu Ser Asp Ser Phe Leu His His Ile Ser Leu Met Glu
    1565                1570                1575

Phe Arg Leu Tyr Gln Asn Trp Ile Phe Arg Leu Ala Lys Glu Phe
    1580                1585                1590

Thr Thr Leu Thr Leu Leu Ile Leu Val Asn Val Ile Ile Leu Cys
    1595                1600                1605

Leu Ser His Asp Thr Glu Ala Lys Lys Glu Ala Asn Lys Lys Lys
    1610                1615                1620

Val Asn Val Ser Ser Thr Leu Gly Ile Gly Cys Val Thr Asn Thr
    1625                1630                1635

Ser Leu Phe Tyr Thr Ala Ser His Val Pro Ser Gly Gly His Ile
    1640                1645                1650

Ser Lys Lys Gly Ala Asn Ser Gly Ala His Lys Arg Trp Asn Arg
    1655                1660                1665

Met Lys Ser Gln Cys Tyr Leu Ala Lys Ile Pro Leu Ser Pro Lys
    1670                1675                1680

Ser Lys Asn Thr Phe Arg Asn Cys Leu Asn Ser Cys Val Ala Met
    1685                1690                1695

Ile Leu Gly Thr Lys Ser Gln Gly Thr Asn Gln Lys Phe Phe Gly
    1700                1705                1710

Ser Ala Thr Arg Trp Asp Lys Gln Gly Pro Gln Ile Arg Gly Glu
    1715                1720                1725

Thr Ile Ile Tyr Leu Trp Gln Leu Ser Phe Leu Ala Trp Gly Ile
    1730                1735                1740

Ala Asn Glu Asn Arg Gln Arg Ile Lys Arg Gly Ile Asn Lys Tyr
    1745                1750                1755

Lys Met Ala Asn Leu Ile Ile Gly His Arg Met Phe Ser Leu Ser
    1760                1765                1770

Ile Ile Ile Leu Lys
    1775

<210> SEQ ID NO 7
<211> LENGTH: 1771
```

<212> TYPE: PRT
<213> ORGANISM: Bacillus subtilis

<400> SEQUENCE: 7

```
Gln Leu Asp Val Arg Ser Ser Gly Gly His Val Ala Thr Val Ala Lys
1               5                   10                  15

Ala Glu Glu Arg Phe Phe Leu Asn Arg Thr Arg Leu Lys Asn Glu Val
            20                  25                  30

Arg Lys Val Phe His Ala Phe Cys Ile Leu Ile Leu Cys Ser Gly Met
        35                  40                  45

Pro Ala Ala Lys Lys Ile Asp Lys Lys Arg Asp Asp Gly Leu Phe Leu
    50                  55                  60

Val Tyr Ile Arg Ile Asp Ile Ser Phe Phe Asn Lys Cys Phe His Ser
65                  70                  75                  80

Val Tyr Glu Arg Ala Asp Asn Tyr Tyr Asn Val Leu Ile Pro Lys Lys
                85                  90                  95

Asn Met Phe Phe Leu Phe Leu Glu Tyr Ser His Ile Ser Glu Tyr Gln
            100                 105                 110

Ser Ser Thr Phe His Ser Ser Tyr Phe Gly Leu Asn Gly Asn Gln His
        115                 120                 125

Lys Gln Lys Lys Cys Ala Thr Ile His Val Tyr Ile Ile Asn Leu Gln
130                 135                 140

Leu Ile Asn Arg Cys Cys Asn Ser Leu Gly Gln Gly Arg Phe Phe Leu
145                 150                 155                 160

Phe Val Gly Asp Leu Phe Ile Phe His Arg Phe Asn Val Ala Leu Ile
                165                 170                 175

Met Ser Tyr Cys Phe Val Ser Arg Phe Asp Asp Glu Val Ser Phe Phe
            180                 185                 190

Ile Leu Ile Arg Ile Tyr Phe Phe Thr Val Leu Asn Leu Ser Val Glu
        195                 200                 205

Ala Phe Leu Pro Asp Val Thr Leu Pro Gln Leu Leu Ser His Asn Phe
    210                 215                 220

Phe Met Val Lys Arg Ile Ser Pro His His Lys Thr Lys Arg Leu Asn
225                 230                 235                 240

Tyr Thr Lys Met Ala Tyr Lys Leu Phe Ser Arg Leu Leu Trp Tyr Pro
                245                 250                 255

Cys Ile Phe Leu Ser Gln Ile Arg Arg Pro Leu Thr Ser Ile Gly Val
            260                 265                 270

Pro Pro Leu Leu Ala Cys Lys Ser Leu Gly His Gly Thr His Met Leu
        275                 280                 285

Val Arg His Ile Asn Leu Ser Phe Gly Val Thr Phe Thr Gln Ile Pro
    290                 295                 300

Ser Pro His His Ala Ala Ile Cys Phe Thr Phe His Met Thr Asn Asn
305                 310                 315                 320

Gly Ile Ala Tyr Phe Val Leu Gly Ser Asn Lys Ile Phe Glu Pro Ser
                325                 330                 335

Lys Gln Arg Tyr Ile Val Phe Ser Pro Leu Ser Val Phe Pro Leu Thr
            340                 345                 350

Asn Tyr Ser Ala Pro Arg Leu Asp Gln Ser Ala Pro Arg Leu Val Ser
        355                 360                 365

Arg Ile Trp Asp Ala Arg Arg Gln Gln Arg Leu Pro Arg Val Phe
    370                 375                 380

Gln Arg Phe Pro Arg Gly Asn Leu Ile His His Leu Glu His Leu Leu
385                 390                 395                 400
```

-continued

```
Glu His Trp Gly Tyr Pro Gln Leu Val His Leu Pro His Arg Cys Lys
                405                 410                 415
Arg Val Arg Val Thr Cys Gly Asn Arg Phe Val Ala Met His Leu
        420                 425                 430
Ile Ser Ser Gln Tyr Phe Leu Thr Arg Pro Ser Ser Leu Asp Asp Ala
            435                 440                 445
Gln Pro Gln Phe Leu Ser Cys Ser Ser Leu Leu Gln Cys Gln Pro Leu
450                 455                 460
Pro Leu Cys Gly Pro Leu Gly Pro Pro Ser Ala Ser His Phe Ile Glu
465                 470                 475                 480
Ala Ser Ser Leu Gly Glu Thr Arg Ala Leu Leu Pro Gln Trp Gly
                485                 490                 495
Gln Arg Cys Ser Leu Trp Cys Pro His Cys Cys Ile Ser Thr Leu Pro
            500                 505                 510
Gln Leu Val Pro His Glu Ala Ile Cys Ser Phe Val Gly Phe Cys Lys
            515                 520                 525
Leu Arg Leu Gln Cys Leu Ser Leu Arg Cys Asp Ser Ser Leu Arg Cys
530                 535                 540
Val Ala Ser His Leu Leu Val Ala Pro Glu Pro Val Gln Tyr Arg Val
545                 550                 555                 560
Arg Ser Glu Gln Pro Arg Leu Ser Lys Arg Asp Phe Leu Ala Ser Met
                565                 570                 575
Ser Lys Ser Pro Val Arg Leu Arg Pro Phe Ser Phe Val Ala Lys Leu
            580                 585                 590
Lys Arg Leu Ser Cys Ile Val Gln Phe Arg Ala Cys Glu Phe Glu Gln
            595                 600                 605
His Lys Ser Ser Gly Leu Pro Leu Leu Cys Thr Pro Thr His Pro Leu
        610                 615                 620
Arg Asn Leu Gln Glu Arg Phe Ser Gln Leu Leu Ser Asn Glu Leu Phe
625                 630                 635                 640
Arg Arg Asn Gln Gly Val Leu Arg Leu Phe Ala His Glu Trp Ser Leu
                645                 650                 655
Arg Arg His Leu Asn Glu Ile Leu Ser Leu His Gly Arg Ile Val Ile
            660                 665                 670
Gln Tyr Leu Gly Phe Arg Gly His Tyr Val Ser Pro Leu Val Ser Leu
            675                 680                 685
Pro Ile Pro His His Gly His Lys Cys Ser Asn Asp Phe Phe Cys Ala
        690                 695                 700
Cys Asp Phe Gly His Phe Phe Cys Pro Met Cys His Gly Ser Asn Phe
705                 710                 715                 720
Ala Leu Asn Leu Ile Asn Met Lys Ala Val Ala Asn Cys His Val Ala
                725                 730                 735
Asn Thr Gln Ser Asp Ser Ile Lys Cys Phe Ile Leu Glu Cys His Ile
            740                 745                 750
Asn His Arg Phe Cys Asp Phe Ser Arg Gln Ile Ile Cys Phe Ser Ala
            755                 760                 765
Phe Tyr Ile Gln Phe Ser Arg His Arg Cys Val Ala Thr Glu Ser Ala
        770                 775                 780
Met Glu Asp Ala Met Asp Val Ser Ser Arg Phe Asp Cys Ser Asn Phe
785                 790                 795                 800
Leu Phe Ala Val Cys Asn Val Ile Ile Phe His Val Arg Cys Phe Cys
                805                 810                 815
```

-continued

```
Gln Asn Leu Ser Asn Ser His Ile Ala His Ala Gly Tyr Glu Ala Gln
            820                 825                 830

Cys Phe Val Cys His Arg Asp Gly Tyr Arg Met Arg Asp Ala Phe Arg
        835                 840                 845

Asp Lys Phe Phe Arg Asp Ala Arg Phe His Ile Asp Phe Ala Ile His
    850                 855                 860

Asp Ser Phe Ile His Ile Ser Lys Gln Met Phe Gly Ile Phe Ile Leu
865                 870                 875                 880

Gly Leu Leu Gly Asn Cys Phe Gly Glu Ala Phe Val Ala Lys Leu Ser
                885                 890                 895

Ser Ser Lys Cys Thr Glu Asp Ser Leu Leu Val Pro Arg Lys Leu
            900                 905                 910

Phe Leu Arg Leu Arg Gln Leu His His Leu Cys Leu Phe His Leu Leu
        915                 920                 925

Ser Gln Pro Glu Gln Arg Ala His Leu Ala Pro Leu Ser Pro Ser Val
    930                 935                 940

His Ser Leu Val Ser Arg Cys Ala Ala His Pro Phe Arg Leu Cys Ala
945                 950                 955                 960

Gln Asp Glu Gly Pro Gln Ala Tyr Tyr Leu Ser Glu Gly Cys Gln Met
                965                 970                 975

Arg Leu Cys Leu Gly Asp His Phe Ser Ser Leu Tyr Arg Glu Leu Phe
            980                 985                 990

Ile Lys Arg Glu Leu Met Ala Pro Cys Cys Ile Arg Ala Met Gln Asn
        995                 1000                1005

Glu Ala Asp Pro Ala Cys Lys Glu Val Ser Gln Ser Phe Leu Leu
    1010                1015                1020

His Gly Ser Phe Arg Pro Gly Tyr Leu Leu Gln Gln Gln Asp Gln
    1025                1030                1035

Gln Leu Lys Arg Ile Glu Leu Leu Arg Arg Lys His Phe Ser His
    1040                1045                1050

Leu Arg Phe Ser Pro Ser Leu Ala Gln Ala Gln Phe Gln Ser Phe
    1055                1060                1065

Ala Asp Ile Leu Phe Ser Trp Pro Asn Ser Glu Ile Gly Asn Cys
    1070                1075                1080

Asp Ser Leu Val Gln Arg Ala His Leu Gln Cys Ala Ala Gln Asn
    1085                1090                1095

Gln Ser Met Pro Lys His Ile Cys Leu His Pro Leu His Phe Leu
    1100                1105                1110

Ala His Arg Met Gln Ser Pro Leu His Ala Thr Arg Leu Leu Val
    1115                1120                1125

Pro Ile Pro Gly Pro Ala Asn Leu Ile Asp Leu His Arg Thr Gly
    1130                1135                1140

Ser Glu Asp Ser His Asn Arg Val Ala Ala Ala Arg Arg Ala Ser
    1145                1150                1155

Gly Phe Gln Arg Leu Leu Gly His Leu Ala Gly Thr Ser Ala Gly
    1160                1165                1170

Leu Leu Val Leu Cys Arg Asn Leu Tyr Ile Leu Leu Lys Tyr Ala
    1175                1180                1185

Glu Pro Val Leu Ser His Cys Arg Leu Leu Trp His Pro Ala Gln
    1190                1195                1200

Ile Arg Ala Pro Asp Glu Cys Ser His Cys Arg Leu Val Phe Lys
    1205                1210                1215

Val Arg Gly Arg His Gly Ser Tyr Ser Ala Lys Ser Ser Tyr Asp
```

-continued

```
            1220                1225                1230
Ala Phe Phe Arg Leu Gly Gln Leu Ser Arg Val Tyr Lys Leu Phe
    1235                1240                1245
Leu Ala Ala Glu Phe Pro Pro Ser Leu Val Cys Tyr Phe Ile Asn
    1250                1255                1260
Ala Phe Trp Phe Ser Cys Ala Leu Asp Asn Val Glu Asn Arg Ile
    1265                1270                1275
Val Phe Ile Val Phe Phe Ser Pro Phe Ile Phe Ile Met Cys Pro
    1280                1285                1290
Phe Lys Thr Pro Val Pro Arg Leu Ile Pro Ile Thr Thr Pro Leu
    1295                1300                1305
Asn Leu Ser Lys Ile Val Leu Leu Ser Ser Leu Pro Ala Ser Ser
    1310                1315                1320
Ala Ser Ser Leu Cys Pro Thr Ser Val Phe Ser Met Ser Thr Ala
    1325                1330                1335
Gln Thr Gly Pro Ala Asn Ser Ile Gly Asn Ala Ala Phe Phe Ile
    1340                1345                1350
Ala Ser Val Phe Phe Tyr Ser Ala Ile Ile Val Asn Pro Val Thr
    1355                1360                1365
Met Leu Pro Ala Val Val Cys Ser Thr Gln Leu Ser Ala Ala Phe
    1370                1375                1380
Pro Met Ala Cys Ala Ala Phe Val Val Pro Thr Gly Thr Met Lys
    1385                1390                1395
Pro Ile Thr Val Val Ser Phe Met Ser Cys Ala Ile Ser Arg Ala
    1400                1405                1410
Pro Val Phe Ala Pro Leu Leu Pro Thr Ser Gln Ala Thr Glu Ala
    1415                1420                1425
Met Ser Ile Ala Phe Lys Phe Arg Glu Asn Ser Tyr Asn Ala Ser
    1430                1435                1440
Phe Leu Lys Phe Ile His Arg Phe His Tyr Leu Thr Leu Phe Arg
    1445                1450                1455
Ile Val Glu Tyr Gly Asn Ile Ala Ser Gln Val Asn Gln Ile Tyr
    1460                1465                1470
Leu Pro Lys Thr Leu Glu Asn Tyr Phe Ile Thr Gln Phe Ser Gln
    1475                1480                1485
Ser Pro Ala Glu Lys Thr Ala Ser His Phe Leu Gly Ala Ala Glu
    1490                1495                1500
Ala Ser Leu Pro Ser Arg Phe Pro Tyr Leu Gly Gly Ala Arg Glu
    1505                1510                1515
Lys Ser Leu Pro Arg Pro Tyr Arg Arg Leu Leu Arg Leu Arg Phe
    1520                1525                1530
Phe Pro Asn Gln Pro Gln Ser Gly Ala Tyr His Ser Asp Lys Glu
    1535                1540                1545
Asp Gly Asp Leu Phe Arg Phe Val Ser Ser Pro His Lys Leu Ala
    1550                1555                1560
Asn Ile Phe Ala Leu Val Pro Glu Leu His Ile Leu Ala Ser Ser
    1565                1570                1575
Lys Arg Val Asn Asp Leu Asp Ala Pro Asp Leu Cys Lys Met Cys
    1580                1585                1590
Tyr Asn Leu Leu Pro Gln Ser Asp Arg Ser Lys Lys Arg Arg Glu
    1595                1600                1605
Ile Glu Lys Glu Arg Glu Arg Ile Val Asp Thr Arg Asp Arg Leu
    1610                1615                1620
```

```
Arg His Lys Asp Ile Leu Phe Ile Asn Ser Leu Ala Ser Pro Gln
    1625                1630                1635

Gly Trp Thr Tyr Lys Lys Lys Arg Cys Glu Ile Arg Cys Ala Glu
    1640                1645                1650

Glu Leu Lys Glu Asp Lys Ile Pro Leu Ile Ile Ser Lys Tyr Ala
    1655                1660                1665

Ser Val Thr Glu Ile Gln Glu Tyr Val Ser Gln Met Leu Glu Leu
    1670                1675                1680

Leu Arg Gly His Asp Leu Gly Leu Asp Glu Val Ala Arg His Glu
    1685                1690                1695

Ala Gln Leu Ile Arg Ile Ser Asn Ala Met Leu Arg Lys Ala Gly
    1700                1705                1710

Ala Thr Asn Gln Arg Arg His His Tyr Leu Ala Val Ala Leu Gln
    1715                1720                1725

Ile Phe Gly Val Trp Tyr Arg Lys Arg Lys Lys Pro Pro Asp Glu
    1730                1735                1740

Lys Trp Tyr Glu Glu Leu Ile Glu His Cys Glu Phe Tyr Asp Arg
    1745                1750                1755

Thr Ala His Phe Glu Val Leu Tyr Asp Ile Tyr Ala Gln
    1760                1765                1770

<210> SEQ ID NO 8
<211> LENGTH: 1770
<212> TYPE: PRT
<213> ORGANISM: Bacillus subtilis

<400> SEQUENCE: 8

Ala Pro Arg Ser Leu Ile Gly Trp Pro Cys Gly Tyr Arg Gly Gln Gly
1               5                   10                  15

Arg Ser Phe Val Phe Gln Pro Tyr Thr Leu Thr Gln Lys Arg Gly Thr
                20                  25                  30

Arg Phe Ala Cys Phe Leu Asn Pro Asp Leu Leu Lys Gly Asn Pro Ser
            35                  40                  45

Ser Lys Lys Tyr Arg Lys Pro Gly Arg Phe Val Ser Cys Leu Asn Thr
        50                  55                  60

Tyr Arg Tyr Phe Leu Phe Lys Gln Leu Phe Thr Phe Cys Ile Gly Thr
65                  70                  75                  80

Ile Cys Arg Ile Leu Leu Lys Arg Ser Asn Val Thr Lys Glu His Phe
                85                  90                  95

Phe Pro Ile Val Ile Phe Ser Tyr Ile Ile Pro Gln Leu Asn Leu Phe
                100                 105                 110

Pro Phe Phe Leu Phe Trp Ser Trp Glu Thr Leu Ala Lys Ala Lys Val
            115                 120                 125

Gln Leu Arg Asn Tyr Thr Cys Leu His Tyr Gln Ala Ser Pro His Glu
        130                 135                 140

Ser Leu Leu Gln Val Phe Arg Thr Arg Pro Leu Leu Pro Ile Cys Trp
145                 150                 155                 160

Gly Pro Ile Tyr Leu Ser Ser Phe Gln Arg Ser Leu Thr Asp His Leu
                165                 170                 175

Leu Leu Phe Arg Phe Ser Phe Arg Arg Phe Ile Leu Asp Pro Asn
            180                 185                 190

Ile Gln Tyr Leu Leu Leu His Cys Ser Pro Lys Ser Cys Ile Leu Ala
        195                 200                 205

Ser Arg Arg Asn Ile Leu Thr Ala Phe Thr Phe Ser Phe Val Asp Gly
```

-continued

```
            210                 215                 220
Lys Pro Asp Phe Pro Ser Thr Lys Asn Lys Glu Phe Gln Leu Asn Ile
225                 230                 235                 240

Glu Asn Arg Val Lys Phe Leu Ile Ala Ile Ile Val Leu Leu Ser Leu
                    245                 250                 255

His Ile Phe Ile Thr Asp Lys Pro Ala Pro His Phe Asp Arg Gly Ala
                    260                 265                 270

Thr Thr Phe Cys Met Gln Lys Leu Ala Arg Ser Gly His Ala Tyr Ala
                275                 280                 285

Arg Pro Pro Asn Leu Lys Leu Gln Leu Arg Cys His Phe Asp Pro His
290                 295                 300

Ser Phe Ser Ser Gly Ser His Leu Ile Asn Leu Phe Ala Tyr His
305                 310                 315                 320

Lys Arg Asn Arg Leu Ile Gly Leu Ala Gly Phe Lys Lys Tyr Ile Arg
                    325                 330                 335

Pro Lys Lys Ser Pro Leu Tyr Cys Phe Leu Pro Pro Phe Cys Ile Ser
                340                 345                 350

Ser Tyr Ile Phe Ser Ala Lys Ser Arg Ala Phe Cys Pro Ser Pro Cys
            355                 360                 365

Val Ser Asp Leu Gly Ser Thr Pro Ala Thr Thr Phe Ser Pro Cys
370                 375                 380

Ile Thr Pro Ile Pro Ala Trp Lys Phe Tyr Pro Ser Ala Ala Ser Thr
385                 390                 395                 400

Ala Met Trp Ile Ala Pro Ala Cys Ala Ser Pro Ala Ser Met Thr Val
                    405                 410                 415

Ser Ser Gly His Leu Trp Pro Phe Val Gly Gly His Ala Ser Asn Ile
                420                 425                 430

Ile Leu Glu Pro Ile Leu Leu Thr Asn Thr Ala Ile Leu Ser Gly Leu
            435                 440                 445

Gly Ser Thr Ala Pro Leu Pro Ile Leu Met Ile Phe Ser Ala Pro Met
450                 455                 460

Ser Thr Leu Ser Pro Met Arg Ala Ser Trp Ala Ser Leu Ser Phe Ser
465                 470                 475                 480

Phe Asn Arg Cys Lys Ile Leu Val Pro Arg Gly Tyr Thr Val Ser Phe
                    485                 490                 495

Ala Ala Ala Leu Arg Ser Pro Leu Ile Ala Val Leu Val Pro Ser Leu
                500                 505                 510

Leu His Ile Val Asp Ser Ala Ala Leu Cys Ser Ala Cys Tyr Leu Phe
            515                 520                 525

Val Cys Trp Leu Met Lys Thr Pro Thr Pro Val Thr Phe Ala Ser Leu
530                 535                 540

Gly Leu Lys Val Gln Leu Ser Gly Phe Thr Val Phe Cys Gly Thr Arg
545                 550                 555                 560

Thr Met Ser Ser Val Thr Ser Glu Ile Gly Ser Ser Ala Leu Thr Ile
                565                 570                 575

Gln Ser Ile Ala Gly Val His Ile Lys Val Val Ala Arg Ala Ser Ser
                580                 585                 590

Ser Phe Phe Arg Ser Glu Ala Lys Pro Thr Phe Met Asn Val Ser
            595                 600                 605

Ser Val Ser Arg Met Ile Gly Ser Thr Lys Phe Ile Arg Ala Ser Ser
            610                 615                 620

Pro Met Met Asp Thr Tyr Thr Ser Pro Pro Glu Ala Thr Pro Leu Lys
625                 630                 635                 640
```

-continued

```
Thr Leu Ser Pro Gln Lys Ser Ile Met Lys Lys Ala Gly Leu Ser Ile
            645                 650                 655
Pro Pro Val Cys Ala Gly Leu Lys Ile Glu Pro Ser Pro Lys Asp Ile
            660                 665                 670
Phe Ser Thr Gly Lys Asn Cys Asn Val Ser Ile Val Trp Ile Pro Arg
            675                 680                 685
Ser Ile Leu Ser Val Ala Phe Gly Val Phe Ser Tyr Ser Pro Ser Trp
            690                 695                 700
Thr Leu Phe Arg Leu Phe Leu Cys Leu Arg Ile Trp Ser Phe Leu Leu
705                 710                 715                 720
Ala His Leu Pro Arg Leu Ile Ser Leu Ser Lys Leu Pro His Glu Asp
            725                 730                 735
Gln Arg Cys Cys Gln Leu Ser Arg Cys Lys Asp Ser Gln Gln Asn Leu
            740                 745                 750
Phe Asp Ile Leu Pro His Ala Gln Phe Leu Leu Thr Val Ser His Asn
            755                 760                 765
Leu Leu Leu Phe Cys Leu Leu Asp Pro Phe Leu Ser Pro Pro Leu Arg
770                 775                 780
Gly Asn Arg Leu Gly Asn Arg Arg Leu Gly His Arg Arg Phe Gln Pro
785                 790                 795                 800
Phe Val Phe Gln Leu Ser Phe Cys Arg Leu Lys Ser His Asn Leu Phe
            805                 810                 815
Pro Gly Thr Met Leu Leu Phe Met Pro Lys Leu Pro Ile Leu Gln Pro
            820                 825                 830
His Arg Ser Ser Leu Trp Ile Arg Gly Ser Leu Leu Cys Leu Ser Ser
            835                 840                 845
Arg Arg Leu Val Ala Tyr Ser Arg Phe Ser Arg Lys Leu Phe Phe Ser
850                 855                 860
Arg Ser Leu Ser Tyr Arg Ile Arg Tyr Ser Arg Phe Ile Tyr Thr Asp
865                 870                 875                 880
Ile Lys Ala Tyr Leu Trp His Phe Tyr Ser Gly Val Phe Trp Leu Leu
            885                 890                 895
Arg Arg Leu Arg Phe Arg Ser Lys Ser Leu Phe Ile Gln Met Asn Gly
            900                 905                 910
Ile Ser Ser Ala Ser Ser Ala Lys Phe Phe Pro Ser Thr Met Met Thr
            915                 920                 925
Thr Ser Ser Ser Leu Ser Phe Ser Pro Ser Lys Thr Ala Arg Ala
            930                 935                 940
Ser Cys Ala Val Gly Ser Thr Met Leu Lys Ile Ala Val Cys Pro Leu
945                 950                 955                 960
Pro Ser Ile Gln Val Gly Ser Leu Ser Ile Ala Ser Leu Ser Ser
            965                 970                 975
Arg Gly Ile Thr Ser Cys Leu Val Ser Glu Trp Val Ala Asn Val Thr
            980                 985                 990
Leu Met Ser Trp Arg Ser Val Phe Val Pro Ile Leu Ala Ser Leu Asp
            995                 1000                1005
Lys Val Thr Ala Asn Ser Ser Leu Leu Asp Thr Gly Asp Ser Lys
            1010                1015                1020
Arg Gly Pro Cys Met Lys Gly Ser Ile Ala Phe Phe Pro Pro Thr
            1025                1030                1035
Arg Phe Leu Ala Pro Trp Val Ser Ala Ala Thr Ser Arg Ala Ser
            1040                1045                1050
```

-continued

```
Ala Gln Pro Asp Gly Pro Ala Pro Thr Met Gln Ser Ile Ile Phe
    1055                1060                1065

Ser Ser Pro Val Ile Ala Leu Thr Gly Ser Ser Met Ser Ile Ala
    1070                1075                1080

Phe Phe Cys Asn Phe Ile Ile Val Met Leu Ser Lys Ile Tyr Arg
    1085                1090                1095

Leu Arg Val Val Ser Thr Ser Arg Ser Thr Ser Met Val Ser Gly
    1100                1105                1110

Val Ser Lys Pro Val Asn Leu Thr Pro Tyr Val Phe Ser Thr Ser
    1115                1120                1125

Pro Phe Ser Cys Thr Ala Asn Thr Ile Pro Ser Thr Gly Asn Pro
    1130                1135                1140

Ser Ser Gly Thr Asn Thr Arg Thr Cys Glu Ser His Arg Val Pro
    1145                1150                1155

Ser Thr Asn Pro Glu Arg Gln Ser Gln Pro Gly Cys Ser Cys Ala
    1160                1165                1170

Ala Ser Phe Trp Ile Ala Ala Ser Pro Arg Pro Thr Ser Arg Tyr
    1175                1180                1185

Lys Arg Trp Ser Pro Arg Pro Met Pro Lys Ile Leu Leu Asn Phe
    1190                1195                1200

Ala Leu Ser Ser Cys Pro Ser Val Thr Ser Ala Leu Ser Ala Ser
    1205                1210                1215

Pro Asn Lys Gly Ser Arg Arg Leu Pro Met Pro Ala Cys Ile Lys
    1220                1225                1230

Arg Ser Arg Pro Thr Arg Phe Ile Phe Ser Lys Val Phe Leu Gly
    1235                1240                1245

Arg Phe Ile Ala Pro Arg Ser Pro Pro Ser Leu Ile Glu Ser Leu
    1250                1255                1260

Thr Gly Ser Ile Ser Ala Phe Ser Cys Leu Leu Phe Tyr Lys Cys
    1265                1270                1275

Val Leu Ile Phe Leu Ser Pro Lys Ser Lys Asp Cys Ile Asp Cys
    1280                1285                1290

Phe Leu Ile Pro Ile Met His Ile Asp Tyr Leu Ser Ile Asn Thr
    1295                1300                1305

Cys Thr Lys Phe Asp Ser Asp Tyr Tyr Ser Ser Lys Ile Ile Lys
    1310                1315                1320

Asn Arg Ala Leu Gln Gln Ala Ser Cys Phe Ile Arg Gln Glu Ser
    1325                1330                1335

Met Ala Tyr Val Cys Ile Val Asn Ile His Ser Pro Asn Trp Ala
    1340                1345                1350

Cys Lys Phe Tyr Arg Lys Ser Arg Phe Phe His Arg Phe Cys Phe
    1355                1360                1365

Phe Ile Ile Ser Asn Asp Cys Gln Ala Ser Asp Ser Ala Cys
    1370                1375                1380

Arg Cys Met Val Ile Ile Asp Ala Ile Phe Ser Cys Phe Ala Asp
    1385                1390                1395

Arg Leu Cys Cys Val Ser Ser Thr Tyr Arg Asp Asp Lys Ser Asn
    1400                1405                1410

Tyr Cys Ser Phe Val Asp Phe Leu Ser Asp Leu Thr Gly Ala Cys
    1415                1420                1425

Phe Arg Ala Val Phe Thr Tyr Ile Thr Ser Asn Arg Gly Asn Phe
    1430                1435                1440

His Cys Ile Val Ala Lys Phe Leu Lys Ser Phe Val Thr Phe Tyr
```

-continued

```
            1445                1450                1455

Pro Ser Phe Ser Ile Ile His Ser Phe Pro Asp Gly Ile Arg Ile
    1460                1465                1470

Arg Tyr Cys Val Pro Cys Lys Pro Tyr Leu Pro Thr Lys Ile Asn
    1475                1480                1485

Ile Arg Leu Phe Asp Asn Ser Phe Ile Ala Ile Pro Ser Arg Glu
    1490                1495                1500

Asn Ile Gly Phe Ser Phe Ser Arg Leu Cys Ser Cys Val Ile Leu
    1505                1510                1515

Ser Ser Val Ser Val Ser Arg Trp Ser Lys Arg Gln Phe Ser Ser
    1520                1525                1530

Ser Ser Ile Thr Pro Ala Ile Pro Thr Ser Phe Phe Ser Glu Ser
    1535                1540                1545

Thr Ser Ile Arg Cys Ile Leu Thr Phe Gly Glu Arg Trp Pro Ile
    1550                1555                1560

Pro Phe Cys Ile Ile Ser Ala Lys Phe Cys Lys Asn Leu Val Cys
    1565                1570                1575

Thr Ser Thr Gly Phe Ser Asn Val Cys Leu Lys Lys Ser Arg Gln
    1580                1585                1590

Pro Cys Ser Ser Met Glu Tyr Leu Leu Ala Ser Ala Thr Ile Leu
    1595                1600                1605

Arg Gln Lys Lys Gln Thr Arg Asn Arg Lys Thr Pro His Arg
    1610                1615                1620

Asp Ser Gly Ala Phe Pro Thr Gln Arg Tyr Ser Ile His Gln Gln
    1625                1630                1635

Thr Cys Gln Ala Ala Gly Met Tyr Val Lys Lys Glu Gln Met Arg
    1640                1645                1650

Asp Gln Met Ser Gly Gly Thr Glu Arg Gln Asn Ala Thr Tyr His
    1655                1660                1665

Lys Leu Cys Leu Arg Asn Arg Asn Thr Arg Leu Gly Ile Ala Tyr
    1670                1675                1680

Thr Arg Ala Phe Pro Trp Ser Ala Arg Leu Arg Arg Ser Gly Pro
    1685                1690                1695

Thr Arg Ser Ser Ser Asp Pro His Gln Glu Gly Asp Thr Lys Lys
    1700                1705                1710

Gly Arg Ser Tyr Glu Ala Lys Gln Ser Ser Ile Phe Gly Ser Cys
    1715                1720                1725

Ala Ser Tyr Leu Gly Gly Leu Leu Thr Lys Thr Glu Lys Ala Ser
    1730                1735                1740

Arg Gly Glu Leu Ile Arg Arg Ile Asn Pro Met Phe Leu Gly Thr
    1745                1750                1755

Asp Cys Ser Val Arg Ser Leu Arg Tyr Leu Ser Ala
    1760                1765                1770

<210> SEQ ID NO 9
<211> LENGTH: 100
<212> TYPE: DNA
<213> ORGANISM: Synthetic

<400> SEQUENCE: 9
tgattaaaaa acatcaccct tcggatcgaa gggtgatgtt ttgttttct caaattgtaa    60 gtttatttca ttgcgtactt taaaaggat cgctataata                         100

<210> SEQ ID NO 10
```

```
<211> LENGTH: 15
<212> TYPE: DNA
<213> ORGANISM: Synthetic

<400> SEQUENCE: 10
gaattcccgg gatcc                                                    15

<210> SEQ ID NO 11
<211> LENGTH: 80
<212> TYPE: DNA
<213> ORGANISM: Synthetic

<400> SEQUENCE: 11
aattcatgca tggatccgac ggtaaataac aaaagagggg agggaaacaa atggaagagt   60
attatatgaa gctggcctta                                               80

<210> SEQ ID NO 12
<211> LENGTH: 80
<212> TYPE: DNA
<213> ORGANISM: Synthetic

<400> SEQUENCE: 12
gatctaaggc cagcttcata taatactctt ccatttgttt ccctcccctc ttttgttatt   60
taccgtcgga tccatgcatg                                               80

<210> SEQ ID NO 13
<211> LENGTH: 66
<212> TYPE: DNA
<213> ORGANISM: Synthetic

<400> SEQUENCE: 13
tcgacggatc cttttagaga ggaagatttg catgtttcat ccgatagaag aagcactgga   60
cgcttt                                                              66

<210> SEQ ID NO 14
<211> LENGTH: 62
<212> TYPE: DNA
<213> ORGANISM: Synthetic

<400> SEQUENCE: 14
aaagcgtcca gtgcttcttc tatcggatga acatgcaaa tcttcctctc taaaaggatc    60
cg                                                                  62

<210> SEQ ID NO 15
<211> LENGTH: 78
<212> TYPE: DNA
<213> ORGANISM: Synthetic

<400> SEQUENCE: 15 cgattttgc ataaagccaa tgaaataag acccaacaaa ccattacaaa agccttctta     60
agcgaaaacg gcttttag                                                 78

<210> SEQ ID NO 16
<211> LENGTH: 80
<212> TYPE: DNA
<213> ORGANISM: Synthetic

<400> SEQUENCE: 16
aattctaaaa gccgttttcg cttaagaagg cttttgtaat ggtttgttgg gtcttatttt   60
cattggcttt atgcaaaaat                                               80
```

-continued

```
<210> SEQ ID NO 17
<211> LENGTH: 54
<212> TYPE: DNA
<213> ORGANISM: Synthetic

<400> SEQUENCE: 17
ggagctacaa cacattatga ttatgtttgc aatgaagctg ctaaaggaat tgct          54
```

The invention claimed is:

1. A method for producing a polypeptide that has ORF5 activity and is in the riboflavin biosynthetic pathway comprising:

(a) providing an isolated polynucleotide template comprising a bacterial rib operon which includes a bacterial ORF5 structural gene and an exogenous promoter, the ORF5 structural gene being hybridizable to *B. subtilis* rib ORF5 and encoding a polypeptide that has ORF5 activity, wherein the promoter is positioned such that it promotes transcription of the ORF5 structural gene;

(b) carrying out transcription and translation on the polynucleotide template to produce a polypeptide that has ORF5 activity; and (c) recovering the polypeptide.

2. The method according to claim 1 wherein step (b) comprises coupled transcription and translation.

3. The method according to claim 1, wherein step (b) comprises in vitro coupled transcription and translation.

4. The method according to claim 1, wherein step (b) comprises carrying out in vitro coupled transcription and translation with an S-30 fraction kit.

5. The method according to claim 1, further comprising isolating the polypeptide on an SDS polyacrylamide gel.

6. The method according to claim 1, wherein the ORF5 structural gene comprises nucleotides 1101–2183 of SEQ ID NO:1.

7. The method according to claim 6, wherein the ORF5 structural gene consists of nucleotides 1101–2183 of SEQ ID NO:1.

8. The method according to claim 1, wherein the ORF5 structural gene consists of a nucleotide sequence that encodes a polypeptide comprising amino acid residues 346–706 of SEQ ID NO:5.

* * * * *